(12) United States Patent
Shi et al.

(10) Patent No.: US 10,634,602 B2
(45) Date of Patent: Apr. 28, 2020

(54) FLUIDIC CARTRIDGE FOR CYTOMETRY AND ADDITIONAL ANALYSIS

(71) Applicant: CYTOCHIP INC., Irvine, CA (US)

(72) Inventors: Wendian Shi, Monrovia, CA (US); Yuzhe Ding, Monrovia, CA (US)

(73) Assignee: CYTOCHIP INC., Irvine, CA (US)

( * ) Notice: Subject to any disclaimer, the term of this patent is extended or adjusted under 35 U.S.C. 154(b) by 0 days.

(21) Appl. No.: 15/803,133

(22) Filed: Nov. 3, 2017

(65) Prior Publication Data

US 2018/0052093 A1 Feb. 22, 2018

Related U.S. Application Data

(63) Continuation-in-part of application No. 15/209,226, filed on Jul. 13, 2016, now Pat. No. 10,077,999, and (Continued)

(51) Int. Cl.
*G01N 1/18* (2006.01)
*G01N 1/10* (2006.01)
(Continued)

(52) U.S. Cl.
CPC ..... *G01N 15/1404* (2013.01); *A61B 10/0096* (2013.01); *B01F 11/00* (2013.01);
(Continued)

(58) Field of Classification Search
CPC ............ G01N 1/18; G01N 1/10; G01N 15/06; G01N 33/00; G01N 33/48; G01N 35/00; G01N 15/1404; G01N 15/1484; G01N 33/5094; G01N 33/56972; A61J 1/06; A61B 10/0096; B01F 11/00; B01F 11/0071; B01F 13/0059; B01F 13/0084;
(Continued)

(56) References Cited

U.S. PATENT DOCUMENTS 4,895,500 A 1/1990 Hok et al.
4,983,523 A 1/1991 Li et al.
(Continued)

FOREIGN PATENT DOCUMENTS

WO 2016/200922 A1 12/2016
WO 2017/011554 A1 1/2017

OTHER PUBLICATIONS

Al-Faqheri et al., Development of a passive liquid valve (PLV) utilizing a pressure equilibrium phenomenon on the centrifugal microfluidic platform. Sensors, 15(3):4658-4676 (2015).
(Continued)

*Primary Examiner* — Brian J. Sines
(74) *Attorney, Agent, or Firm* — Lathrop GPM LLP

(57) ABSTRACT

The disclosure relates to devices and methods for analyzing particles in a sample. In various embodiments, the present disclosure provides devices and methods for cytometry and additional analysis. In various embodiments, the present disclosure provides a cartridge device and a reader instrument device, wherein the reader instrument device receives, operates, and/or actuates the cartridge device. In various embodiments, the present disclosure provides a method of using a device as disclosed herein for analyzing particles in a sample.

51 Claims, 30 Drawing Sheets

Related U.S. Application Data a continuation-in-part of application No. 15/176,729, filed on Jun. 8, 2016, now Pat. No. 10,022,720.

(60) Provisional application No. 62/497,075, filed on Nov. 7, 2016, provisional application No. 62/192,488, filed on Jul. 14, 2015, provisional application No. 62/174,776, filed on Jun. 12, 2015.

(51) Int. Cl.

| | | |
|---|---|---|
| *G01N 15/06* | (2006.01) | |
| *G01N 33/00* | (2006.01) | |
| *G01N 33/48* | (2006.01) | |
| *G01N 15/14* | (2006.01) | |
| *B01L 3/00* | (2006.01) | |
| *G01N 33/50* | (2006.01) | |
| *G01N 33/569* | (2006.01) | |
| *A61B 10/00* | (2006.01) | |
| *B01F 11/00* | (2006.01) | |
| *B01F 13/00* | (2006.01) | |
| *G01N 15/10* | (2006.01) | |
| *G01N 15/00* | (2006.01) | |
| *A61B 5/00* | (2006.01) | |

(52) U.S. Cl.
CPC ...... *B01F 11/0071* (2013.01); *B01F 13/0059* (2013.01); *B01F 13/0084* (2013.01); *B01L 3/5027* (2013.01); *B01L 3/50273* (2013.01); *B01L 3/502715* (2013.01); *B01L 3/502723* (2013.01); *B01L 3/502738* (2013.01); *B01L 3/502761* (2013.01); *G01N 15/06* (2013.01); *G01N 15/1484* (2013.01); *G01N 33/5094* (2013.01); *G01N 33/56972* (2013.01); *A61B 5/0071* (2013.01); *B01L 2200/143* (2013.01); *B01L 2300/0645* (2013.01); *B01L 2300/0654* (2013.01); *B01L 2300/0681* (2013.01); *B01L 2300/087* (2013.01); *B01L 2300/0864* (2013.01); *B01L 2300/0867* (2013.01); *B01L 2300/0877* (2013.01); *B01L 2300/0887* (2013.01); *B01L 2300/161* (2013.01); *B01L 2300/168* (2013.01); *B01L 2400/0406* (2013.01); *B01L 2400/0409* (2013.01); *B01L 2400/0457* (2013.01); *B01L 2400/0487* (2013.01); *B01L 2400/0688* (2013.01); *B01L 2400/088* (2013.01); *G01N 2015/008* (2013.01); *G01N 2015/0073* (2013.01); *G01N 2015/0084* (2013.01); *G01N 2015/0693* (2013.01); *G01N 2015/1006* (2013.01); *G01N 2015/1486* (2013.01)

(58) Field of Classification Search
CPC ............. B01L 3/5027; B01L 3/502715; B01L 3/502723; B01L 3/502738; B01L 3/502761
USPC .............. 422/50, 68.1, 81, 82, 82.05, 82.01; 436/43, 63, 174, 180, 177
See application file for complete search history.

(56) References Cited

U.S. PATENT DOCUMENTS

| | | | |
|---|---|---|---|
| 5,096,669 A | 3/1992 | Lauks et al. | |
| 5,110,724 A | 5/1992 | Hewett | |
| 5,213,965 A | 5/1993 | Jones | |
| 5,409,665 A | 4/1995 | Burd | |
| 5,478,750 A | 12/1995 | Bernstein et al. | |
| 5,591,643 A | 1/1997 | Schembri | |
| 6,033,631 A | 3/2000 | Zuckermann et al. | |
| 6,100,084 A | 8/2000 | Miles et al. | |
| 6,369,893 B1 | 4/2002 | Christel et al. | |
| 6,382,228 B1 | 5/2002 | Cabuz et al. | |
| 6,549,275 B1 | 4/2003 | Cabuz et al. | |
| 6,664,110 B1 | 12/2003 | Tsuji et al. | |
| 6,750,060 B2 | 6/2004 | Ozasa et al. | |
| 6,752,961 B2 | 6/2004 | Kopf-Sill et al. | |
| 6,804,984 B2 | 10/2004 | Shibata | |
| 7,016,022 B2 | 3/2006 | Fritz et al. | |
| 7,061,595 B2 | 6/2006 | Cabuz et al. | |
| 7,113,266 B1 | 9/2006 | Wells | |
| 7,130,046 B2 | 10/2006 | Fritz et al. | |
| 7,172,897 B2 | 2/2007 | Blackburn et al. | |
| 7,215,425 B2 | 5/2007 | Rezachek et al. | |
| 7,220,595 B2 | 5/2007 | Nugent et al. | |
| 7,318,900 B2 | 1/2008 | DeMarco | |
| 7,328,722 B2 | 2/2008 | Rich et al. | |
| 7,420,659 B1 | 9/2008 | Cabuz et al. | |
| 7,471,394 B2 | 12/2008 | Padmanabhan et al. | |
| 7,521,243 B2 | 4/2009 | Lindberg et al. | |
| 7,534,331 B2 | 5/2009 | Kayyem | |
| 7,553,453 B2 | 6/2009 | Gu et al. | |
| 7,580,120 B2 | 8/2009 | Hamada et al. | |
| 7,595,169 B2 | 9/2009 | Swaim et al. | |
| 7,632,462 B2 | 12/2009 | Holtlund et al. | |
| 7,641,856 B2 | 1/2010 | Padmanabhan et al. | |
| 7,760,351 B2 | 7/2010 | Cox et al. | |
| 7,771,658 B2 | 8/2010 | Larsen | |
| 7,800,742 B2 | 9/2010 | Fukuda et al. | |
| 7,832,429 B2 | 11/2010 | Young et al. | |
| 7,842,234 B2 | 11/2010 | Lauks et al. | |
| 7,843,563 B2 | 11/2010 | Fritz et al. | |
| 7,863,035 B2 | 1/2011 | Clemens et al. | |
| 7,894,047 B2 | 2/2011 | Hamada et al. | |
| 7,910,062 B2 | 3/2011 | Yu et al. | |
| 8,029,746 B2 | 10/2011 | Yu et al. | |
| 8,034,296 B2 | 10/2011 | Cox et al. | |
| 8,071,051 B2 | 12/2011 | Padmanabhan et al. | |
| 8,097,225 B2 | 1/2012 | Padmanabhan et al. | |
| 8,124,024 B2 | 2/2012 | Ching et al. | |
| 8,168,443 B2 | 5/2012 | Yu et al. | |
| 8,202,492 B2 | 6/2012 | Linder et al. | |
| 8,283,177 B2 | 10/2012 | Ball et al. | |
| 8,293,175 B2 | 10/2012 | Holtlund et al. | |
| 8,361,410 B2 | 1/2013 | Padmanabhan et al. | |
| 8,367,023 B2 | 2/2013 | Bae et al. | |
| 8,383,043 B2 | 2/2013 | Padmanabhan et al. | |
| 8,518,328 B2 | 8/2013 | Padmanabhan et al. | |
| 8,540,946 B2 | 9/2013 | Padmanabhan et al. | |
| 8,545,756 B2 | 10/2013 | Holtlund et al. | |
| 8,567,425 B2 | 10/2013 | Tan et al. | |
| 8,573,033 B2 | 11/2013 | Larsen | |
| 8,591,829 B2 | 11/2013 | Taylor et al. | |
| 8,646,842 B2 | 2/2014 | Barruss | |
| 8,663,583 B2 | 3/2014 | Kelley et al. | |
| 8,741,233 B2 | 6/2014 | Bardell et al. | |
| 8,741,234 B2 | 6/2014 | Wang et al. | |
| 8,741,235 B2 | 6/2014 | Janisch et al. | |
| 8,747,747 B2 | 6/2014 | Hunter | |
| 8,828,320 B2 | 9/2014 | Bardell et al. | |
| 8,835,184 B2 * | 9/2014 | Redmond ......... | B01L 3/502715 436/518 |
| 8,846,380 B2 | 9/2014 | Bae et al. | |
| 8,940,499 B2 | 1/2015 | Kuang et al. | |
| 8,945,913 B2 | 2/2015 | Kasdan et al. | |
| 8,980,635 B2 | 3/2015 | Kelley et al. | |
| 9,029,158 B2 | 5/2015 | Tai et al. | |
| 9,140,694 B2 | 9/2015 | Holtlund et al. | |
| 9,234,884 B2 | 1/2016 | Tai et al. | |
| 9,494,570 B2 | 11/2016 | Bransky et al. | |
| 2002/0042125 A1 | 4/2002 | Petersen et al. | |
| 2003/0030783 A1 | 2/2003 | Roche et al. | |
| 2004/0005247 A1 | 1/2004 | Carp | |
| 2004/0241042 A1 | 12/2004 | Pugia et al. | |
| 2005/0136552 A1 | 6/2005 | Buechler | |
| 2006/0177347 A1 | 8/2006 | Larsen et al. | |
| 2007/0039835 A1 | 2/2007 | Rossier et al. | |
| 2007/0154351 A1 | 7/2007 | Bae et al. | |
| 2008/0085560 A1 | 4/2008 | Ekberg | |

(56) References Cited

U.S. PATENT DOCUMENTS

| | | |
|---|---|---|
| 2008/0199971 A1 | 8/2008 | Tondra |
| 2009/0075390 A1 | 3/2009 | Linder et al. |
| 2009/0291507 A1 | 11/2009 | Clemens et al. |
| 2010/0288689 A1 | 11/2010 | Zhu et al. |
| 2011/0002812 A1 | 1/2011 | Asogawa et al. |
| 2012/0140205 A1* | 6/2012 | Kaduchak .......... G01N 15/1404 356/39 |
| 2012/0287525 A1 | 11/2012 | Matsui et al. |
| 2013/0130262 A1 | 5/2013 | Battrell et al. |
| 2013/0137135 A1* | 5/2013 | Tai .................... G01N 21/6486 435/34 |
| 2013/0343955 A1 | 12/2013 | Doyle et al. |
| 2013/0344475 A1 | 12/2013 | Jovanovich et al. |
| 2014/0016131 A1* | 1/2014 | Swalwell .......... G01N 15/1434 356/343 |
| 2014/0038809 A1 | 2/2014 | Bransky et al. |
| 2014/0170678 A1 | 6/2014 | Kasdan et al. |
| 2014/0170680 A1 | 6/2014 | Meissonnier et al. |
| 2014/0211205 A1 | 7/2014 | Bardell et al. |
| 2014/0301915 A1 | 10/2014 | Doyle et al. |
| 2014/0349381 A1 | 11/2014 | Battrell et al. |
| 2014/0356941 A1 | 12/2014 | Bransky et al. |
| 2015/0151295 A1 | 6/2015 | Kimura et al. |
| 2015/0309049 A1 | 10/2015 | Kasdan et al. |
| 2016/0129445 A1 | 5/2016 | Corey et al. |
| 2016/0130640 A1 | 5/2016 | Wright et al. |
| 2016/0361715 A1 | 12/2016 | Shi et al. |
| 2017/0016753 A1 | 1/2017 | Shi et al. |

OTHER PUBLICATIONS

Ducree et al., The centrifugal microfluidic Bio-disk platform. Journal of Micromechanics and Microengineering, vol. 17:S103-S115 (2007).

Henning, Micro-Pneumatic Logic. 2004 ASME International Mechanical Engineering Congress and RD&D Expo, Anaheim, CA, Nov. 15-21, 2004.

International Search Report and Written Opinion issued in related International Application No. PCT/US2016/036426 dated Sep. 6, 2016.

International Search Report and Written Opinion issued in related International Patent Application No. PCT/US2016/042089 dated Dec. 8, 2016.

Maleki, T et al, Point-of-Care, Portable Microfluidic Blood Analyzer System, Microfluidics, BioMEMS, and Medical Microsystems, Feb. 9, 2012, 14 pages.

PCT/US2017/062765, International Search Report dated Jan. 29, 2018, 9 pages.

PCT/US2018/031893, International Search Report dated Aug. 3, 2018, 12 pages.

Four-part leukocyte differential count based on sheathless microflow cytometer and fluorescent dye assay, W. Shi, L. Guo, H. Kasdan, YC Tai—Lab on a Chip, 2013.

* cited by examiner

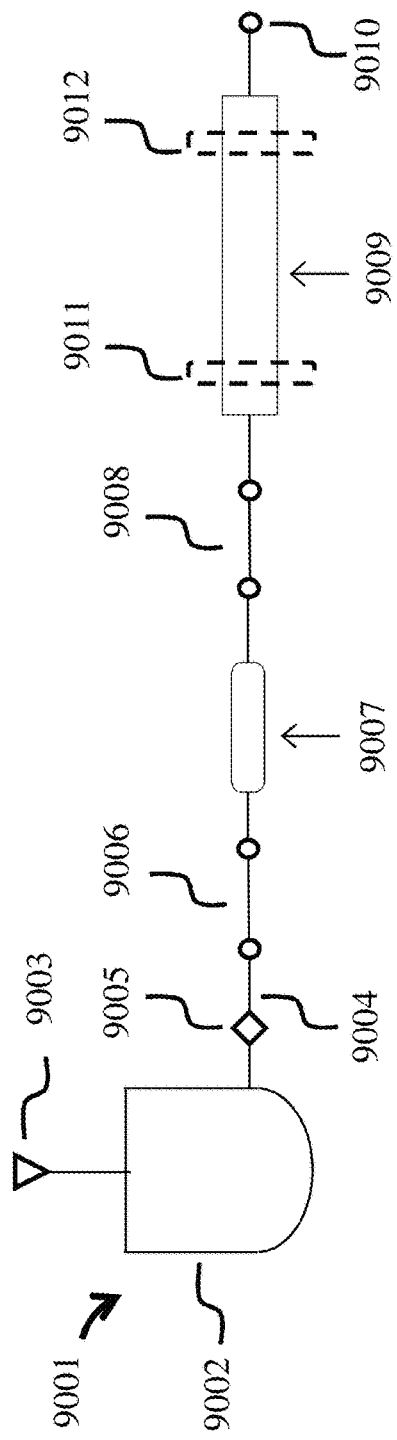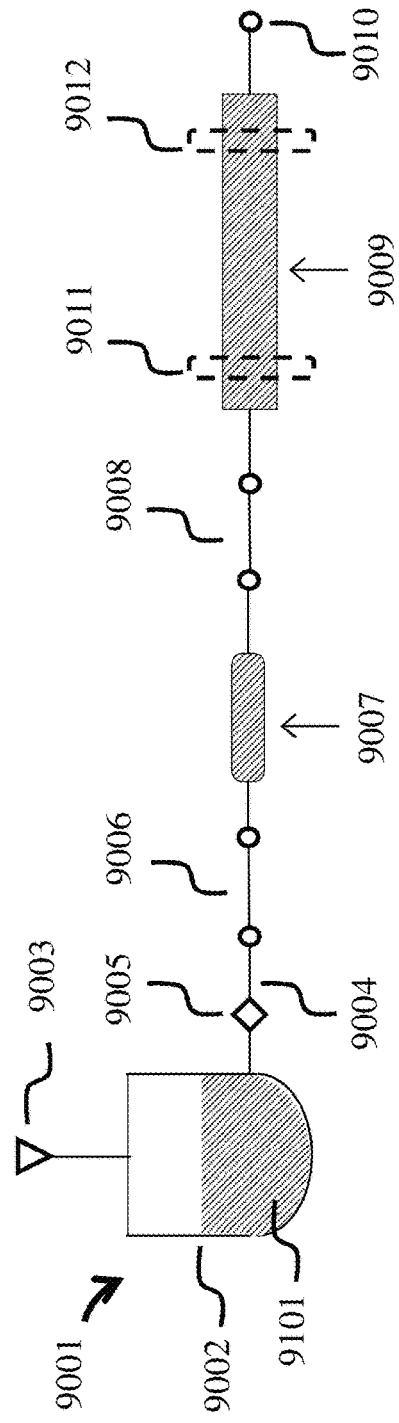
FIG. 9A
FIG. 9B

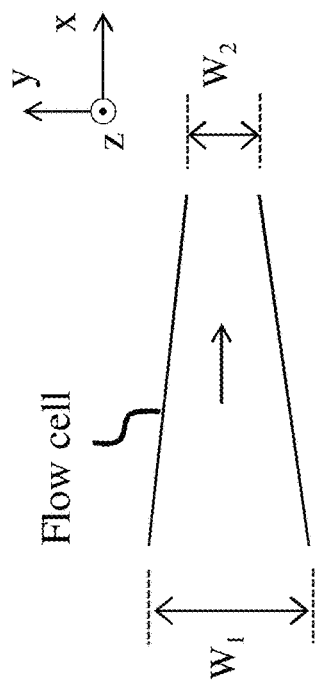
FIG. 15A
FIG. 15B
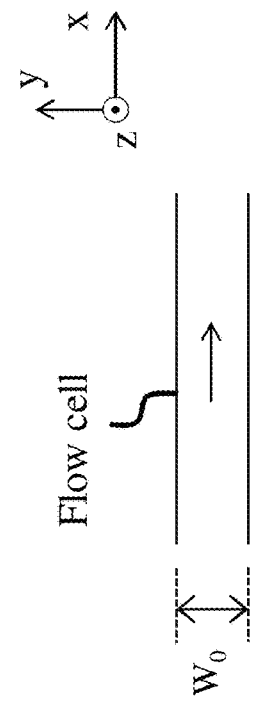
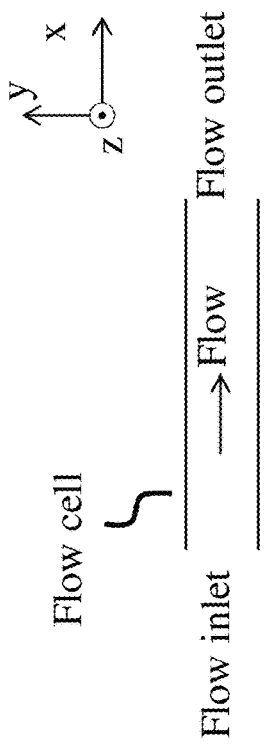
FIG. 15C
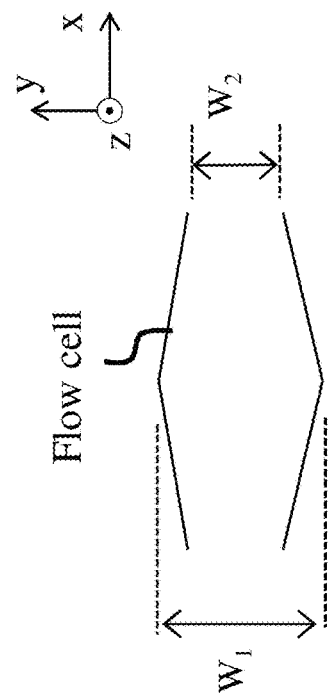
FIG. 15D

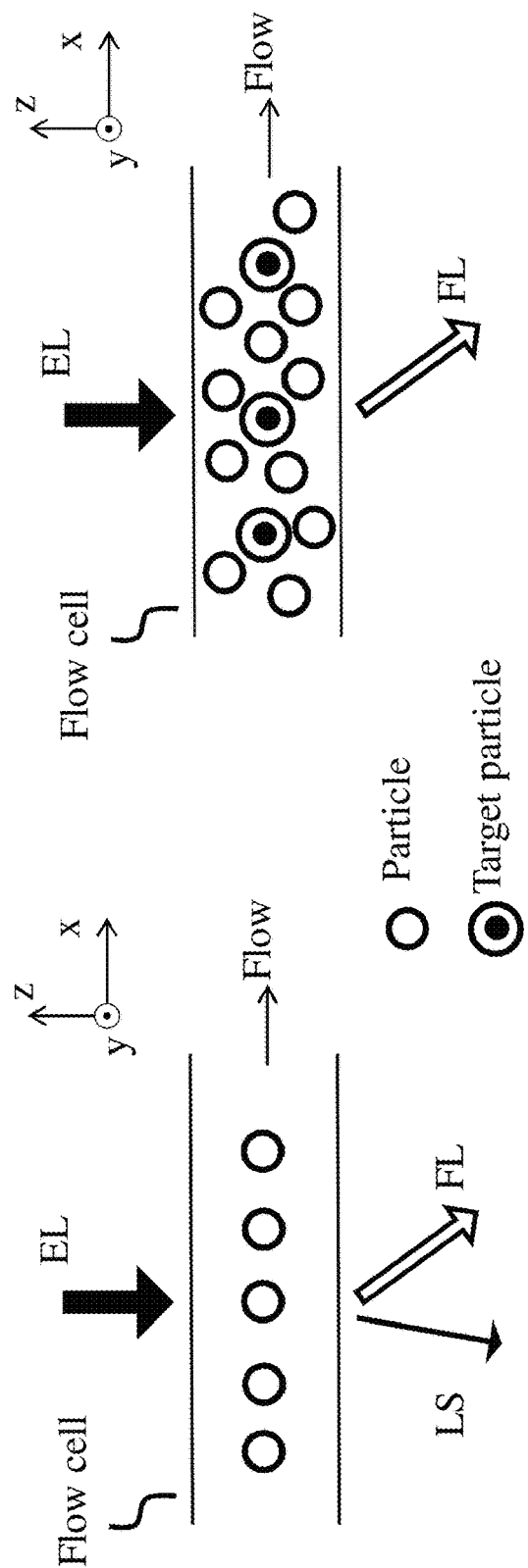

FLUIDIC CARTRIDGE FOR CYTOMETRY AND ADDITIONAL ANALYSIS

PRIORITY CLAIM

This application claims priority to U.S. Provisional Patent Application No. 62/497,075, filed on Nov. 7, 2016, entitled "Fluidic Cartridge for Cytometry and Additional Analysis", the entire contents of which are incorporated herein by reference and relied upon.

This application is a continuation-in-part of U.S. patent application Ser. No. 15/176,729, filed on Jun. 8, 2016, entitled "Fluidic Units and Cartridges for Multi-Analyte Analysis", which claims priority to U.S. Provisional Patent Application No. 62/174,776, filed on Jun. 12, 2015, the entire contents of each of which are incorporated herein by reference and relied upon.

This application is related to International Application PCT/US2016/036426, filed on Jun. 8, 2016, entitled "Fluidic Units and Cartridges for Multi-Analyte Analysis", which claims priority to U.S. Provisional Patent Application No. 62/174,776, filed on Jun. 12, 2015, the entire contents of each of which are incorporated herein by reference and relied upon.

This application is a continuation-in-part of U.S. patent application Ser. No. 15/209,226, filed on Jul. 13, 2016, entitled "Volume Sensing in Fluidic Cartridge", which claims priority to U.S. Provisional Patent Application No. 62/192,488, filed on Jul. 14, 2015, the entire contents of each of which are incorporated herein by reference and relied upon.

This application is related to International Application PCT/US2016/042089, filed on Jun. 13, 2016, entitled "Volume Sensing in Fluidic Cartridge", which claims priority to U.S. Provisional Patent Application No. 62/192,488, filed on Jul. 14, 2015, the entire contents of each of which are incorporated herein by reference and relied upon.

FIELD OF THE DISCLOSURE

The disclosure relates to medicine and cytometry.

BACKGROUND

All publications cited herein are incorporated by reference in their entirety to the same extent as if each individual publication or patent application was specifically and individually indicated to be incorporated by reference. The following description includes information that may be useful in understanding the present disclosure. It is not an admission that any of the information provided herein is prior art or relevant to the presently disclosure, or that any publication specifically or implicitly referenced is prior art.

Flow cytometry is a popular tool for cellular analysis of biological samples. Typical cytometry analyses involve two parts. The first part is sample preparation. For example, some cytometry analyses label target cells with a specific fluorophore, so that these cells can be detected by an optical measurement of fluorescence signals. In another example, some cytometry analyses require selectively lysing cells in samples, leaving only target cells intact for cytometry measurement. The second part is sample analysis. Usually the sample stream is focused into a narrow stream when flowing through a flow cell, where the target cells are measured one by one for optical or other signals. This narrow sample stream is usually obtained by hydrodynamic focusing of sheath flow.

The signal measured in flow cytometry can be used to evaluate individual target cells' characteristics, such as cell size and cell surface roughness. With the help of fluorescent labeling, additional cellular characteristics can also be evaluated such as the existence of a cellular nucleus, the amount of DNA inside the cell, antigens on a cellular membrane, and many other characteristics. As the cells are measured one by one, the total number of target cells detected can also be determined by counting the number of measured signal peaks. Additionally, some cytometry analyses also require measuring particle density in the sample, meaning the number of target particles per sample volume, which is also known as the absolute count in cytometry analyses. For this measurement, not only the total number of detected particles needs to be determined, but also the corresponding volume of the sample needs to be determined. These two pieces of information can be used together to calculate the number of particles per sample volume, e.g., the absolute count.

In conventional flow cytometry analyses, the sample preparation steps are usually carried out by manual operation. For example, the preparation steps are often performed in different containers, such as centrifugal tubes or vials, and only the final prepared sample is then loaded into a commercial cytometer for optical or other measurement. These manual steps of sample preparation require precise fluid handling by trained technicians, and are thus not suitable for applications where users are minimally trained.

Furthermore, for applications such as the point-of-care testing in medical diagnostics, the cytometry analyses are performed in a non-laboratory environment, such as in emergency rooms or physician offices. Therefore, it is important that the biological sample is self-contained and not exposed to environment causing biological contaminations. For this purpose, it is advantageous that both the sample preparation step and the measurement step are carried out in a self-contained manner such as inside a non-exposed container.

Additionally, the absolute count measurement requires that the total number of detected target cells and corresponding sample volume be known. In conventional cytometry analyses, a fixed amount of sample with a known volume is injected into the system to determine the absolute count. However, the fluidic system often introduces dead volumes, meaning that some portion of the sample does not go through the cytometer measurement. These dead volumes cause the real sample volume being measured to be different from the known volume being injected into the system, and therefore introduce inaccuracy to the absolute count.

With above considerations, there is a need to develop a fluidic cartridge that can perform the cytometry analysis in a self-contained, automated manner, including both the sample preparation and sample analysis steps. There is also a need that such a fluidic cartridge can perform not only a cytometry analysis and cell count, but also accurately measure the absolute count.

SUMMARY OF THE DISCLOSURE

The following embodiments and aspects thereof are described and illustrated in conjunction with devices, systems and methods which are meant to be exemplary and illustrative, not limiting in scope.

The present disclosure provides various fluidic cartridges and methods of using and making such fluidic cartridges. These fluidic cartridges can perform both the sample preparation and the cytometer analysis. These fluidic cartridges can be used for various types of cytometry analyses. In various embodiments, the fluidic cartridges as disclosed herein can be used to determine the absolute count. In various embodiments, the fluidic cartridges as disclosed herein can be used for DNA analysis of cell populations in tumor diagnosis. In various embodiments, the fluidic cartridges as disclosed herein can be used for CD4+/CD8+ lymphocyte subtype analyses in AIDS diagnosis. In various embodiments, the fluidic cartridges as disclosed herein can be used for cell analysis in complete blood count (CBC). These fluidic cartridges can also be used for other types of analyses including, but not limited to, analyzing analytes, proteins, enzymes, nucleic acids and other biological markers in samples.

Various embodiments of the present disclosure provide a device for analyzing target particles in a sample. In various embodiments, the device comprises a cartridge device. In various embodiments, the cartridge device comprises: an inlet configured for receiving the sample into the cartridge device; a fluidic structure fluidly connected to the inlet and configured for mixing at least a portion of the sample with at least a portion of a reagent to form one or more sample mixtures; a flow cell fluidly connected to the fluidic structure and configured for forming one or more sample streams from the one or more sample mixtures, wherein the sample streams are formed in the flow cell without a sheath flow, and wherein the flow cell comprises an optically transparent area configured for measuring an optical signal from the sample streams to detect the target particles in the sample; and a flow sensor fluidly connected to the flow cell and configured for measuring a sensing signal from the sample streams that enter the flow sensor. In various embodiments, a cartridge device as disclosed herein further comprises a reagent.

In various embodiments, a device as disclosed herein further comprises a reader instrument device, wherein the reader instrument device is configured for receiving, operating, and/or actuating the cartridge device. In various embodiments, the reader instrument device neither receives any liquid from the cartridge device nor transfers any liquid into the cartridge device.

Various embodiments of the present disclosure provide a method for analyzing target particles in a sample. The method comprises: applying the sample to a cartridge device as disclosed herein, which is configured for collecting a predetermined sample volume into the cartridge device; transferring the cartridge device into a reader instrument device as disclosed herein; mixing at least a portion of the collected sample and at least a portion of a reagent to form one or more sample mixtures inside the cartridge device; forming one or more sample streams from the one or more sample mixtures in a flow cell inside the cartridge device, wherein the sample streams are formed in the flow cell without a sheath flow; measuring an optical signal from the sample streams at the flow cell to detect the target particles in the sample streams; and using the reader instrument device to analyze the measured optical signal to quantify the target particles in the sample.

Various embodiments of the present disclosure provide a method for analyzing particles in a sample. The method comprises: applying the sample to a cartridge device as disclosed herein, which is configured for collecting a predetermined sample volume into the cartridge device; transferring the cartridge device into a reader instrument device as disclosed herein; mixing at least a portion of the collected sample and at least a portion of a reagent to form one or more sample mixtures inside the cartridge device; forming one or more sample streams from the one or more sample mixtures in a flow cell inside the cartridge device, wherein at least two separate sample mixtures are transferred into the same flow cell to form at least two separate sample streams without a sheath flow; measuring an optical signal from the sample streams at the flow cell to detect the target particles in the sample streams; and using the reader instrument device to analyze the measured optical signal to quantify the target particles in the sample.

In various embodiments, a method as disclosed herein further comprises: flowing the sample streams through a flow sensor that is fluidly connected to the flow cell; measuring a sensing signal from the sample streams at the flow sensor to detect the entrance of the sample streams into the flow sensor and/or the exit of the sample streams out of the flow sensor; and using the reader instrument device to analyze the measured optical signal and sensing signal to determine the concentration of the target particles in the sample.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 9A-9C illustrate, in accordance with various embodiments of the disclosure, one exemplary configuration of a cartridge device as disclosed herein, where a basic fluidic unit 9001, a sheathless flow cell 9007 and a flow sensor 9009 with two sensing zones 9011 and 9012 are connected in serial by fluidic conduits 9006 and 9008.

FIGS. 15A-15D illustrate, in accordance with various embodiments of the disclosure, the top view (in x-y plane) of a few examples of a flow cell as described herein.

FIGS. 16A-16B illustrate, in accordance with various embodiments of the disclosure, an example where a plurality of particles flow through a flow cell for detection.

DETAILED DESCRIPTION OF THE DISCLOSURE

Figure 1:
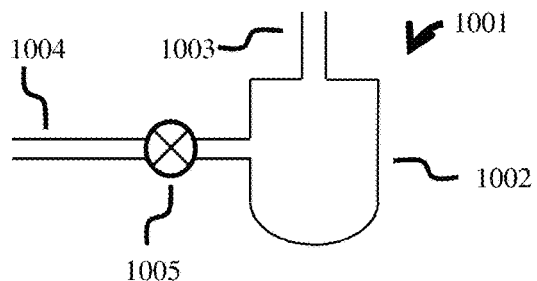
FIG. 1 illustrates, in accordance with various embodiments of the disclosure, one non-limiting example of the basic fluidic unit used in a cartridge device as disclosed herein.

All references cited herein are incorporated by reference in their entirety as though fully set forth. Unless defined otherwise, technical and scientific terms used herein have the same meaning as commonly understood by one of ordinary skill in the art to which this disclosure belongs. Tabelling, *Introduction to Microfluidics reprint edition*, Oxford University Press (2010); Hguyen et al., *Fundamentals and Applications of Microfluidics 2$^{nd}$ ed.*, Artech House Incorporated (2006); Berg et al., *Microfluidics for Medical Applications*, Royal Society of Chemistry (2014); Gomez et al., *Biological Applications of Microfluidics 1$^{st}$ ed.*, Wiley-Interscience (2008); and Colin et al., *Microfluidics 1$^{st}$ ed.*, Wiley-ISTE (2010), provide one skilled in the art with a general guide to many of the terms used in the present application.

One skilled in the art will recognize many methods and materials similar or equivalent to those described herein, which could be used in the practice of the present disclosure. Other features and advantages of the disclosure will become apparent from the following detailed description, taken in conjunction with the accompanying drawings, which illustrate, by way of example, various features of embodiments of the disclosure. Indeed, the present disclosure is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this disclosure belongs. It should be understood that this disclosure is not limited to the particular methodology, protocols, and reagents, etc., described herein and as such can vary. The definitions and terminology used herein are provided to aid in describing particular embodiments, and are not intended to limit the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

Various embodiments of the present disclosure provide a device for analyzing target particles in a sample. In various embodiments, the device comprises a cartridge device. In various embodiments, the cartridge device comprises: an inlet configured for receiving the sample into the cartridge device; a fluidic structure fluidly connected to the inlet and configured for mixing at least a portion of the sample with at least a portion of a reagent to form one or more sample mixtures; a flow cell fluidly connected to the fluidic structure and configured for forming one or more sample streams from the one or more sample mixtures, wherein the sample streams are formed in the flow cell without a sheath flow, and wherein the flow cell comprises an optically transparent area configured for measuring an optical signal from the sample streams to detect the target particles in the sample; and a flow sensor fluidly connected to the flow cell and configured for measuring a sensing signal from the sample streams that enter the flow sensor.

In various embodiments, the cartridge device has a size in the range of about $0.1\text{-}1\ cm^3$, $1\text{-}5\ cm^3$, $5\text{-}25\ cm^3$, $25\text{-}50\ cm^3$, or $50\text{-}200\ cm^3$.

In various embodiments, a device as disclosed herein further comprises a reader instrument device, wherein the reader instrument device is configured for receiving, operating, and/or actuating the cartridge device. In various embodiments, the reader instrument device is configured for measuring the optical signal at the flow cell to quantify the target particles in the sample. In various embodiments, the reader instrument device is configured for measuring the sensing signal at the flow sensor to quantify the volume of the sample streams. In various embodiments, the reader instrument device is configured for measuring the optical signal at the flow cell and the sensing signal at the flow sensor to determine the concentration of the target particles in the sample. In various embodiments, the reader instrument device comprises a control unit configured for measuring the optical signal at the flow cell. In various embodiments, the reader instrument device comprises a control unit configured for measuring the optical signal at the flow cell and the sensing signal at the flow sensor. In various embodiments, the reader instrument device neither receives any liquid from the cartridge device nor transfers any liquid into the cartridge device.

In various embodiments, a cartridge device as disclosed herein further comprises a reagent. In various embodiments, the reagent comprises a fluorescent labeling agent that selectively labels the target particles in the sample with fluorescence, and wherein the optical signal from the sample streams comprises fluorescence.

In various embodiments, a cartridge device as disclosed herein further comprises a first reagent, which is mixed with a portion of the received sample to form a first sample mixture, and a second reagent, which is mixed with another portion of the received sample to form a second sample mixture; and the two sample mixtures are separately transferred into the flow cell to form two separate sample streams. In various embodiments, the two sample mixtures are separately formed in a chamber or separately transferred into a chamber before being separately transferred into the flow cell. In various embodiments, the chamber has a volume in the range of about 0.01-0.1 ml, 0.1-0.2 ml, 0.2-0.4 ml, 0.4-0.8 ml, 0.8-2 ml, or 2-10 ml.

In various embodiments, a cartridge device as disclosed herein further comprises a fluidic conduit fluidly connected to the inlet and configured for receiving or collecting the sample. In various embodiments, the fluidic conduit is closed by a valve and/or sealed by an external structure after the sample is collected into the fluidic conduit. In accordance with various embodiments of the present disclosure, closing by the value and/or sealing by the external structure prevents the collected sample from exiting the cartridge device. In various embodiments, the fluidic conduit is configured for collecting a predetermine sample volume in the range of about 0.1-1 μL, 1-5 μL, 5-10 μL, 10-20 μL, or 20-50 μL. In various embodiments, at least a portion of the reagent is transferred into the fluidic conduit to flush a portion of the collected sample into a chamber to form a sample mixture.

In various embodiments, the sample, reagent, sample mixtures, or sample streams are enclosed inside the cartridge device to prevent or limit their exposure to the environment outside the cartridge. In various embodiments, the fluidic structure is inside the cartridge device to prevent or limit exposing the sample, reagent or sample mixtures to the environment outside the cartridge. In various embodiments, the flow cell is inside the cartridge device to prevent or limit exposing the sample streams to the environment outside the cartridge. In various embodiments, the flow sensor is inside the cartridge device to prevent or limit exposing the sample streams to the environment outside the cartridge.

In various embodiments, the fluidic structure comprises one or a plurality of fluidic conduits. In various embodiments, the fluidic structure comprises one or a plurality of chambers. In various embodiments, each chamber has a volume in the range of about 0.01-0.1 ml, 0.1-0.2 ml, 0.2-0.4 ml, 0.4-0.8 ml, 0.8-2 ml, or 2-10 ml. In certain embodiments, the fluidic structure comprises one or a plurality of chambers; each chamber has a volume in the range of about 0.01-0.1 ml, 0.1-0.2 ml, 0.2-0.4 ml, 0.4-0.8 ml, 0.8-2 ml, or 2-10 ml; and the fluidic structure is configured for transferring the sample mixtures from one of the chambers to the flow cell to form the sample streams.

In some embodiments, a cartridge device as disclosed here comprises one flow cell. In some embodiments, a cartridge device as disclosed comprises two, three, four, five, or more flow cells. In some embodiments, a cartridge device as disclosed comprises a plurality of flow cells.

In various embodiments, the flow cell is configured for allowing a flow rate in the range of 0.001-0.01, 0.01-0.1, 0.1-1, 1-50, 50-200, or 200-1000 μl/min. In various embodiments, the flow cell has a cross section in the shape of a rectangular, trapezoid, oval, circle, or half circle, or any other shape, or a combination thereof. In various embodiments, the flow cell has a width in the range of about 1-10 μm, 10-40 μm, 40-100 μm, or 100-200 μm. In various embodiments, the flow cell has a depth in the range of about 1-10 μm, 10-40 μm, 40-100 μm, or 100-200 μm. In various embodiments, the flow cell has a length in the range of about of 1-10 μm, 10-100 μm, 100-1,000 μm, 1,000-10,000 μm, or 10,000-50,000 μm. In various embodiments, the sample streams formed in the flow cell have a cross section of the same size as the flow cell.

In certain embodiments, the flow cell has a width in the range of about 1-10 μm, 10-40 μm, 40-100 μm, or 100-200 μm and a depth in the range of about 1-10 μm, 10-40 μm, 40-100 μm, or 100-200 μm; and the sample streams have a cross section of the same size as the flow cell.

In various embodiments, the optically transparent area on the flow cell has a transmission rate of 50-60%, 60-70%, 70-80%, 80-90%, 90-96%, or 96-99.9% for the optical signal from the sample streams. In various embodiments, the optical signal comprises scattered light, reflected light, transmitted light, fluorescence, light absorption, light extinction, or white light image, or a combination thereof. In certain embodiments, the optically transparent area on the flow cell has a transmission rate of 50-60%, 60-70%, 70-80%, 80-90%, 90-96%, or 96-99.9% for the optical signal from the sample streams, and the optical signal comprises scattered light, reflected light, transmitted light, fluorescence, light absorption, light extinction, or white light image, or a combination thereof.

In various embodiments, the optically transparent area on the flow cell is made of a plastic material. In various embodiments, the plastic material is cyclic olefin copolymer, cyclo-olefin polymer, poly-methyl methacrylate, polycarbonate, polystyrene, or poly-chloro-tri-fluoro-ethylene, or a combination thereof.

In various embodiments, the flow sensor comprises a fluidic channel and a sensing zone on the fluidic channel; the fluidic channel is fluidly connected to the flow cell to allow the sample streams to flow through; and a sensing signal is measured when the sample streams enter the sensing zone. In various embodiments, the sensing signal comprises an optical signal. In certain embodiments, the optical signal comprises light transmission through and/or light reflection from the sample streams.

In various embodiments, the fluidic channel in the flow sensor has a channel width in the range of about 0.001-0.05 mm, 0.05-1 mm, or 1-5 mm, and a channel depth in the range of about 0.001-0.01 mm, 0.01-0.5 mm, 0.5-1 mm, or 1-2 mm. In various embodiments, the flow cell and the flow sensor are configured to have the same flow rate for the sample streams flowing through. In various embodiments, the fluidic connection between the flow cell and the flow sensor is configured for a sample stream to have the same flow rate flowing through the flow cell and the flow sensor.

In various embodiments, the sensing zone comprises an optically transparent area configured for measuring an optical signal that changes levels between the absence and presence of the sample streams in the sensing zone. In various embodiments, the optically transparent area on the sensing zone has a transmission rate of 50-60%, 60-70%, 70-80%, 80-90%, 90-96%, or 96-99.9% for the optical signal from the sample streams. In various embodiments, the optical signal comprises scattered light, reflected light, transmitted light, fluorescence, light absorption, light extinction, or white light image, or a combination thereof. In various embodiments, the optically transparent area on the sensing zone is made of a plastic material. In various embodiments, the plastic material is cyclic olefin copolymer, cyclo-olefin polymer, poly-methyl methacrylate, polycarbonate, polystyrene, or poly-chloro-tri-fluoro-ethylene, or a combination thereof.

In some embodiments, the flow sensor comprises one sensing zone on the fluidic channel. In some embodiments, the flow sensor comprises two, three, four, five, or more sensing zones on the fluidic channel. In some embodiments, the flow sensor comprises a plurality of sensing zones on the fluidic channel.

In various embodiments, the fluidic structure comprises at least one basic fluidic unit that comprises: a chamber configured to accommodate a fluid; a venting port connected to the chamber, wherein the venting port is connected to a pneumatic pressure source, an ambient pressure, or the atmosphere pressure; a microfluidic channel connected to the chamber; and a valve on the microfluidic channel. In various embodiments, the cartridge device is configured for transferring the sample mixtures from the chamber into the flow cell to form the sample streams when an external actuation mechanism is applied to the cartridge device.

In various embodiments, the cartridge device is configured for transferring the sample mixtures from the chamber into the flow cell to form the sample streams when an external actuation mechanism is applied to the cartridge device. In various embodiments, the external actuation mechanism comprises a pneumatic pressure source. In various embodiments, the external actuation mechanism is configured for forming the sample streams with a flow rate in the range of 0.001-0.01, 0.01-0.1, 0.1-1, 1-50, 50-200, or 200-1000 μl/min. In certain embodiments, the cartridge device is configured for transferring the sample mixtures from the chamber into the flow cell to form the sample streams when an external actuation mechanism is applied to the cartridge device, and the external actuation mechanism comprises a pneumatic pressure source.

In various embodiments, the chamber of the basic fluidic unit has a volume in the range of about 0.01-0.1 ml, 0.1-0.2 ml, 0.2-0.4 ml, 0.4-0.8 ml, 0.8-2 ml, or 2-10 ml. In various embodiments, the microfluidic channel of the basic fluidic unit has a cross section of a size in the range of about 0.001-0.01 mm$^2$, 0.01-0.1 mm$^2$, 0.1-0.25 mm$^2$, 0.25-0.5 mm$^2$, 0.5-1 mm$^2$, 1-2 mm$^2$, or 2-10 mm$^2$. In certain embodiments, the chamber of the basic fluidic unit has a volume in the range of about 0.01-0.1 ml, 0.1-0.2 ml, 0.2-0.4 ml, 0.4-0.8 ml, 0.8-2 ml, or 2-10 ml, and the microfluidic channel of the basic fluidic unit has a cross section of a size in the range of about 0.001-0.01 mm$^2$, 0.01-0.1 mm$^2$, 0.1-0.25 mm$^2$, 0.25-0.5 mm$^2$, 0.5-1 mm$^2$, 1-2 mm$^2$, or 2-10 mm$^2$.

In various embodiments, when the cartridge device is in use, the chamber of the basic fluidic unit is so positioned that the at least a portion of the fluid inside the chamber is pulled by gravity towards the microfluidic channel and/or away from the venting port. In various embodiments, when the cartridge device is in use, the chamber of the basic fluidic unit has a volume larger than the volume of the fluid accommodated therein and an air gap exists between the venting port and the fluid accommodated therein.

In various embodiments, the valve of the basic fluidic unit is a passive valve that is configured for allowing a fluid flow to pass through the microfluidic channel when a pneumatic pressure is applied to the fluid flow and stopping the fluid flow when no pneumatic pressure is applied to the fluid flow. In various embodiments, the valve of the basic fluidic unit is a passive valve that comprises one of the following structures: (i) a channel with a hydrophilic inner surface embedded with a patch of a hydrophobic surface, (ii) a channel with a hydrophobic inner surface embedded with a patch of a hydrophilic surface, (iii) an enlargement of the channel cross section along the flow direction in a channel with a hydrophilic inner surface, and (iv) a contraction of the channel cross section along the flow direction in a channel with a hydrophobic inner surface. In various embodiments, the valve of the basic fluidic unit is an active valve operated by an actuation mechanism external to the cartridge device.

Various embodiments of the present disclosure provide a method for analyzing particles in a sample. The method comprises: providing a cartridge device as disclosed herein and a reader instrument device as disclosed herein; applying the sample to the cartridge device; transferring the cartridge device into the reader instrument device; operating the reader instrument device to actuate the cartridge device; and analyzing the target particles in the sample.

Various embodiments of the present disclosure provide a method for analyzing target particles in a sample. The method comprises: applying the sample to a cartridge device as disclosed herein, which is configured for collecting a predetermined sample volume into the cartridge device; transferring the cartridge device into a reader instrument device as disclosed herein; mixing at least a portion of the collected sample and at least a portion of a reagent to form one or more sample mixtures inside the cartridge device; forming one or more sample streams from the one or more sample mixtures in a flow cell inside the cartridge device, wherein the sample streams are formed in the flow cell without a sheath flow; measuring an optical signal from the sample streams at the flow cell to detect the target particles in the sample streams; and using the reader instrument device to analyze the measured optical signal to quantify the target particles in the sample.

Various embodiments of the present disclosure provide a method for analyzing target particles in a sample. The method comprises: applying the sample to a cartridge device as disclosed herein, which is configured for collecting a predetermined sample volume into the cartridge device; transferring the cartridge device into a reader instrument device as disclosed herein; mixing at least a portion of the collected sample and at least a portion of a reagent to form one or more sample mixtures inside the cartridge device; forming one or more sample streams from the one or more sample mixtures in a flow cell inside the cartridge device, wherein at least two separate sample mixtures are transferred into the same flow cell to form at least two separate sample streams without a sheath flow; measuring an optical signal from the sample streams at the flow cell to detect the target particles in the sample streams; and using the reader instrument device to analyze the measured optical signal to quantify the target particles in the sample.

In various embodiments, a portion of the collected sample is mixed with a first reagent to form a first sample mixture and another portion of the collected sample is mixed with a second reagent to form a second sample mixture; and the two sample mixtures are separately transferred into the flow cell to form two separate sample streams. In various embodiments, the two sample mixtures are separately formed in a chamber or separately transferred into a chamber before being separately transferred into the flow cell. In various embodiments, the chamber has a volume in the range of about 0.01-0.1 ml, 0.1-0.2 ml, 0.2-0.4 ml, 0.4-0.8 ml, 0.8-2 ml, or 2-10 ml.

In various embodiments, the sample is collected into a fluidic conduit. In various embodiments, the fluidic conduit is closed by a valve and/or sealed by an external structure after the sample is collected into the fluidic conduit. In accordance with various embodiments of the present disclosure, closing by the value and/or sealing by the external structure prevents the collected sample from exiting the cartridge device. In various embodiments, the fluidic conduit is configured for collecting a predetermine sample volume in the range of about 0.1-1 μL, 1-5 μL, 5-10 μL, 10-20 μL, or 20-50 μL. In various embodiments, at least a portion of the reagent is transferred into the fluidic conduit to flush a portion of the collected sample into a chamber to form a sample mixture.

In various embodiments, a method as disclosed herein further comprises: flowing the sample streams through a flow sensor that is fluidly connected to the flow cell; measuring a sensing signal from the sample streams at the flow sensor to detect the entrance of the sample streams into the flow sensor and/or the exit of the sample streams out of the flow sensor; and using the reader instrument device to analyze the measured optical signal and sensing signal to determine the concentration of the target particles in the sample.

In various embodiments, a method as disclosed herein further comprises: flowing the sample streams through a flow sensor that is fluidly connected to the flow cell; measuring a sensing signal from the sample streams at the flow sensor to detect the sample streams entering and/or exiting the flow sensor; and using the reader instrument device to analyze the measured optical signal and sensing signal to determine the concentration of the target particles in the sample. In various embodiments, the sample streams in the flow cell and the flow sensor have the same flow rate.

In various embodiments, a method as disclosed herein further comprises: flowing the sample streams through a flow sensor that is fluidly connected to the flow cell; measuring a sensing signal from the sample streams at the flow sensor to quantify the volume of the sample streams; and using the reader instrument device to analyze the measured optical signal and sensing signal to determine the concentration of the target particles in the sample. In various embodiments, the sample streams in the flow cell and the flow sensor have the same flow rate.

In various embodiments, the optical signal and sensing signal are measured by the reader instrument device.

In various embodiments, the collected sample, reagent, sample mixtures, or sample streams are enclosed inside the cartridge device to prevent or limit their exposure to the environment outside the cartridge.

In various embodiments, the mixing step is performed in a fluidic structure. In various embodiments, the fluidic structure comprises one or a plurality of fluidic conduits. In various embodiments, the fluidic structure comprises one or a plurality of chambers. In various embodiments, each chamber has a volume in the range of about 0.01-0.1 ml, 0.1-0.2 ml, 0.2-0.4 ml, 0.4-0.8 ml, 0.8-2 ml, or 2-10 ml. In certain embodiments, the mixing step is performed in a fluidic structure comprising one or a plurality of chambers, and each chamber has a volume in the range of about 0.01-0.1 ml, 0.1-0.2 ml, 0.2-0.4 ml, 0.4-0.8 ml, 0.8-2 ml, or 2-10 ml.

In various embodiments, the fluidic structure is inside the cartridge device to prevent or limit exposing the sample, reagent or sample mixtures to the environment outside the cartridge. In various embodiments, the flow cell is inside the cartridge device to prevent or limit exposing the sample streams to the environment outside the cartridge. In various embodiments, the flow sensor is inside the cartridge device to prevent or limit exposing the sample streams to the environment outside the cartridge.

In various embodiments, the flow cell has a width in the range of about 1-10 μm, 10-40 μm, 40-100 μm, or 100-200 μm. In various embodiments, the flow cell has a depth in the range of about 1-10 μm, 10-40 μm, 40-100 μm, or 100-200 μm. In various embodiments, the flow cell has a length in the range of about of 1-10 μm, 10-100 μm, 100-1,000 μm, 1,000-10,000 μm, or 10,000-50,000 μm. In various embodiments, the sample streams formed in the flow cell have a cross section of the same size as the flow cell.

In certain embodiments, the flow cell has a width in the range of about 1-10 μm, 10-40 μm, 40-100 μm, or 100-200 μm and a depth in the range of about 1-10 μm, 10-40 μm, 40-100 μm, or 100-200 μm; and the sample streams have a cross section of the same size as the flow cell.

In various embodiments, the sample streams in the flow cell have a flow rate in the range of 0.001-0.01, 0.01-0.1, 0.1-1, 1-50, 50-200, or 200-1000 μl/min when the optical signal is measured from the sample streams. In various embodiments, the optical signal measured from the sample streams at the flow cell comprises scattered light, reflected light, transmitted light, fluorescence, light absorption, light extinction, or white light image, or a combination thereof.

In various embodiments, the sample streams in the flow sensor have a flow rate in the range of 0.001-0.01, 0.01-0.1, 0.1-1, 1-50, 50-200, or 200-1000 μl/min when the sensing signal is measured from the sample streams. In various embodiments, the sensing signal measured from the sample streams at the flow sensor comprises an optical signal. In various embodiments, the optical signal comprises light transmission through and/or light reflection from the sample streams.

In various embodiments, the sample streams have the same flow rate in the flow cell and the flow sensor.

In various embodiments, the reagent comprises a fluorescent labeling agent that selectively labels the target particles in the sample with fluorescence, and wherein the optical signal from the sample streams comprises fluorescence.

In various embodiments, each of the sample streams is separately formed and measured in the flow cell. In various embodiments, at least two separate sample mixtures are transferred into the same flow cell to form at least two separate sample streams. In some embodiments, the at least two separate sample streams are formed consecutively (i.e., immediately one after another). In other embodiments, the at least two separate sample streams are formed nonconsecutively (i.e., not immediately one after another). In various embodiments, at least one sample stream comprises white blood cells as the target particles detected in the flow cell and at least another sample stream comprises red blood cells and/or platelet cells as the target particles detected in the flow cell.

In various embodiments, the fluidic channel in the flow sensor has a channel width in the range of about 0.001-0.05 mm, 0.05-1 mm, or 1-5 mm, and a channel depth in the range of about 0.001-0.01 mm, 0.01-0.5 mm, 0.5-1 mm, or 1-2 mm; and wherein the sample streams in the flow cell and the flow sensor have the same flow rate.

In certain embodiments, mixing is performed in at least one basic fluidic unit that comprises: a chamber configured to accommodate a fluid; a venting port connected to the chamber, wherein the venting port is connected to a pneumatic pressure source, an ambient pressure, or the atmosphere pressure; a microfluidic channel connected to the chamber; and a valve on the microfluidic channel. In various embodiments, the chamber of the basic fluidic unit has a volume in the range of about 0.01-0.1 ml, 0.1-0.2 ml, 0.2-0.4 ml, 0.4-0.8 ml, 0.8-2 ml, or 2-10 ml. In various embodiments, the microfluidic channel of the basic fluidic unit has a cross section of a size in the range of about 0.001-0.01 mm$^2$, 0.01-0.1 mm$^2$, 0.1-0.25 mm$^2$, 0.25-0.5 mm$^2$, 0.5-1 mm$^2$, 1-2 mm$^2$, or 2-10 mm$^2$.

In certain embodiments, mixing is performed in at least one basic fluidic unit that comprises: a chamber configured to accommodate a fluid, wherein the chamber has a volume in the range of about 0.01-0.1 ml, 0.1-0.2 ml, 0.2-0.4 ml, 0.4-0.8 ml, 0.8-2 ml, or 2-10 ml; a venting port connected to the chamber, wherein the venting port is connected to a pneumatic pressure source, an ambient pressure, or the atmosphere pressure; a microfluidic channel connected to the chamber, wherein the microfluidic channel has a cross section of a size in the range of about 0.001-0.01 mm$^2$, 0.01-0.1 mm$^2$, 0.1-0.25 mm$^2$, 0.25-0.5 mm$^2$, 0.5-1 mm$^2$, 1-2 mm$^2$, or 2-10 mm$^2$; and a valve on the microfluidic channel.

In various embodiments, the sample mixtures are transferred from the chamber into the flow cell to form the sample streams when an external actuation mechanism is applied to the cartridge device. In various embodiments, the external actuation mechanism comprises a pneumatic pressure source. In various embodiments, the external actuation mechanism is configured for forming the sample streams with a flow rate in the range of 0.001-0.01, 0.01-0.1, 0.1-1, 1-50, 50-200, or 200-1000 µl/min. In certain embodiments, the sample mixtures are transferred from the chamber into the flow cell to form the sample streams when an external actuation mechanism is applied to the cartridge device, and the external actuation mechanism comprises a pneumatic pressure source.

In various embodiments, the target particles have a size in the range of 0.1-1 µm, 1-10 µm, 10-15 µm, 15-30 µm, 30-50 µm, or 50-100 µm. In various embodiments, the target particles have a concentration in the range of 1-100, 100-1000, 1000-5000, 5000-20,000, or 20,000-50,000 target particles per µl sample steam. In certain embodiments, the target particles have a size in the range of 0.1-1 µm, 1-10 µm, 10-15 µm, 15-30 µm, 30-50 µm, or 50-100 µm; and the target particles have a concentration in the range of 1-100, 100-1000, 1000-5000, 5000-20,000, or 20,000-50,000 target particles per µl sample steam.

In various embodiments, the target particles comprise cells, plant cells, animal cells, blood cells, white blood cells, red blood cells, platelet cells, viruses, bacteria, fungi, yeasts, beads, fluorescent beads, or non-fluorescent beads; or other particles of proteins, enzymes, nucleic acids, polysaccharides, or polypeptides; or other particles bound with biological markers; or their combinations.

FIG. 1 illustrates one non-limiting example of the basic fluidic unit to be used in the cartridge. The basic fluidic unit 1001 has a chamber 1002, a venting port 1003 and at least one microfluidic channel 1004 that accesses the chamber and has a valve 1005 on the microfluidic channel. The operation of basic fluidic unit 1001 depends on gravity or any other force serving as the replacement for gravity (e.g., centrifugal force) to keep fluid in position. Additionally, the basic fluidic unit 1001 uses another force such as pneumatic pressure to transfer fluid. More information regarding the design, operation and manufacturing of fluid unit 1001 can be found in U.S. application Ser. No. 15/176,729 and PCT Application PCT/US16/36426, which are incorporated herein by reference in their entirety as if fully set forth. In some embodiments, the valve 1005 can be a passive valve. In other embodiments, the valve 1005 can be an active valve. In certain embodiments, the valve 1005 can be a hybrid or combination of passive and active valves. In other embodiments, the valve 1005 can be any design known to one of ordinary skill in the art.

Figure 2A:
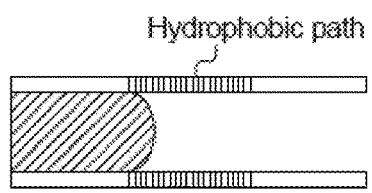
FIGS. 2A-2D illustrate, in accordance with various embodiments of the disclosure, a few non-limiting examples of passive valves.
Figure 2B:
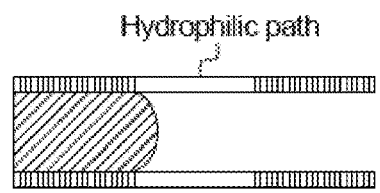
Figure 2C:
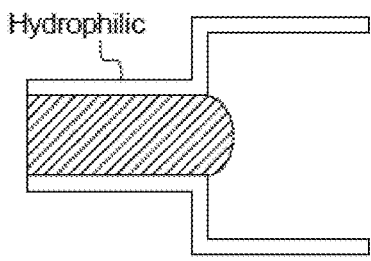
Figure 2D:
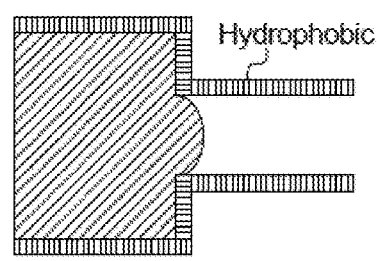

FIGS. 2A-2D illustrate a few non-limiting examples of passive valves. Other passive valve designs known to persons skilled in the art can also be used. FIG. 2A is a passive valve design having a channel with a hydrophilic inner surface and a patch of a hydrophobic surface. FIG. 2B is a passive valve design having a channel with a hydrophobic inner surface and a patch of a hydrophilic surface. FIG. 2C is a passive valve design having an enlargement of the channel cross-section along the flow direction and the channel has a hydrophilic surface. FIG. 2D is a passive valve design having a narrow down of the channel cross-section along the flow direction and the channel has a hydrophobic surface.

Figure 3A:
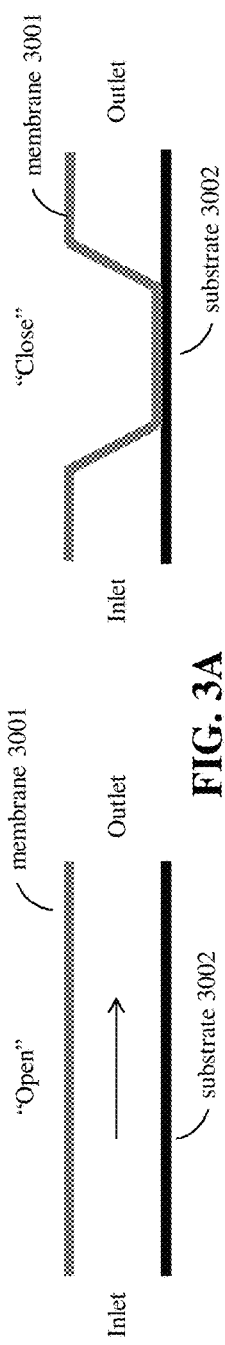
FIGS. 3A-3C illustrate, in accordance with various embodiments of the disclosure, a few non-limiting examples of active valves.
Figure 3B:
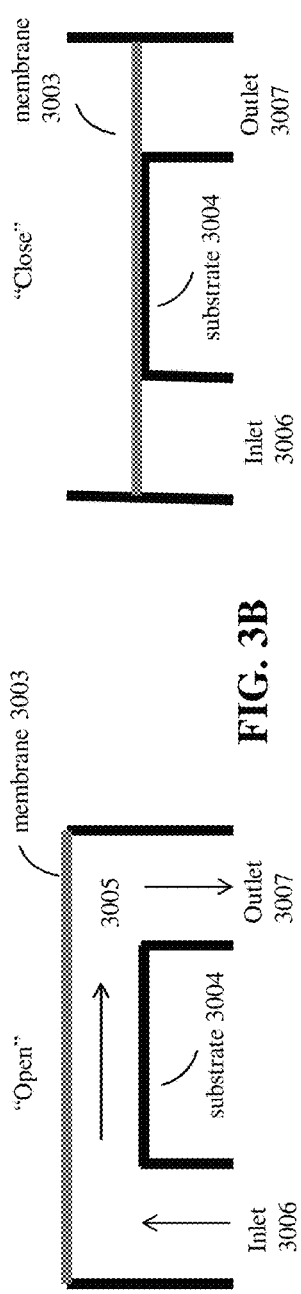
Figure 3C:
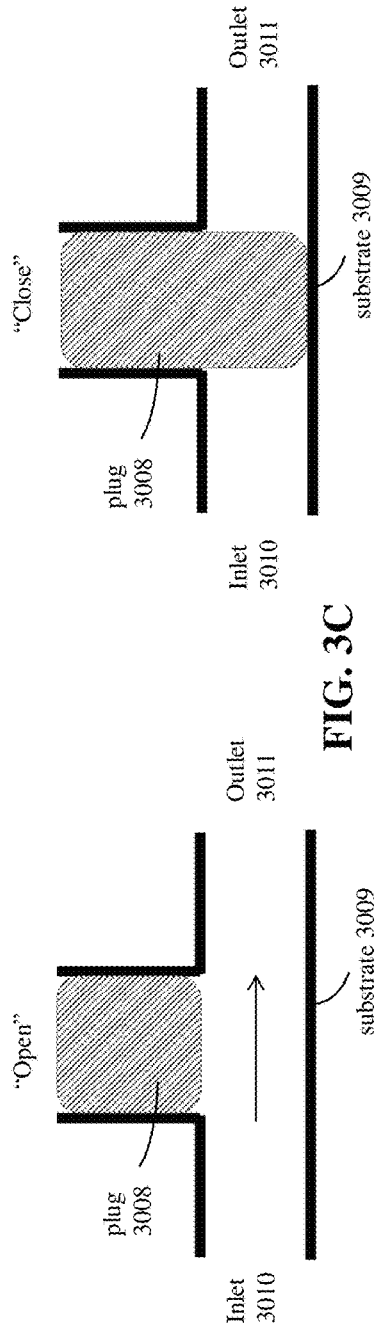

FIGS. 3A-3C illustrate a few non-limiting examples of active valves. Other active valve designs known to persons skilled in the art can also be used. FIG. 3A shows a valve design that includes a flexible membrane 3001 and a substrate 3002. When the flexible membrane 3001 is bent away from the substrate 3002, the valve is in an "open" status to allow fluid flow to pass through. When the flexible membrane 3001 is bent towards the substrate 3002 leaving no gap, the valve is in the "close" status and fluid flow is not able to pass through. FIG. 3B shows a valve design that has a movable membrane 3003 and a substrate 3004. When the movable membrane 3003 is away from the substrate 3004, there is a fluid path 3005 between the inlet and outlet, and the valve is in "open" status. When the movable membrane is in proximity with the substrate leaving no gap, there is no fluid path between the inlet 3006 and the outlet 3007, and the valve is in "close" status. FIG. 3C shows a valve design that has a plug 3008 on the channel. When the plug 3008 is pulled away from the channel leaving the substrate 3009, the channel is in the "open" status allowing fluid flow from the inlet 3010 to the outlet 3011. When the plug 3008 is inserted into the channel contacting the substrate 3009, the channel is in the "close" status and there is no fluid path between the inlet 3010 and the outlet 3011. The plug 3008 can be made of solid material, a polymer, an elastomer, a gel, a wax, a silicon oil or other materials. When an active valve is used, an additional actuation mechanism can be used to operate the valve.

Figure 4A:
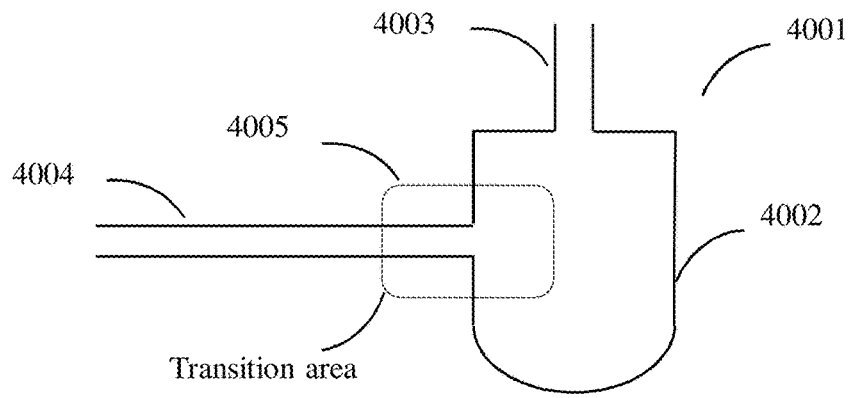
FIGS. 4A-4C illustrate, in accordance with various embodiments of the disclosure, one non-limiting example of implementing a passive valve in a basic fluidic unit.
Figure 4B:
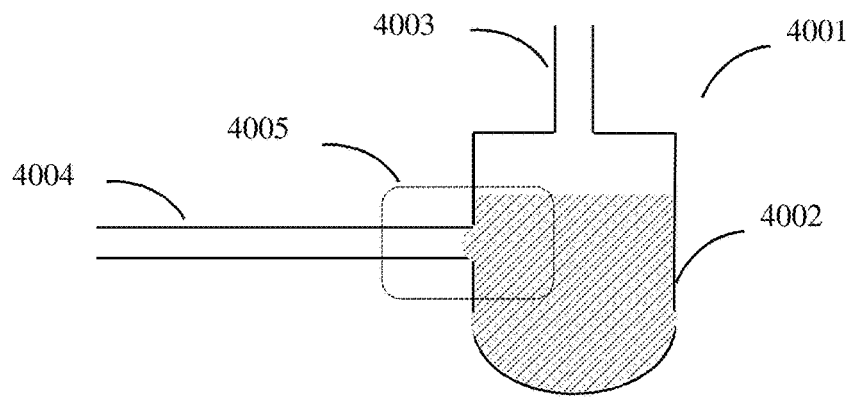
Figure 4C:
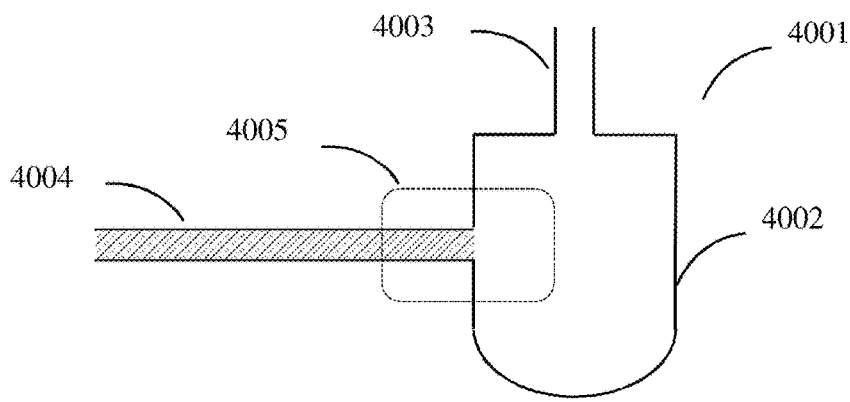

FIG. 4A illustrates another non-limiting example of implementing a passive valve in a basic fluidic unit 4001. In an embodiment, the transition area 4005 from the chamber 4002 to the channel 4004 provides a narrowing of the flow channel cross section. When both the channel inner surface and the chamber inner surface within this transition area 4005 are hydrophobic, as shown in FIG. 4B, this transition area 4005 is equivalent to the sudden narrow down of a hydrophobic channel, and acts as a passive valve to stop fluid in the chamber 4002 from entering the channel 4004. When both the channel inner surface and the chamber inner surface within this transition area 4005 are hydrophilic, as shown in FIG. 4C, this transition area is equivalent to the sudden enlargement of a hydrophobic channel, and acts as a passive valve to stop fluid in the channel 4004 from entering the chamber 4002. Additional designs of passive valves known to person skilled in the art can also be implemented.

Figure 5:
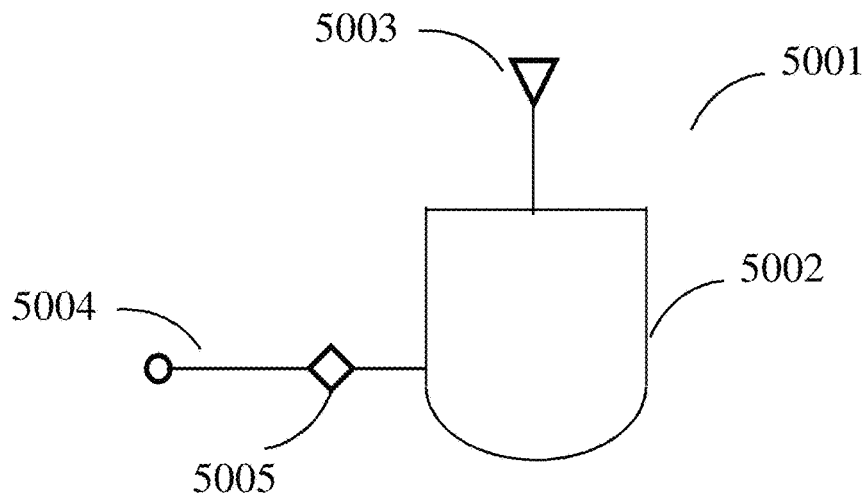
FIG. 5 illustrates, in accordance with various embodiments of the disclosure, a symbol drawing that represents a basic fluidic unit as described herein.

FIG. 5 illustrates a symbol drawing that represents a basic fluidic unit as described herein, where the basic fluidic unit 5001 includes a chamber 5002, a venting port 5003 and at least one microfluidic channel 5004 that accesses the chamber and has a valve 5005 on the microfluidic channel. The valve 5005 can be either a passive valve, an active valve or a hybrid or combination of both. In some embodiments, the basic fluidic unit 5001 can have one or a plurality of microfluidic channels (each having a valve) accessing the chamber 5002 (see, e.g., U.S. application Ser. No. 15/176, 729 and PCT Application PCT/US16/36426, which are incorporated herein by reference in their entirety as if fully set forth).

In various embodiments, present disclosure provides fluidic cartridges having at least one basic fluidic unit as described herein. In various embodiments, the fluidic cartridges may have additional fluidic structures. One example of additional fluidic structure is one or more flow cells for a cytometer analysis. With conventional flow cytometers, the flow cell usually has a core diameter of several hundreds of micrometers. To achieve a sample stream of a smaller core diameter, e.g., a few to dozens of micrometers, the flow cell utilizes sheath flow to focus the sample stream. In some embodiments, a fluidic cartridge as described herein includes a conventional flow cell with sheath flow.

Figure 6A:
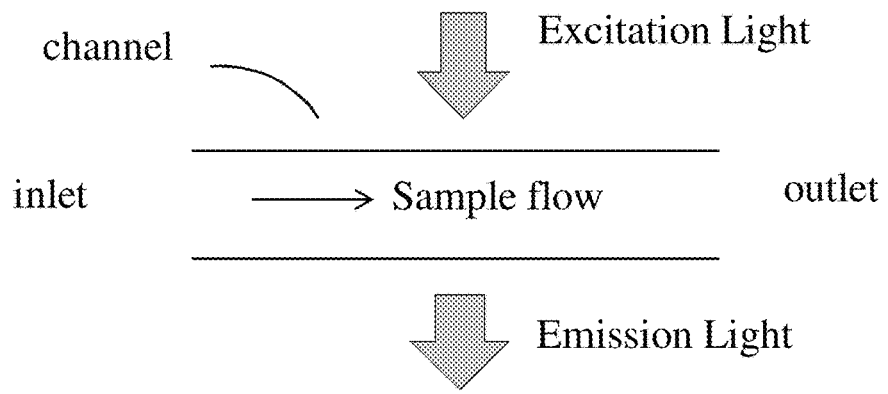
FIGS. 6A-6B illustrate, in accordance with various embodiments of the disclosure, one non-limiting example of a sheathless flow cell as described herein and its symbolic drawing.
Figure 6B:
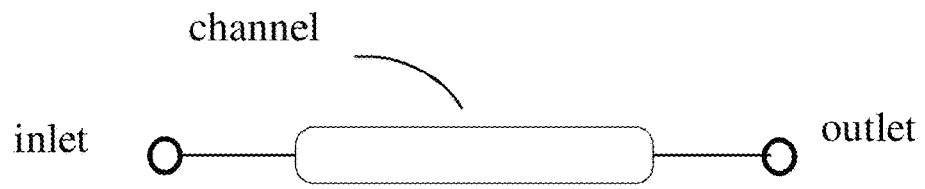

In other embodiments, a fluidic cartridge as described herein includes a sheathless flow cell instead of the conventional flow cell with sheath flow. The sheathless flow cell has a fluidic channel having a core diameter chosen according to the target sample stream diameter. For example, a fluidic channel having a diameter of 30 µm can be used to achieve a target sample stream having a diameter of 30 µm. Additionally, the channel of the flow cell can be transparent to certain excitation light and emission light wavelengths, so that optical signals can be measured from samples in the flow cell (FIG. 6A). FIG. 6B illustrates a symbolic drawing that represents a sheathless flow cell as described herein. Since the flow cell does not utilize sheath flow, the sample stream has a cross section in the same size as the flow cell.

Figure 7A:
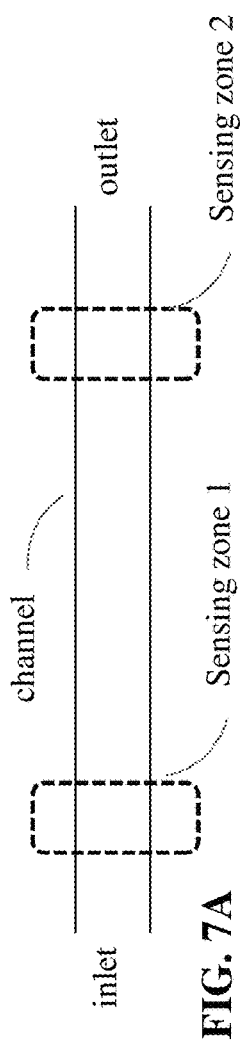
FIGS. 7A-7B illustrate, in accordance with various embodiments of the disclosure, one non-limiting example of a flow sensor as described herein, which has two sensing zones along the length of a fluidic channel, and its symbolic drawing.
Figure 7B:
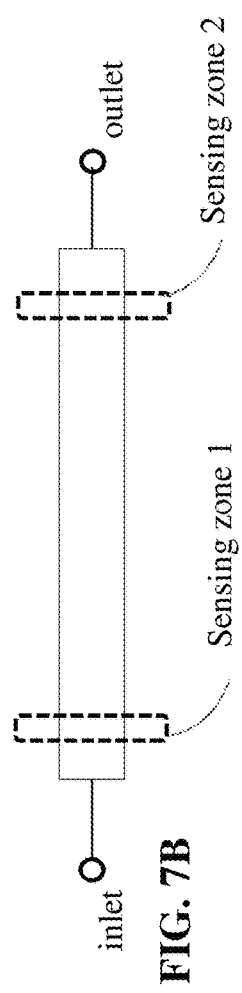
Figure 8A:
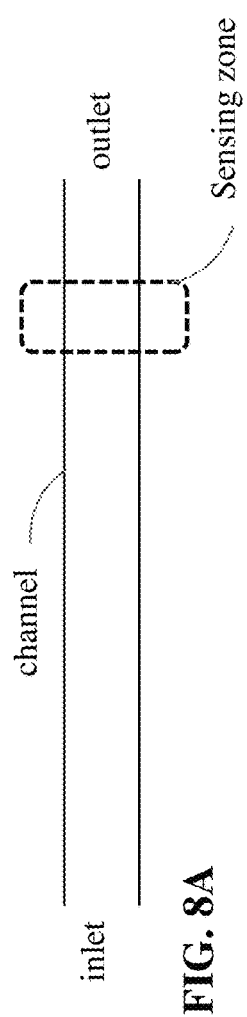
FIGS. 8A-8B illustrate, in accordance with various embodiments of the disclosure, another non-limiting example of a flow sensor as described herein, which has only one sensing zone along the length of a fluidic channel, and its symbolic drawing.
Figure 8B:
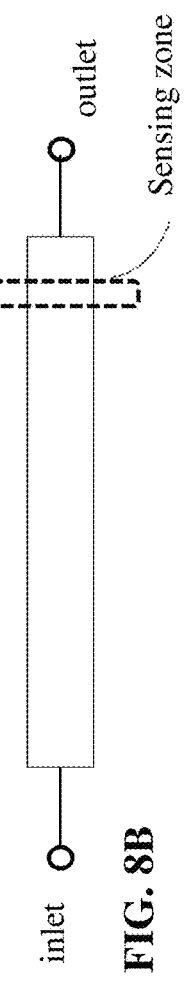

Another example of an additional fluidic structures is one or a plurality of flow sensors for detecting the sample stream. Described herein are the design and operation of such a flow sensor, which has one or a plurality of sensing zones on a channel to detect the existence of liquid in the channel and/or measure the fluid displacement volume, the volume of a fluidic plug, flow rate or flow velocity, etc. More information regarding the design, operation and manufacturing of the flow sensor can be found in U.S. application Ser. No. 15/209,226 and PCT Application PCT/US16/ 42089, which are incorporated herein by reference in their entirety as if fully set forth. FIG. 7A illustrates one non-limiting example of the flow sensor, which has two sensing zones along the length of a fluidic channel. The sensor detects whether there is fluid inside the channel overlapping with the sensing zones. The volume of fluid filling up the channel between the two sensing zones can be determined by the known geometry of the channel. FIG. 7B is a symbolic drawing to represent this design. FIG. 8A illustrates another non-limiting example of the flow sensor, which has only one sensing zone along the length of a fluidic channel. FIG. 8B is a symbolic drawing to represent this design.

Described herein are various fluidic units and additional fluidic structures that can be used together in various configurations to achieve functions of a flow cytometer analysis integrating sample preparation and performing absolute count in a self-contained cartridge.

FIG. 9A shows one exemplary configuration, where a basic fluidic unit 9001, a sheathless flow cell 9007 and a flow sensor 9009 with two sensing zones 9011 and 9012 are connected in serial by fluidic conduits 9006 and 9008. In some embodiments, the upstream end of the flow cell 9007 is connected to the microfluidic channel 9004 of the basic fluidic unit 9001, and the downstream end of the flow cell 9007 is connected with the flow sensor. In this particular configuration, sample in the chamber 9002 of the unit 9001 will pass through the flow cell first and then through the flow sensor for a cytometer analysis.

When using this configuration for a cytometer analysis, as shown in FIG. 9B, a fluid sample 9101 can first be loaded into the chamber 9002. Pneumatic pressures can then be applied to the vent 9003 of the basic fluidic unit 9001 and to the outlet port 9010 of the flow sensor. When the pneumatic pressure at vent 9003 is higher than the pneumatic pressure at port 9010, it creates a pressure difference that pumps sample 9101 from the chamber 9002 into the flow cell 9007 for the cytometer analysis, and then into the flow sensor 9009 for volume measurement. When the valve 9005 is a passive valve, a sufficiently-high pressure difference can pump the fluid sample to pass the valve 9005. When the valve 9005 is an active valve, the valve 9005 can be switched to open status before the pressure can pump the fluid sample 9101 to pass the valve 9005.

Figure 9C:
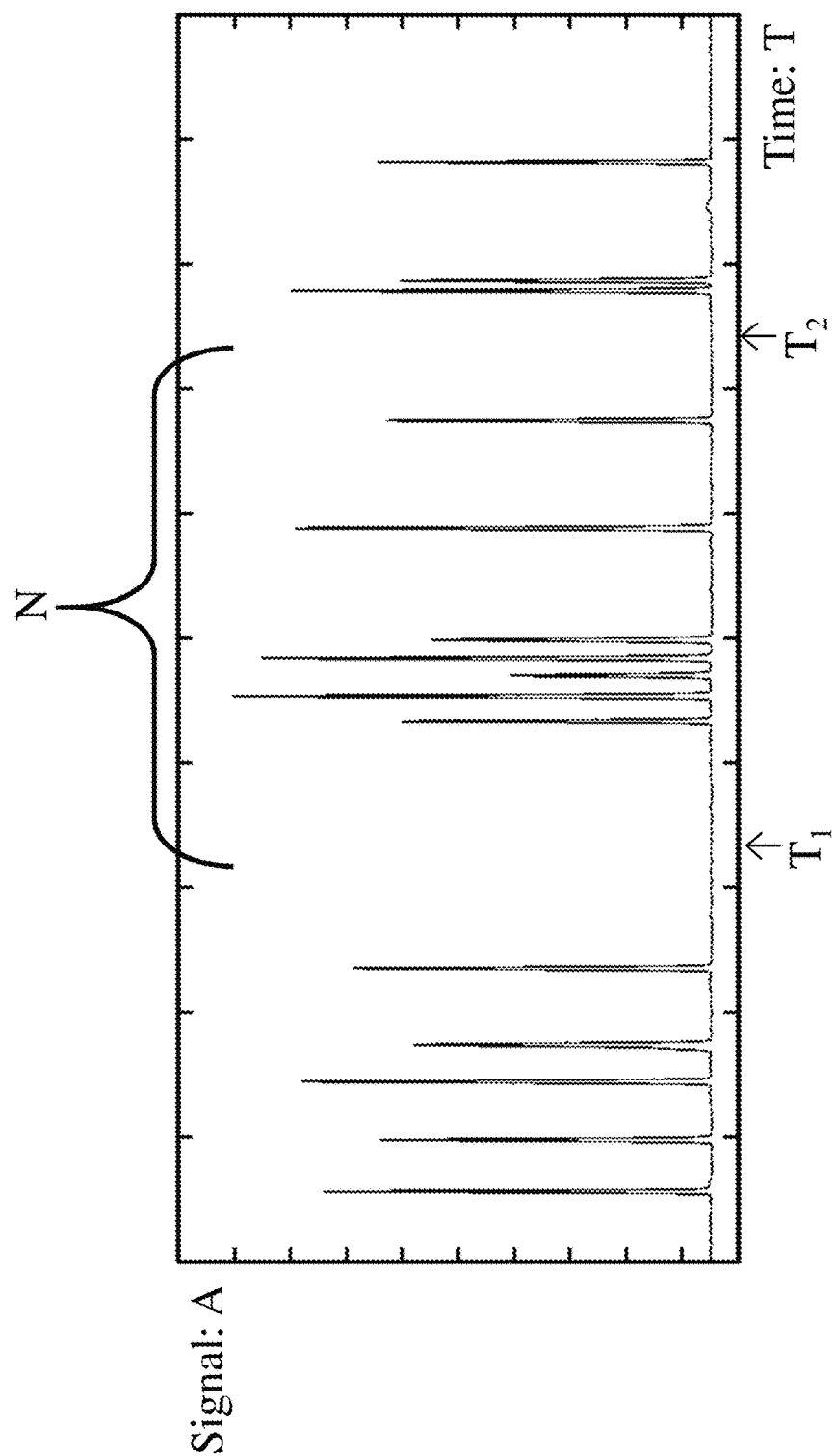

After applying the pneumatic pressures, data of the cytometer analysis in flow cell 9007 is continuously recorded. The recorded data includes the measured physical signal A (optical emission, electrical impedance, etc.) along time T as an array (A, T). FIG. 9C shows one example of the recorded data, where the amplitude of the signal A is plotted against the time T. The number of particles detected in the cytometer is determined by the number of peaks in the signal A. Meanwhile, as the sample continues to pass through the flow sensor 9009, the time point $T_1$ of the sample reaching the first sensing zone 9011 is recorded, and the time point $T_2$ of the sample reaching the second zone 9012 is also recorded. The number of particles N detected between T1 and T2 can be determined from the record signal (A, T) as shown in the example of FIG. 9C. The fluid volume $V_0$ for filling up the channel between the sensing zone 9011 and the sensing zone 9012 is a known parameter from the flow sensor design (see, e.g., U.S. application Ser. No. 15/209, 226 and PCT Application PCT/US16/42089, which are incorporated herein by reference in their entirety as if fully set forth). Because the sheathless flow cell contains only the fluid sample for analysis (no sheath flow), the fluid volume between the two sensing zones can be used to determine the volume of sample analyzed in the flow cell 9007. Therefore, the absolute count can then be calculated as:

$$\text{Absolute Count} = N/V_0 \quad [1]$$

In addition to the function of a cytometer analysis with absolute count, the example in FIGS. 9A-9C also has the feature that the whole fluidic structure can be implemented in a self-contained cartridge device. The cartridge device can be a molded piece of plastic with additional sealing layers.

Figure 10A:
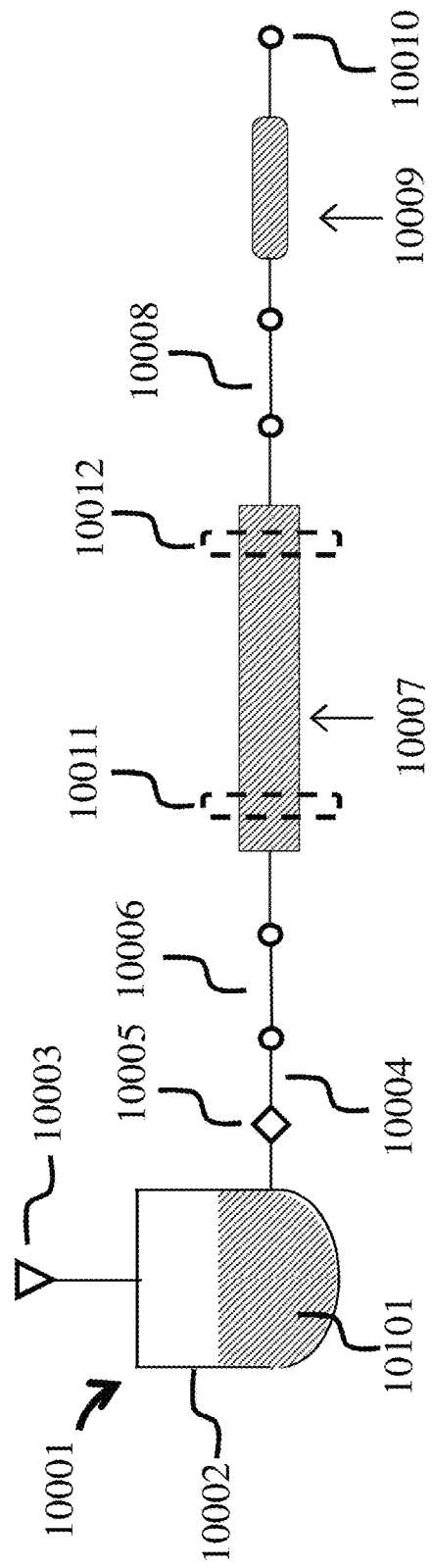
FIGS. 10A-10B illustrate, in accordance with various embodiments of the disclosure, another exemplary configuration of a cartridge device as disclosed herein, where a flow sensor 10007 is connected to the microfluidic channel 10004 of a basic fluidic unit 10001 with a fluidic conduit 10006.
Figure 10B:
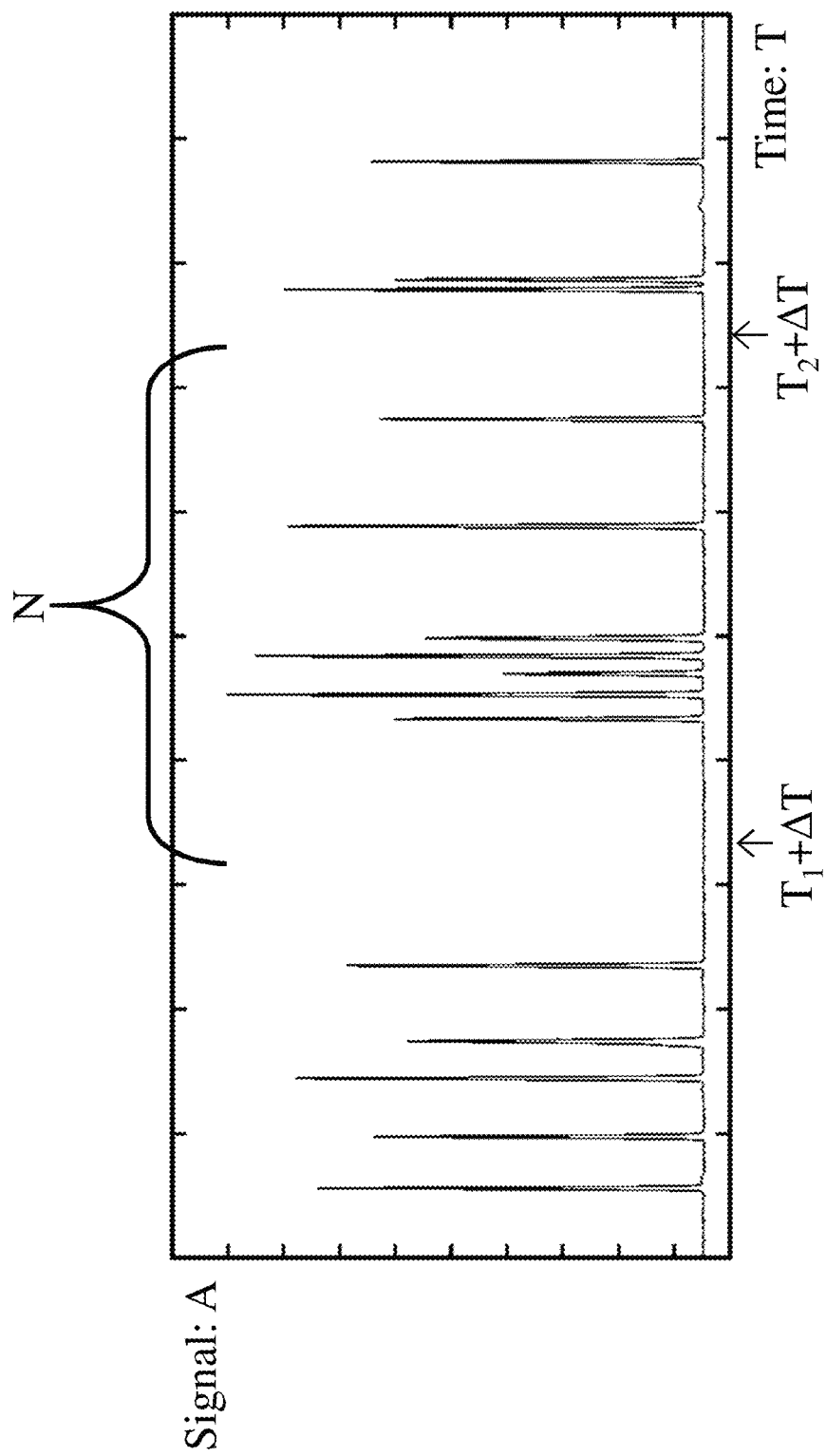

FIG. 10A shows another exemplary configuration, where a flow sensor 10007 is connected to the microfluidic channel 10004 of a basic fluidic unit 10001 with a fluidic conduit 10006. Meanwhile, a sheathless flow cell 10009 is connected downstream of the flow sensor 10007 by a fluidic conduit 10008. In this example, the number of cells counted N is determined by the signal (A, T) between time points $T_1+\Delta T$ and $T_2+\Delta T$, as shown in FIG. 10B, where $\Delta T$ can be any empirical value to compensate the time delay between the sample reaching the first sensing zone 10011 and sample reaching the flow cell 10009. Like the operation of FIG. 9A discussed above, the configuration of FIG. 10A can also be used for a cytometer analysis with absolute count:

$$\text{Absolute Count} = N/V_0 \quad [2]$$

Figure 11A:
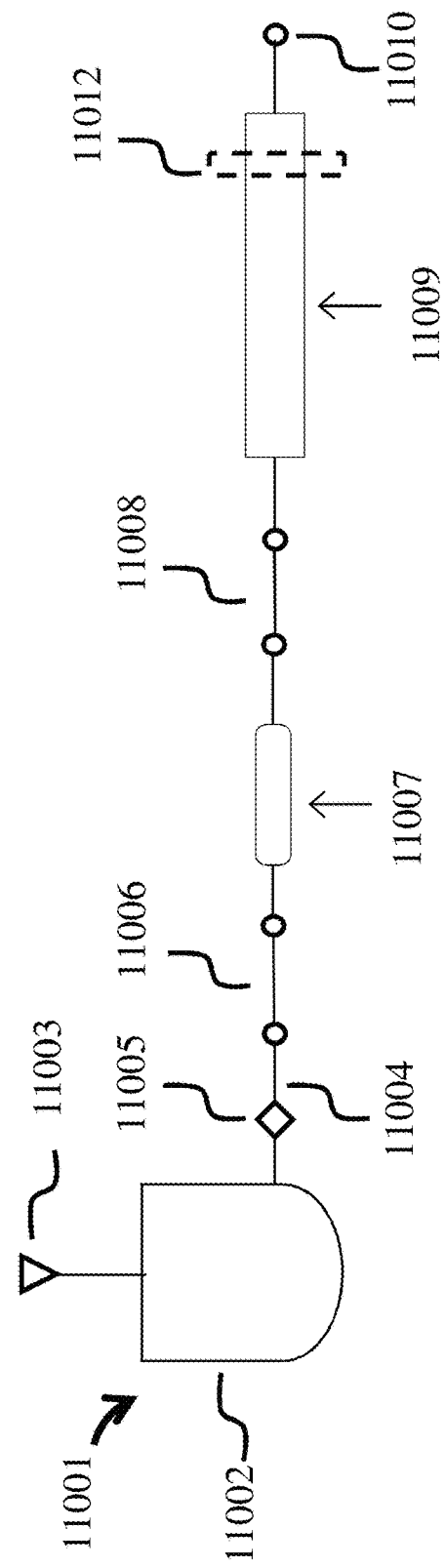
FIGS. 11A-11B illustrate, in accordance with various embodiments of the disclosure, another exemplary configuration of a cartridge device as disclosed herein, where a basic fluidic unit 11001, a sheathless flow cell 11007 and a flow sensor 11009 with one sensing zone 11012 are connected in serial by fluidic conduits 11006 and 11008.
Figure 11B:
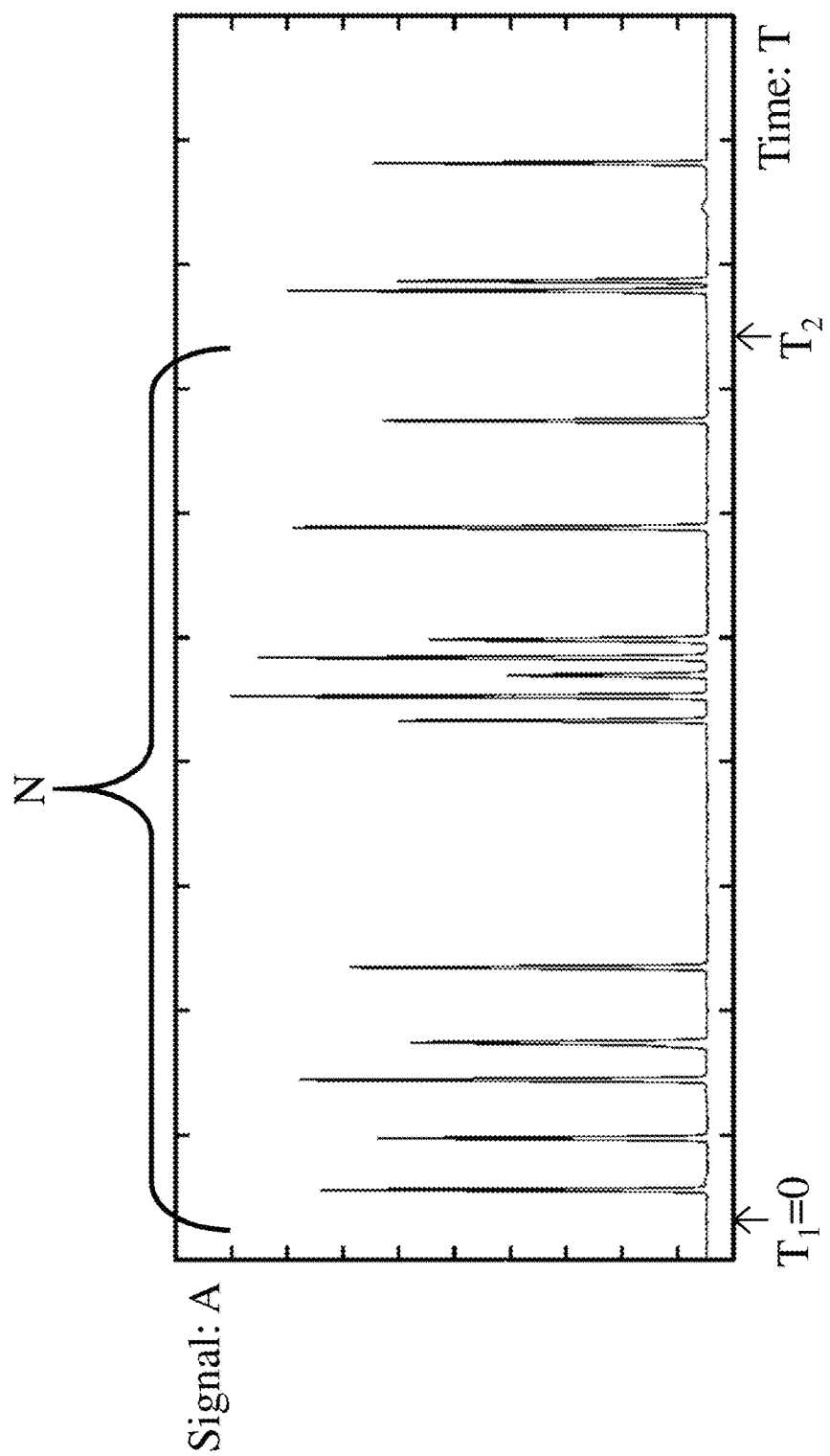

FIG. 11A shows another exemplary configuration, where a basic fluidic unit 11001, a sheathless flow cell 11007 and a flow sensor 11009 with one sensing zone 11012 are connected in serial by fluidic conduits 11006 and 11008. In some embodiments, the upstream end of the flow cell is connected to the microfluidic channel 11004 of the basic fluidic unit 11001, and the downstream end of the flow cell is connected to the flow sensor. In this exemplary configuration, sample in the chamber 11002 of the unit 11001 passes through the flow cell first and then through the flow sensor for a cytometer analysis. In this example, as shown in FIG. 11B, the time points $T_1=0$ (when the flow cell starts to detect particles) and $T_2$ (when the sample reaches the sensing zone 11012) are used to determine the total particle count N from the recorded signal (A, T). Additionally, the fluid volume $V_1$ to obtain the particle count N includes the total fluid conduit volume between the flow sensor 11007 and the sensing zone 11012 of the flow sensor 11009. The fluid volume $V_1$ is a parameter known from the fluidic design. Like the operation of FIG. 9 discussed above, the configuration of FIG. 10 can also be used for cytometer analysis with absolute count:

$$\text{Absolute Count} = N/V_1 \quad [3]$$

Figure 12A:
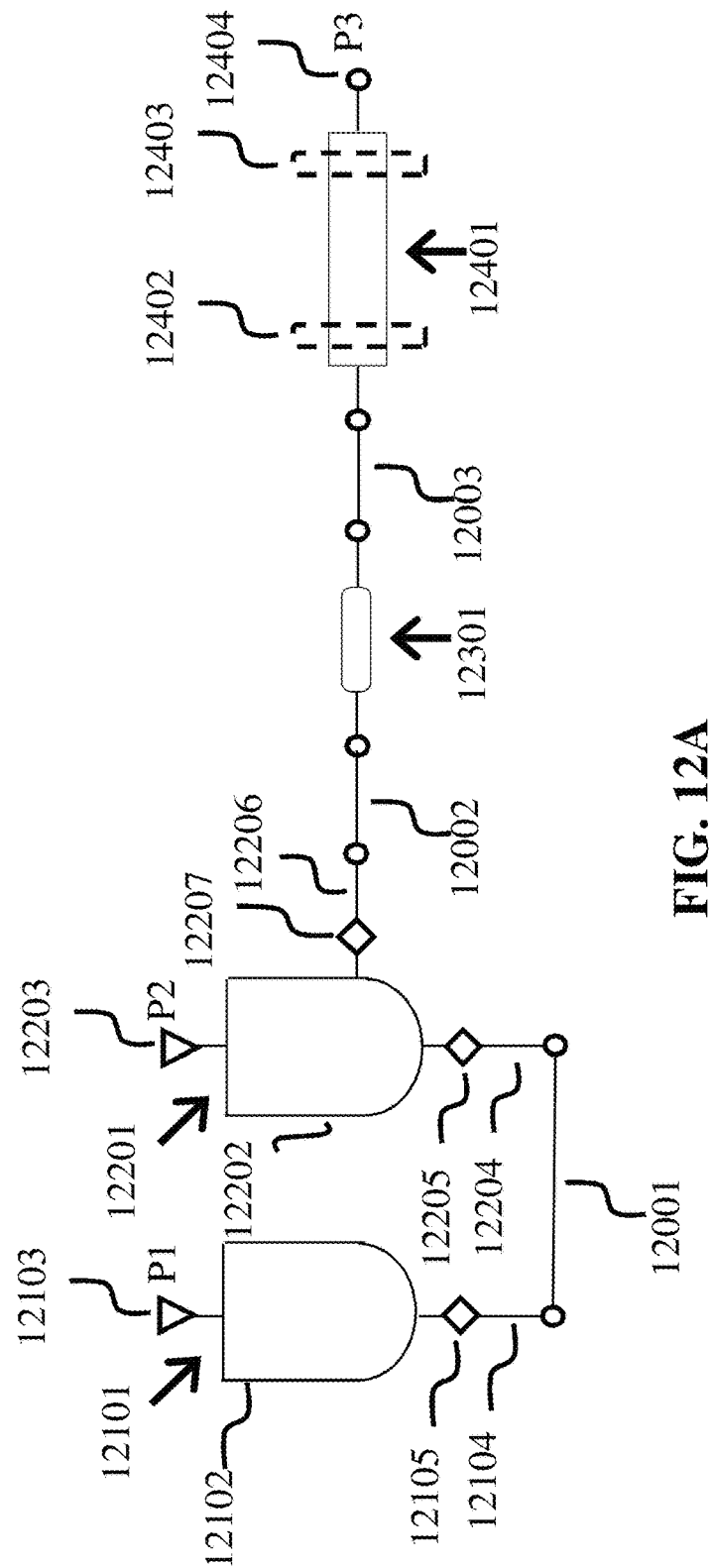
FIGS. 12A-12G illustrate, in accordance with various embodiments of the disclosure, another exemplary configuration of a cartridge device as disclosed herein, where two basic fluidic units 12101 and 12201 are used in serial with a sheathless flow cell 12301 and a flow sensor 12401.

FIG. 12A shows another exemplary configuration, where two basic fluidic units 12101 and 12201 are used in serial with a sheathless flow cell 12301 and a flow sensor 12401. A fluidic conduit 12001 connects the basic fluidic unit 12101's microfluidic channel 12104 (having a valve 12105) with the basic fluidic unit 12201's microfluidic channel 12204 (having a valve 12205). The unit 12201 has a second microfluidic channel 12206 (having a valve 12207), which connects to the upstream end of the flow cell 12301 by a fluid conduit 12002. The downstream end of the flow cell 12301 is further connected to the flow sensor 12401 by a fluid conduit 12003. In this example, the flow sensor 12401 has two sensing zones 12402 and 12403.

For a cytometer analysis, pneumatic pressures are applied to three ports, including the vent 12103 of unit 12101 ($P_1$), the vent 12203 ($P_2$) of unit 12201, and at the downstream port 12404 ($P_3$) of the flow sensor 12401. By controlling the applied pneumatic pressures ($P_1$, $P_2$, and $P_3$), a fluid sample can be transferred between the chamber 12102 and the chamber 12202, and further transferred into the flow cell for a cytometer analysis with the absolute count.

Figure 12B:
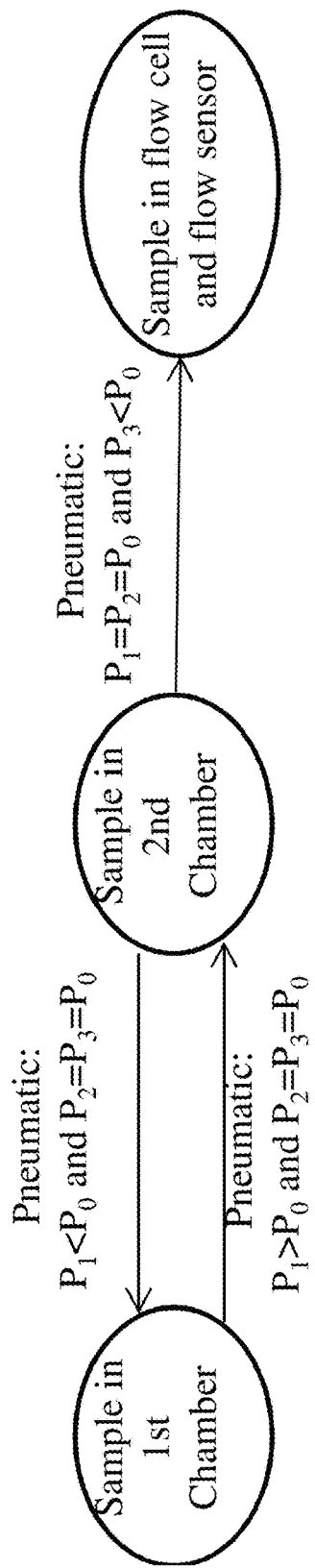

An exemplary method of controlling the pneumatic pressures ($P_1$, $P_2$ and $P_3$) and the corresponding fluid transfer is shown in the diagram of FIG. 12B. When a fluid sample is in the first chamber (chamber 12102), by applying a pneumatic control ($P_1>P_0$ and $P_2=P_3=P_0$), the fluid sample can be transferred from the first chamber into the second chamber (chamber 12202). Similarly, by applying a pneumatic control ($P_1<P_0$ and $P_2=P_3=P_0$), the fluid sample can be transferred from the second chamber into the first chamber. When the fluid sample is in the second chamber, by applying a pneumatic control ($P_1=P_2=P_0$ and $P_3<P_0$), the fluid sample can be transferred from the second chamber into the flow cell and the flow sensor for the cytometer analysis. In this exemplary pneumatic control method, the vent port of the second chamber $P_2$ is kept at a constant pressure $P_2=P_0$ during the operation. Following the teachings of this disclosure and the Applicants' previous disclosures (see, e.g., U.S. application Ser. No. 15/176,729 and PCT Application PCT/US16/36426, which are incorporated herein by reference in their entirety as if fully set forth), other methods can also be used to control the fluid transfer in the configuration. For example, by applying a pneumatic control ($P_1=P_2>P_0$ and $P_3=P_0$), the fluid sample in the second chamber can be transferred from the second chamber into the flow cell and the flow sensor for the cytometer analysis. In certain embodiments, $P_0$ is the atmosphere pressure where the fluidic configuration is operated in.

With the pneumatic control method, a sample can be transferred in the fluidic configuration for the cytometer analysis with absolute count. For example, a fluid sample can be initially introduced into the first chamber (chamber 12102). The sample can then be transferred to the second chamber (chamber 12202). The sample can then be driven through the flow cell and the flow sensor for the cytometer analysis with absolute count as described above. In another example, the fluid sample be can initially introduced into the second chamber and next driven through the flow cell and the flow sensor for the cytometer analysis with absolute count. In yet another example, a fluid sample A can be initially introduced into the first chamber and a fluid sample B can be initially introduced to the second chamber, and then the two samples can be transferred between the two chambers for a plurality of mixing cycles, before being delivered to the flow cell for the cytometer analysis with the absolute count. This mixing action involves the fluid sample moving along one direction from the first chamber into the second chamber and then along an opposite direction from the second chamber into the first chamber, and vice versa. In some embodiments, the fluid sample A has a predetermined volume. In certain embodiments, the fluid sample B has a predetermined volume.

In another embodiment, a fluid sample A can be initially introduced to the first chamber 12102 and a fluid sample C can be initially loaded in the fluid conduit 12001. By transferring the fluid sample between the two chambers, the fluid A and the fluid C can be mixed together, and then delivered to the flow cell for the cytometer analysis with the absolute count. The sample exiting the outlet of the flow sensor can be disposed or collected in a reservoir. In an embodiment where a reservoir is used to collect the exiting sample, the fluidic configuration of this example achieves the sample preparation, cytometer analysis and the absolute count function in a self-contained manner, without an exchange of fluid sample between the fluidic structure and the outside environment. Such an embodiment can be used for a cytometer analysis of different biological samples. For example, the fluid sample C can be a biological sample such as whole blood from human body. The fluid sample A can be a reagent containing a fluorophore-conjugated antibody targeting specific cell types, e.g. CD4+ lymphocytes, in the whole blood. By mixing these two fluids together and then measuring the mixture in the flow cell, it achieves the absolute count of the CD4+ Lymphocyte. In another example, the fluid sample C can be a human whole blood, whereas the fluid sample A can be a lysing solution selectively targeting Red Blood Cells (RBCs). After mixing the two fluids together and incubating the mixture for a period of time, the mixture is measured in the flow cell for a cytometer analysis such as the absolute count of the white blood cells (WBCs).

Figure 12C:
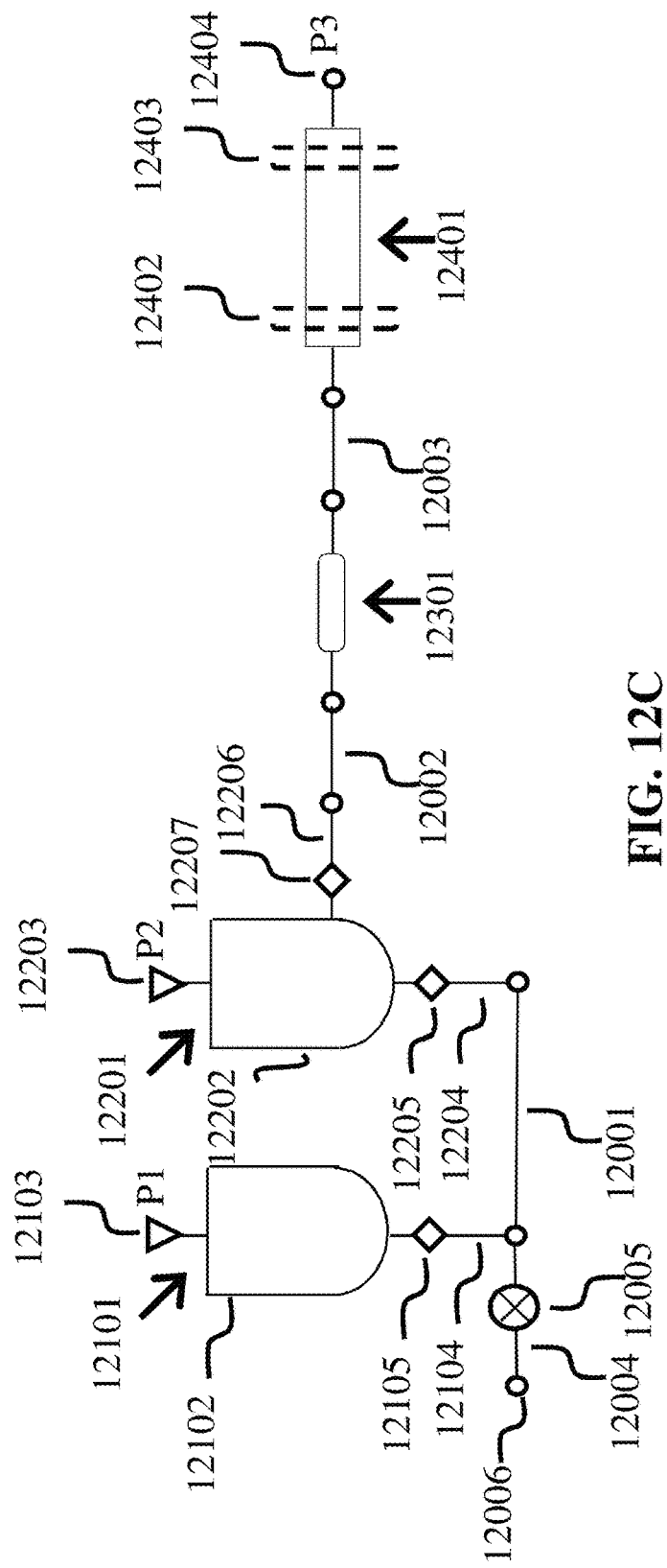

FIG. 12C shows an exemplary fluidic configuration, where an additional fluid conduit 12004 is connected to the fluid conduit 12001 to introduce the initial sample C. The sample can be introduced via the port 12006 into the fluidic conduit 12001. A valve 12005 can then be closed to seal the conduit 12004, preventing the sample from exiting the port 12006. In some embodiments, the fluid conduit 12001 can be used to collect a predetermined volume of the initial sample. In some embodiments, the valve 12005 can be a blood clotting valve (see, e.g., U.S. Pat. No. 8,845,979, which incorporated herein by reference in its entirety as if fully set forth). Other methods known to persons skilled in the art can also be used to introduce the initial samples.

In some embodiments, a reservoir chamber can be connected to outlet port of the flow sensor to collect the fluid sample after the cytometer analysis. As shown in the exemplary fluidic configuration of FIG. 12D, a reservoir 12501 with a venting port 12502 can be connected to the outlet port 12404 of the flow sensor by a fluidic conduit 12503. With this extra reservoir, the pneumatic pressure P3 can be adjusted by controlling the pneumatic pressure P4 at the venting port 12502 of the reservoir. An exemplary operation of this fluidic configuration is illustrated in FIG. 12E.

In other embodiments, additional fluidic structures can be connected to one or more of the basic fluidic units, achieving additional operation functionalities. FIG. 12F shows one example of these embodiments. In comparison to the example of FIG. 12A, the second basic fluidic unit 12201 has a third microfluidic channel 12208 (with a valve 12209), which connects by a fluidic conduit 12007 to a reservoir structure 12601 with a venting port 12602. The venting port 12602 corresponds to a pneumatic pressure P5. A fluid sample D is initially stored in the reservoir 12601. FIG. 12G shows a pneumatic control for operating this configuration. By applying a pneumatic control ($P_5>P_0$ and $P_2=P_0$), the sample D initially stored in the reservoir 12601 is transferred into the second chamber 12202. The rest of the pneumatic operation for the cytometer analysis can be the same as the example in the FIG. 12B.

Figure 13A:
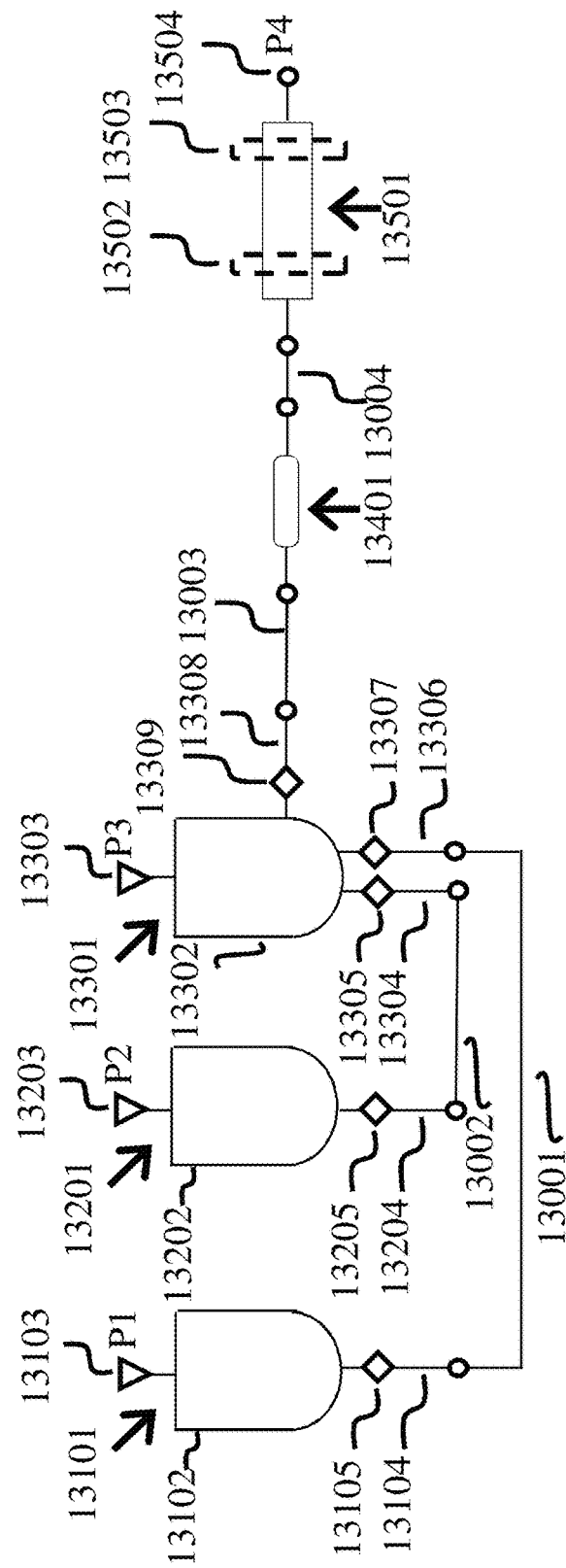
FIGS. 13A-13C illustrate, in accordance with various embodiments of the disclosure, another exemplary configuration of a cartridge device as disclosed herein, where three basic fluidic units 13101, 13201 and 13301 are used in serial with a sheathless flow cell 13401 and a flow sensor 13501.

In yet another exemplary configuration, as shown in FIG. 13A, there are three basic fluidic units 13101, 13201 and 13301. The units 13101 and 13201 have microfluidic channels 13104 (with the valve 13105) and 13204 (with the valve 13205), respectively. The unit 13301 has three microfluidic channels 13304 (with the valve 13305), 13306 (with the valve 13307) and 13308 (with the valve 13309). A fluidic conduit 13001 connects the channels 13104 and 13304, whereas another fluidic conduit 13002 connects the channel 13204 and 13306. The fluid unit 13302 is also connected to an upstream port of a sheathless flow cell 13401 by a fluidic conduit 13003, while the downstream port of the flow cell 13401 is connected to a flow sensor 13501 by a fluidic conduit 13004. This fluidic configuration is operated by controlling the pneumatic pressures at the venting ports of the basic fluidic units 13103 (P1), 13203 (P2) and 13303 (P3), and by controlling the pneumatic pressure of the outlet port 13504 of the flow sensor (P4).

Figure 13B:
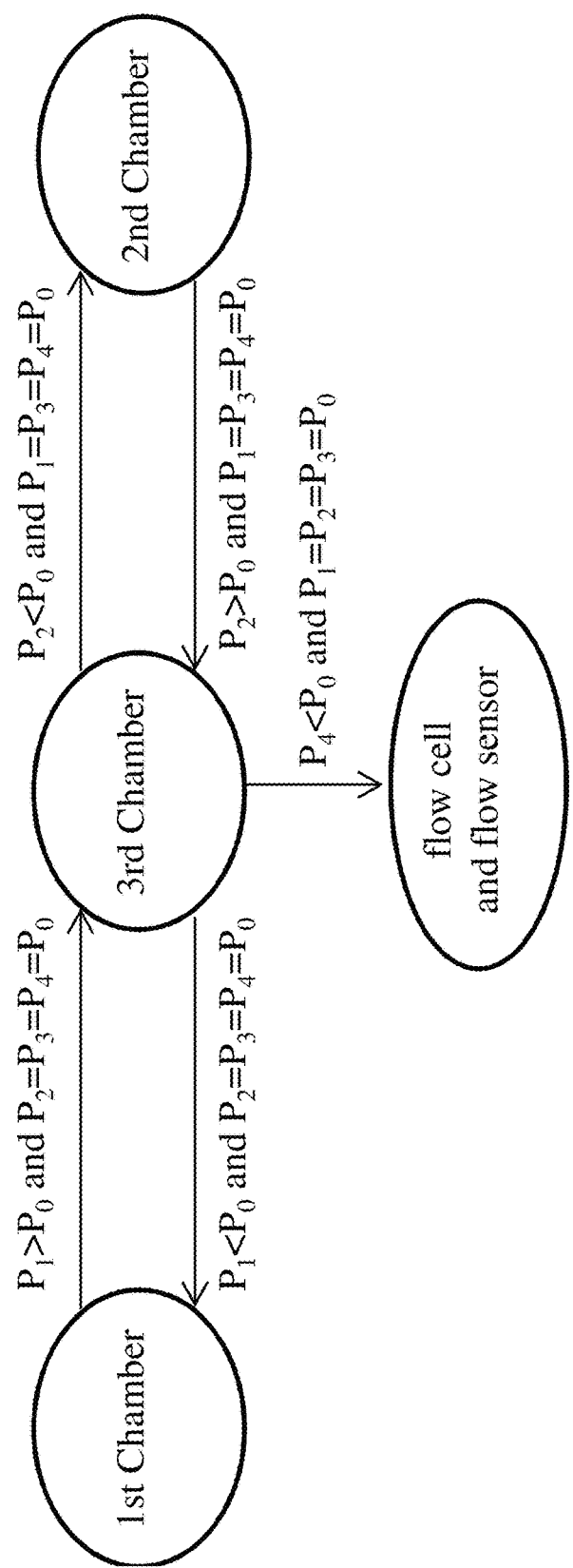

An exemplary method of controlling the pneumatic pressures ($P_1$, $P_2$, $P_3$ and $P_4$) and the corresponding fluid transfer is shown in the diagram of FIG. 13B. A fluid sample in the first chamber (13102) can be transferred into the third chamber (13302) by applying a pneumatic control ($P_1>P_0$ and $P_2=P_3=P_4=P_0$), whereas a fluid sample in the third chamber can be transferred into the first chamber by applying a pneumatic control ($P_1<P_0$ and $P_2=P_3=P_4=P_0$). Similarly, a fluid sample in the second chamber (13202) can be transferred into the third chamber by applying a pneumatic control ($P_2>P_0$ and $P_1=P_3=P_4=P_0$), whereas a fluid sample in the third chamber can be transferred into the second chamber by applying a pneumatic control ($P_2<P_0$ and $P_1=P_3=P_4=P_0$). Meanwhile, a fluid sample in the third chamber can be transferred into the flow cell and the flow sensor for the cytometer analysis, by applying a pneumatic control ($P_4<P_0$ and $P_1=P_2=P_3=P_0$). In this exemplary pneumatic control method, the vent port of the third chamber $P_3$ is kept at a constant pressure $P_3=P_0$ during the operations. Following the teachings of this disclosure and Applicants' previous disclosures (see, e.g., U.S. application Ser. No. 15/176,729 and PCT Application PCT/US16/36426, which are incorporated herein by reference in their entirety as if fully set forth), other methods can also be used to control the fluid transfer in this configuration.

Figure 13C:
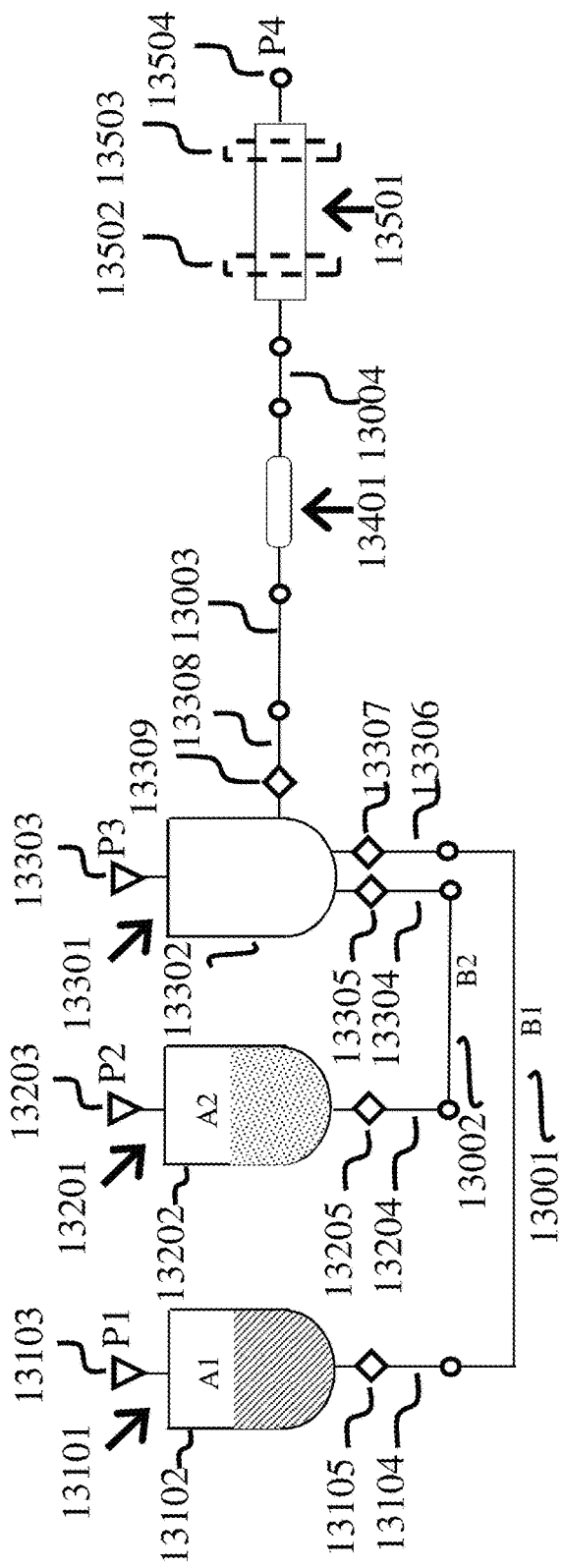

This fluidic configuration and the fluid transfer diagram can be used to perform more complex sample preparation and cytometer analysis. For example, as shown in FIG. 13C, a fluid sample A1 is initially introduced into the first chamber and a fluid sample A2 is initially introduced into the second chamber. Meanwhile, fluid samples B1 and B2 are each introduced into the fluidic conduit 13001 and 13002, respectively. By applying the pneumatic control ($P_1>P_0$ and $P_2=P_3=P_4=P_0$), the fluid samples A1 and B1 are transferred into the third chamber. By applying the pneumatic control ($P_4<P_0$ and $P_1=P_2=P_3=P_0$), the sample mixture of A1 and B1 is transferred into the sheathless flow cell and the flow sensor for the cytometer analysis with the absolute count. After the cytometer analysis, if any residue of the sample mixture is left behind in the third chamber, it can be transferred back into the first chamber by applying pneumatic control ($P_1<P_0$ and $P_2=P_3=P_4=P_0$) and thus make the third chamber empty to be ready for analysis of other samples. Prior to the cytometer analysis, if mixing uniformity of the sample mixture is a design consideration, the pneumatic control ($P_1<P_0$ and $P_2=P_3=P_4=P_0$) and ($P_1>P_0$ and $P_2=P_3=P_4=P_0$) can be applied in sequential to move the mixture from the third chamber into the first chamber, and then from the first chamber back into the third chamber again, introducing a mixing action of the sample. This step can be repeated to achieve desirable mixing uniformity. During these steps of fluid transfer, the fluid samples A2 and B2 do not move. This is achieved by keeping the pneumatic pressure ($P_2=P_3$). Next, the fluid samples A2 and B2 can be transferred into the third chamber by applying the pneumatic control ($P_2>P_0$ and $P_1=P_3=P_4=P_0$). The mixture of the samples A2 and B2 can be next transferred into the flow cell for the cytometer by applying the pneumatic control ($P_4<P_0$ and $P_1=P_2=P_3=P_0$). If mixing uniformity is desirable, steps of repeated transfer between the second chamber and the third chamber can also be carried out similar to the repeated transfer steps between the first and the third chamber. In certain embodiments, the fluid sample A1 has a predetermined volume. In certain embodiments, the fluid sample A2 has predetermined volume. In certain embodiments, the fluid sample B1 has predetermined volume. In certain embodiments, the fluid sample B2 has predetermined volume.

This fluid configuration and the fluid transfer diagram can be used to implement a cytometer analysis of various biological samples. For example, the fluid sample A1 can be a dilution buffer for RBC analysis and the sample B1 can be whole blood, whereas the sample A2 can be a lysing buffer for WBC analysis and the sample B2 can be whole blood. A1 and B1 can be transferred into the third chamber to form a mixture, and then into the flow cell for counting and analyzing of RBCs and platelets in the blood. A2 and B2 can then be transferred into the third chamber to form a mixture, and then into the flow cell for counting and analyzing WBCs in the blood. Different dilution buffers and lysing buffers known to persons skilled in the art of hematology analyzers can be used. In this way, the fluid configuration can be used to achieve the Complete Blood Count (CBC) analysis widely used in clinical tests.

FIGS. 12A-12G and FIGS. 13A-13C show examples having two and three basic fluidic units, respectively. In other embodiments, more basic fluidic units can be used in the configuration to achieve additional complexity. In the examples of FIGS. 12A-12G and FIGS. 13A-13C, the fluidic conduits for connecting the basic fluidic units (e.g. the fluid conduit 12001, the fluid conduit 13001 and the fluid conduit 13002) are fluid channels. In other embodiments, fluid structures with additional complexity can be used as the fluidic conduits.

Figure 14A:
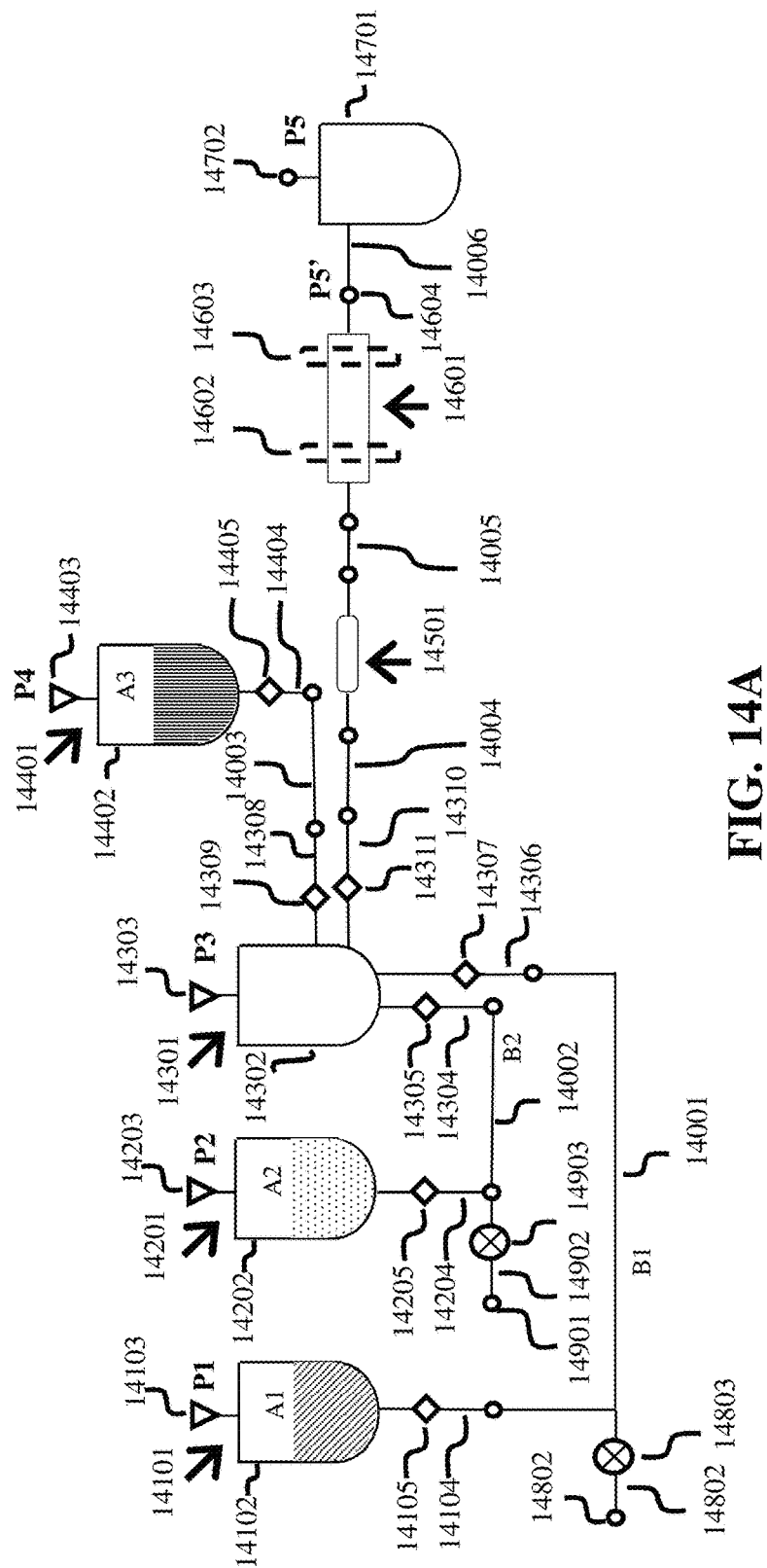
FIGS. 14A-14B illustrate, in accordance with various embodiments of the disclosure, another exemplary configuration of a cartridge device as disclosed herein, where four basic fluidic units 14101, 14201, 14301 and 14401 are used in serial with a sheathless flow cell 14501 and a flow sensor 14601.

FIG. 14A shows an example with four basic fluidic units, 14101, 14201, 14301 and 14401. Each of the four units 14010, 14201 and 14401 has a microfluidic channel with a valve. The unit 14301 has four microfluidic channels including channel 14304 (with valve 14305), channel 14306 (with valve 14307), channel 14308 (with valve 14309), and channel 14310 (with valve 14311). The basic fluidic unit 14101 is connected to the basic fluidic unit 14301 by a fluidic conduit 14001. The basic fluidic unit 14201 is connected to the basic fluidic unit 14301 by a fluidic conduit 14002. The basic fluidic unit 14401 is connected to the basic fluidic unit 14301 by a fluidic conduit 14003. The upstream of a sheathless flow cell 14501 is connected to the basic fluidic unit 14301 by a fluidic conduit 14004, while the downstream of the flow cell 14501 is connected by a fluidic conduit 14005 to a flow sensor 14601 that has two sensing zones 14602 and 14603. The flow sensor 14601 is then connected to a reservoir chamber 14701 that has a venting port 14702. Meanwhile, a sample A1 can be initially stored in the chamber 14102 of the basic fluidic unit 14101, a sample A2 can be initially stored in the chamber 14202 of the basic fluidic unit 14201 and a sample A3 can be initially stored in the chamber 14402 of the basic fluidic unit 14401. Additionally, a sample B1 can be induced into the fluidic conduit 14001 by an inlet port 14801 through a fluidic conduit 14801 with a valve 14803. The valve 14803 can be closed after inducing the sample. In some embodiments, the fluidic conduit 14001 can be used to collect a predetermined volume of the sample. Similarly, a sample B2 can be induced into the fluidic conduit 14002 by an inlet port 14901 through a fluidic conduit 14902 with a valve 14903. The valve 14903 can be closed after inducing the sample. In some embodiments, the fluidic conduit 14002 can be used to collect a predetermined volume of the sample.

Figure 14B:
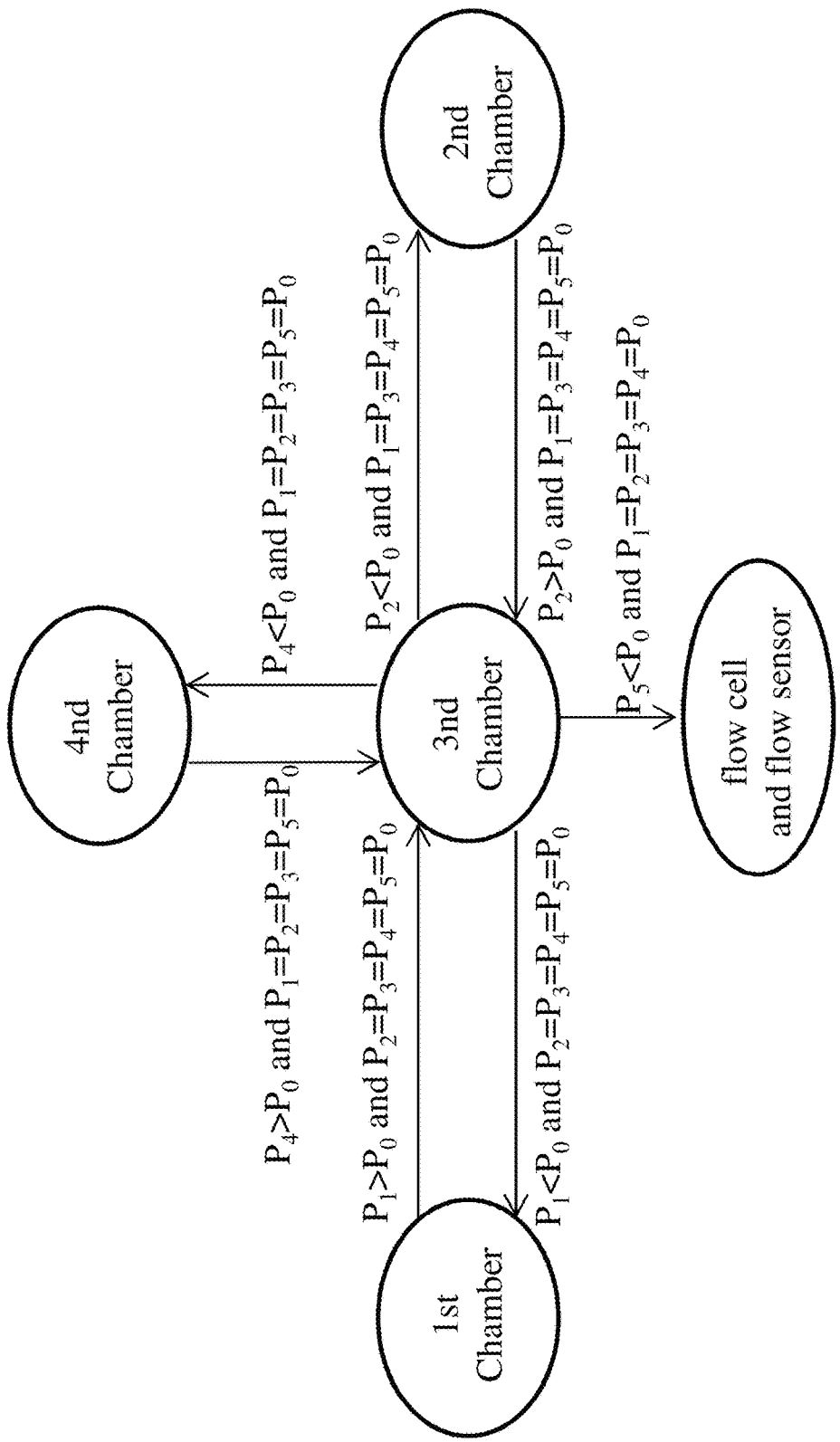

An exemplary method of controlling the pneumatic pressures ($P_1$, $P_2$, $P_3$, $P_4$ and $P_5$) is described below and the corresponding fluid transfer is shown in the diagram of FIG. 14B. The pneumatic pressure $P_5$ at the venting port 14702 of the reservoir 14701 balances with the pressure $P_5'$ at the downstream port 14604 of the flow sensor 14601, when there is a pneumatic path between these two ports (e.g., when there is air path in the reservoir 14701 to balance the venting port 14702 and the port 14604). A fluid sample in the first chamber (14102) can be transferred into the third chamber (14302) by applying a pneumatic control ($P_1>P_0$ and $P_2=P_3=P_4=P_5=P_0$), whereas a fluid sample in the third chamber can be transferred into the first chamber by applying a pneumatic control ($P_1>P_0$ and $P_2=P_3=P_4=P_5=P_0$), where $P_0$ is the atmosphere pressure. A fluid sample in the second chamber (14202) can be transferred into the third chamber by applying a pneumatic control ($P_2>P_0$ and $P_1=P_3=P_4=P_5=P_0$), whereas a fluid sample in the third chamber can be transferred into the second chamber by applying a pneumatic control ($P_2<P_0$ and $P_1=P_3=P_4=P_5=P_0$). Similarly, a fluid sample in the fourth chamber (14402) can be transferred into the third chamber by applying a pneumatic control ($P_4>P_0$ and $P_1=P_2=P_3=P_5=P_0$), whereas a fluid sample in the third chamber can be transferred into the fourth chamber by applying a pneumatic control ($P_4<P_0$ and $P_1=P_2=P_3=P_5=P_0$). Meanwhile, a fluid sample in the third chamber can be transferred into the flow cell and the flow sensor for the cytometer analysis, by applying a pneumatic control ($P_5<P_0$ and $P_1=P_2=P_3=P_4=P_0$). In this exemplary pneumatic control method, the vent port of the third chamber $P_3$ is kept at a constant pressure $P_3=P_0$ during the operations. Following the teachings of this disclosure and Applicants' previous disclosures (see, e.g., U.S. application Ser. No. 15/176,729 and PCT Application PCT/US16/36426, which are incorporated herein by reference in their entirety as if fully set forth), other methods can also be used to control the fluid transfer in this configuration.

In various embodiments, the sheathless flow cell is where the target particles in a fluid sample flow are detected and measured by different signals such as fluorescence, light scattering, light absorption, and light extinction, white light imaging, etc. An excitation light (EL) beam from a light source can be shaped and used to illuminate a designated sensing area of the flow cell, and trigger the above signals from the target particles.

The sheathless flow cell can be a fluidic channel that has various geometry shapes. FIGS. 15A-15D show the top view (in x-y plane) of a few examples of the flow cell. The top view (x-y plane) is defined as the plane perpendicular to the direction of the excitation light (z-axis). The length is defined the as channel dimension along the sample flow (x-axis), and the width is defined as the dimension along the y-axis. The depth is defined as the channel dimension along the z-axis. FIG. 15B shows an example of a flow cell that has a gradually decreased width, where the maximum width is $W_1$ and the minimum width is $W_2$. In other embodiments, the flow cell can have a gradually increased width. FIG. 15C shows an example of a flow cell that has a non-gradually changing width, where the maximum width is $W_1$ and the minimum width is $W_2$. FIG. 15D shows an example of a flow cell that has a fixed width ($W_1=W_2=W_0$) at various positions along channel length. In some embodiments, the difference of the maximum width $W_1$ and the minimum width $W_2$ are within a designated difference. A non-limiting example of the range of the width difference is $(W_1-W_2)/W_2 \leq 20\%$. The ranges of the channel width and the depth are chosen to be large enough so that target particles (e.g., cells in biological samples), can pass through the flow cell without blocking it. Meanwhile, they are chosen to be small enough to minimize the coincidence error in the flow cytometer analysis. The minimum width $W_1$ can be in the range of 1-10 μm, 10-40 μm, 40 to 100 μm, or 100 to 200 μm. The depth of the channel can be in the range of 1-10 μm, 10-40 μm, 40 to 100 μm, or 100 to 200 μm. The cross section of the channel (in y-z plane) can have the shape of a rectangular, a trapezoid, a circle, a half circle, or any other shapes. The length of the flow cell should be long enough for the optical detection of particles in the sample stream, and meanwhile, short enough to reduce the flow resistance of the sample stream flowing through. In various embodiments, the length of the flow cell can be in the range of about 1-10 μm, 10-100 μm, 100-1,000 μm, 1,000-10,000 μm, or 10,000-50,000 μm.

As the sheathless flow cell is used for optical measurement, at least one surface of the channel is transparent to the light wavelength involved in the measurement. The material for forming the channel surface can be any transparent material such as glass, quartz, and plastics including, but not limited to, Cyclic Olefin Copolymer (COC), Cyclo-olefin Polymer (COP), Poly-Methyl methacrylate (PMMA), polycarbonate (PC), Polystyrene (PS), and Poly-chloro-tri-fluoro-ethylene (PCTFE) materials such as Aclar, etc.

The fluid sample for analysis in the flow cell can be a fluid suspension of a plurality of particles. For example, the fluid sample can be a blood sample containing different cells such as white blood cells, red blood cells and platelets. In another example, the fluidic sample can be a blood sample, in which certain types of cells remain intact, such as white blood cells, while other types of cells have been lysed, such as red blood cells. In another example, the fluid sample can be a blood sample in which certain types of cells have been labeled with a fluorophore. In another example, the fluidic sample can be a mixture of the cells and other particles, such as non-fluorescent beads and/or fluorescent beads. In other examples, the fluid samples can also be other biological samples such as cerebrospinal fluid, urine, saliva, semen, etc.

When particles flow through the sheathless flow cell, various optical signals can be measured to detect and characterize the particles. The measurable signals include, but are not limited to, fluorescence, light scattering, light absorption, light distinction, etc. FIG. 16A shows an example where a plurality of particles flow through the flow cell for detection. All particles in the sample flow through in a one-by-one manner. Under the illumination of the excitation light (EL), each cell can be characterized for optical signals that include but are not limited to fluorescence (FL) and light scattering (LS). FIG. 16B shows another example where a plurality of particles flow through the flow cell for detection. Some particles are flowing through while overlapping with each other. Nevertheless, if only considering the target particles, they are flowing through still in a one-by-one manner without overlapping with other target particles. In this case, the light scattering from the target particles may be blocked by other particles overlapping with them. Nevertheless, other signals that include but are not limited to fluorescence signal can still be measured to detect these target particles, if these particles are treated with specific fluorophore to distinguish from the other particles beforehand. In some embodiments, the other particles can be non-fluorescent or treated with different fluorophore distinguishable from the target particles.

In an embodiment, the fluid sample can be a blood sample in which the white blood cells are labeled with fluorophore and the red blood cells are not labeled with fluorophore. When the labeled white blood cells pass through the flow cell one-by-one, the corresponding fluorescence signal can be measured to detect and characterize the white blood cell even when there are red blood cells overlapping with them. In another embodiment, the fluid sample can be a blood sample in which the white blood cells are labeled with fluorophore and the red blood cells are lysed. When the labeled white blood cells pass through the flow cell one-by-one, the corresponding fluorescence signal and light scattering signals can be measured simultaneously from these cells for detection and characterization. In another embodiment, the fluid sample can be a blood sample in which there are fluorophore-labeled white blood cells and fluorescent beads. When these white blood cells and the beads pass through the flow cell one-by-one, they can be detected by the corresponding fluorescence signal. Other cells having no fluorescence or a different wavelength of fluorescence do not impede the measurement. In another embodiment, the fluid sample can be a blood sample in which there are red blood cells and beads among other cells. When the cells pass through one-by-one, light scattering signals can be measured to detect and characterize the red blood cells and the beads. In yet other embodiment, the bead can be label with a fluorophore, so they can be distinguished from the red blood cells by the light scattering signals or by fluorescence signals, or by both signals.

Figure 17A:
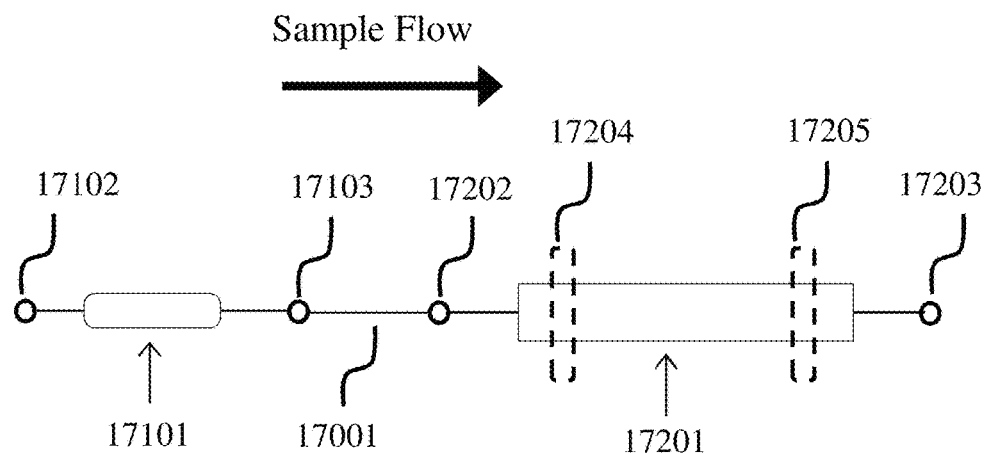
FIGS. 17A-17D illustrate, in accordance with various embodiments of the disclosure, exemplary designs for determining the absolute count of particles, where the outlet 17103 of the flow cell 17101 is coupled to the inlet 17202 of the flow sensor 17201 by a fluidic conduit 17001.
Figure 17B:
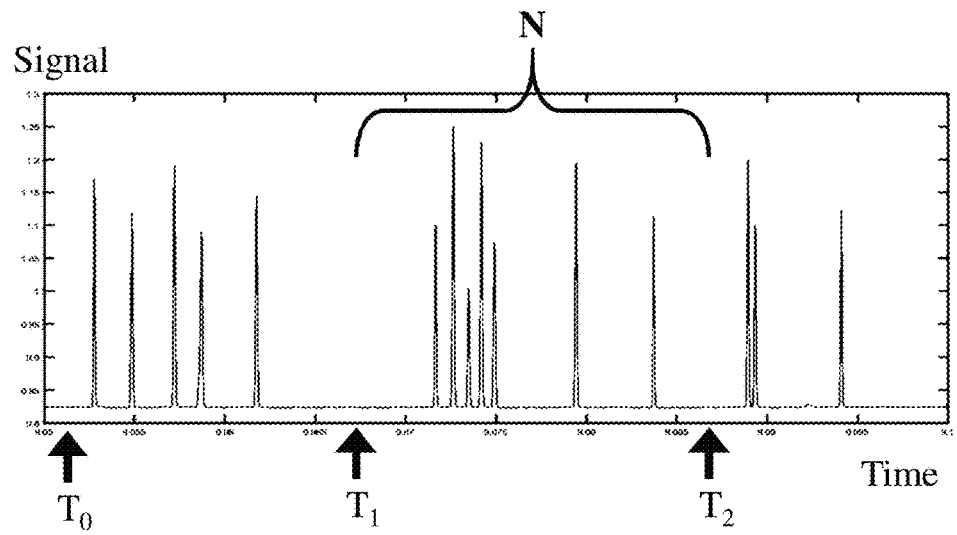

A combination of the sheathless flow cell and the flow sensor achieves the desired functionality of the cytometer analysis with the absolute count of particles. FIG. 17A shows one exemplary design, where the outlet 17103 of the flow cell 17101 is coupled to the inlet 17202 of the flow sensor 17201 by a fluidic conduit 17001. In certain embodiments, the outlet of the flow cell 17101 can be coupled to the inlet 17202 of the flow sensor 17201 directly and without additional fluidic conduit. The flow sensor 17201 has two sensing zones 17204 and 17205. A fluid sample flows into the inlet 17102 of the flow cell 17101 and then out of the outlet 17203 of the flow sensor 17201. The signal measured in the flow cell 17101 is recorded, as illustrated in FIG. 17B. Time $T_0$ is when the sample starts being detected in the flow cell 17101, $T_1$ is when the fluid sample passes the sensing zone 17204, and $T_2$ is when the fluid sample passes the sensing zone 17205. From time $T_1$ to $T_2$, the total number of target particles detected in the flow cell 17101 is N. The fluid volume $V_0$ between the two sensing zones 17204, 17205 is a known parameter from the design of the flow sensor. Because the flow cell 17101 has a sheathless design, the volume of fluid flows through the flow cell 17101 is only the fluid sample. Therefore, the sample volume being measured in the flow cell 17101 between $T_1$ and $T_2$ equals to $V_0$. In this design, the absolute count is determined as:

$$\text{Absolute Count } 1 = N/V_0 \qquad [4]$$

Figure 17C:
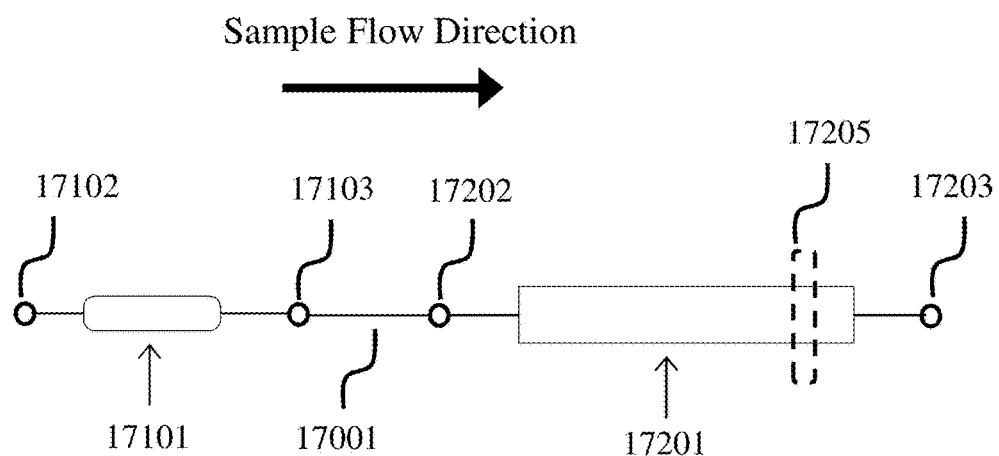
Figure 17D:
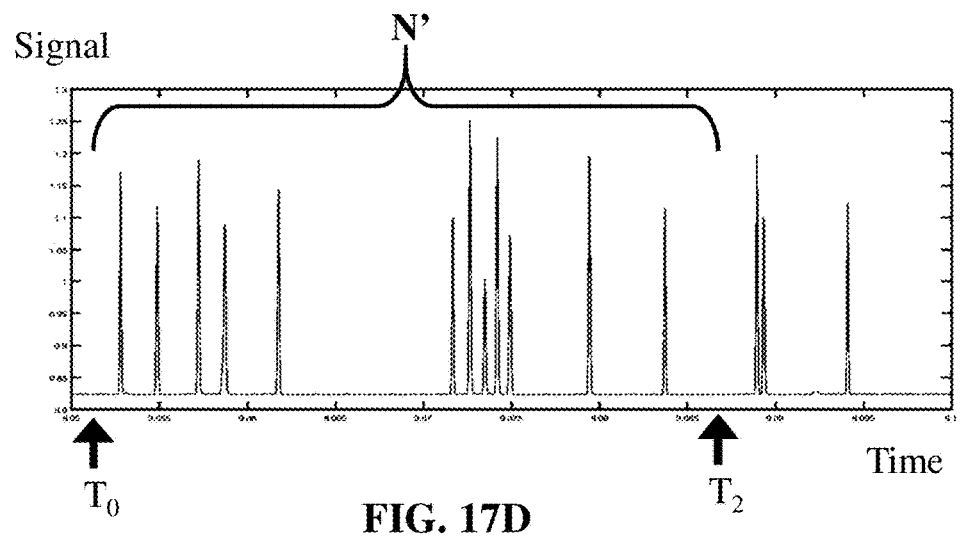

FIG. 17C shows another exemplary design, where the flow sensor 17201 has only one sensing zone 17205. FIG. 17D is the signal measured from this design, where time $T_0$ is when the sample starts being detected in the flow cell, and $T_2$ is when the fluid sample passes the sensing zone 17205. From time $T_0$ to $T_2$, the total number of target particles detected in the flow cell is N'. The volume $V_0'$ is the total fluid volume filling up the fluidic conduit from the flow cell 17101 to the sensing zone 17205. In this design, the absolute count is determined as:

Absolute Count $2=N'/V_0'$ [5]

Figure 18A:
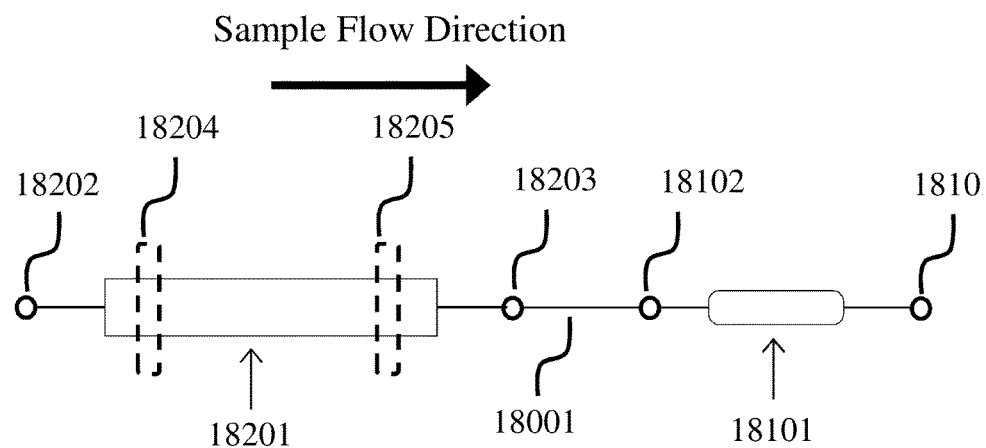
FIGS. 18A-18B illustrate, in accordance with various embodiments of the disclosure, another exemplary design for determining the absolute count of particles, where the inlet 18102 of the flow cell 18101 is coupled to the outlet 18203 of the flow sensor 18201 by a fluidic conduit 18001
Figure 18B:
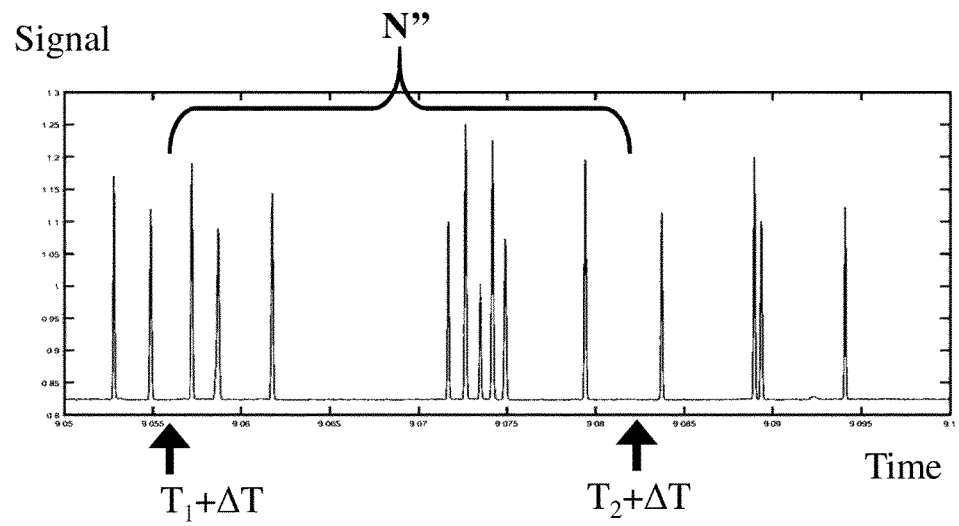

FIG. 18A shows another exemplary design, where the inlet 18102 of the flow cell 18101 is coupled to the outlet 18203 of the flow sensor 18201 by a fluidic conduit 18001. The flow sensor 18201 has two sensing zones 18204 and 18205. A fluid sample flows into the inlet 18102 of the flow sensor 18201 and then out of the outlet 18203 of the flow sensor 18201. The signal measured in the flow cell 18101 is recorded, as illustrated in FIG. 18B. $T_1$ is when the fluid sample passes the sensing zone 18204, and $T_2$ is when the fluid sample passes the sensing zone 18205. In this example, the number of cells counted N" is determined by the signal (A, T) between time points $T_1+\Delta T$ and $T_2+\Delta T$, as shown in FIG. 18B, where $\Delta T$ can be any empirical value to compensate the time delay between sample reaching the first sensing zone 18204 and sample reaching the flow cell 18101. From time $T_1+\Delta T$ to $T_2+\Delta T$, the total number of target particles detected in the flow cell is N". The fluid volume $V_0$ between the two sensing zones 18204, 18205 is a known parameter from the design of the flow sensor 18201. In this design, the absolute count is determined as:

Absolute Count $3=N''/V_0$ [6]

This combination of the flow cell 18101 and the flow sensor 18201 can be used for measurement of particles or cells. The size of the target particles can be in the range of 0.1-1 µm, 1-10 µm, 10-15 µm, 15-30 µm, 30-50 µm, or 50-100 µm depending on the size of the flow cell 18101. To minimize the risk of clogging the sheathless channel, the size of the particles being measured should be smaller than size of the flow cell 18101, and the size difference can range from 1-5 µm, 5-10 µm, 10-20 µm, or 20-50 µm. To minimize the coincidence error for the cytometer analysis, the concentration of the target particles in the fluid sample can be in the range of 1-100, 100-1000, 1000-5000, 5000-20,000, or 20,000-50,000 particles or cells per µl sample.

When the target particles are biological cells, too fast of a flow velocity in the sheathless flow cell can introduce shear force and may lyse the cells. Because the sheathless flow cell has a dimension similar to the target particles, this imposes a limitation on the flow rate of the sample. The flow rate can be in the range of 0.001-1, 1-50, 50-200, or 200-1000 microliters per minute (µl/min). In certain embodiments, the ranges can be 1-50 or 50-200 µl/min. For size consideration when implementing in self-contained cartridges, the range of the fluid sample volume can be constrained by the cartridge size. The volume of the flow sensor and the total volume of the sample can be in the range of 0.1-1 µl, 1-200 µl, 200-1000 µl, 1-5 ml, or 5-30 ml. In certain embodiments, the range can be 1-200 µl, 200-1000 µl, or 1-5 ml. In certain embodiments, by considering both the sample volume and the flow rate, the measurement is completed in less than 10 minutes.

By further incorporating the combination of the sheathless flow cell and the flow sensor with the basic fluidic unit, as illustrated in the examples shown in FIGS. 9A-14B, sample preparation steps can be further integrated with the cytometer analysis including the absolute count. The integration of the above functions enables the fluidic configurations to be operated as a self-contained structure for a cytometer analysis, without fluid exchange with the outside environment after the fluid samples having been loaded into the cartridge.

Figure 12D:
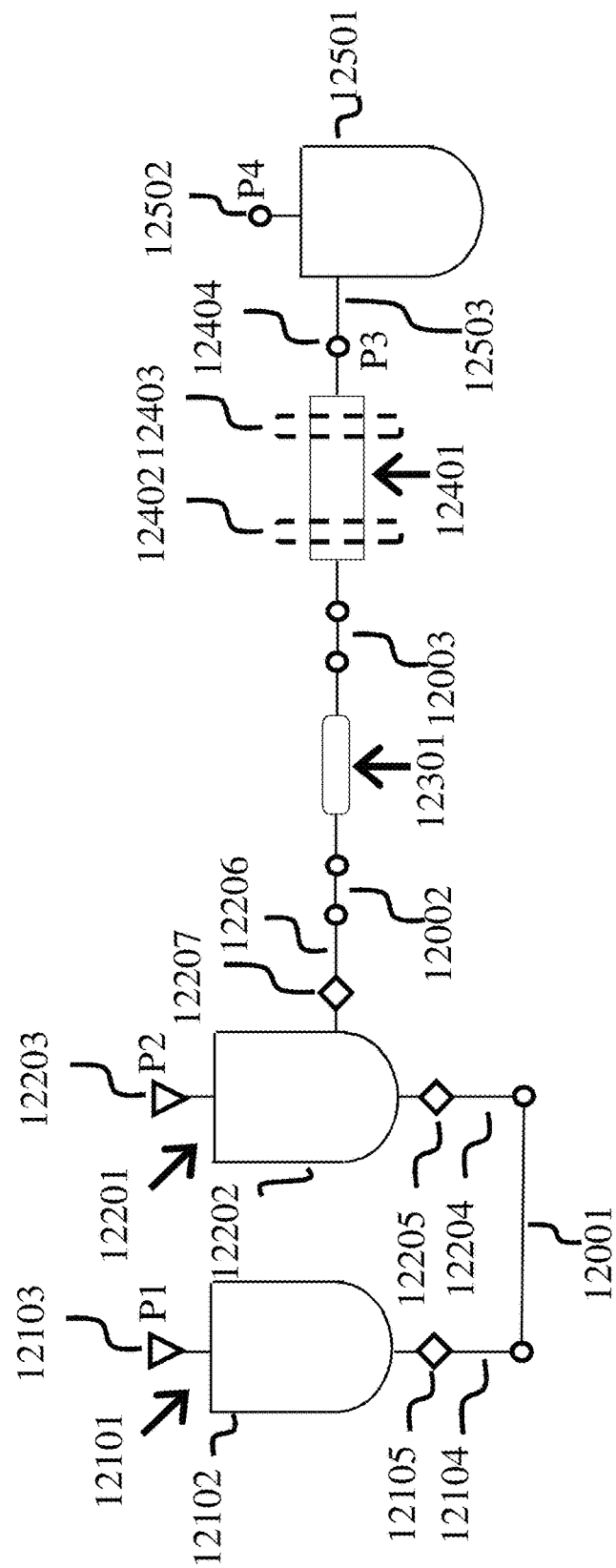
Figure 12E:
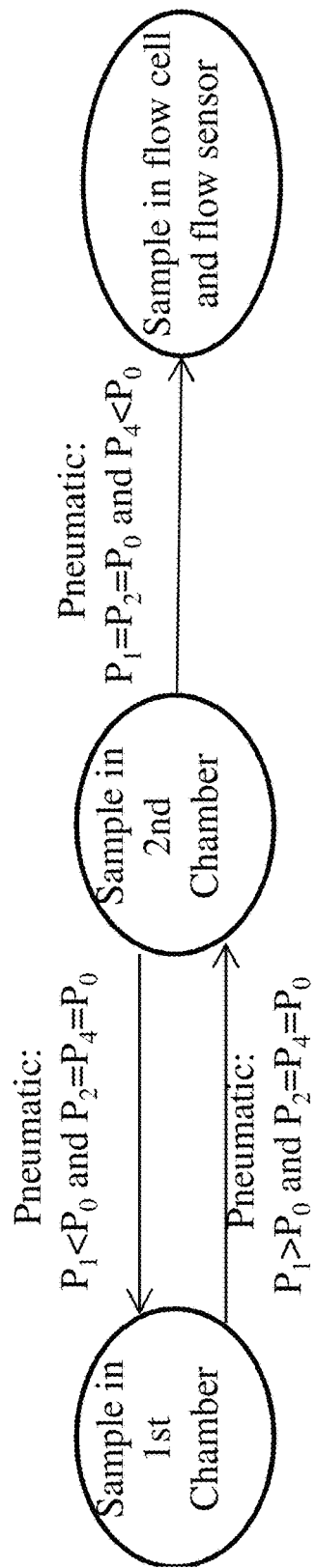
Figure 12F:
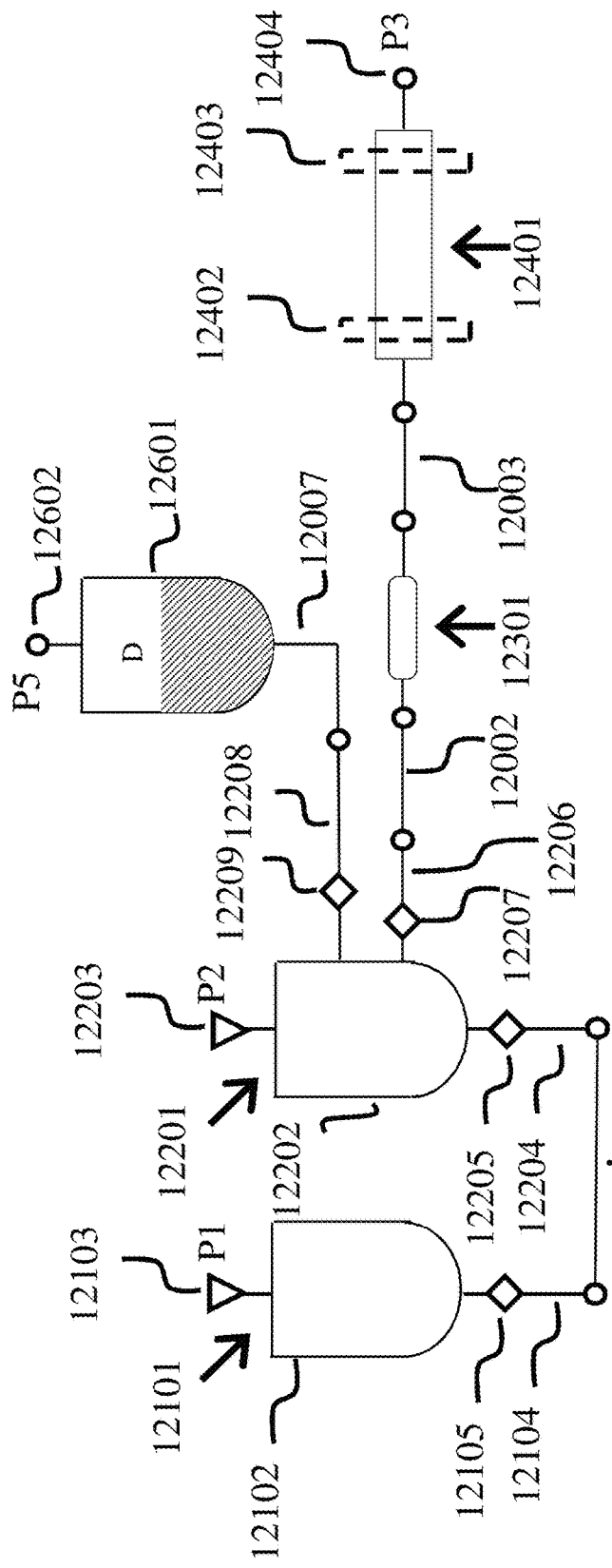
Figure 12G:
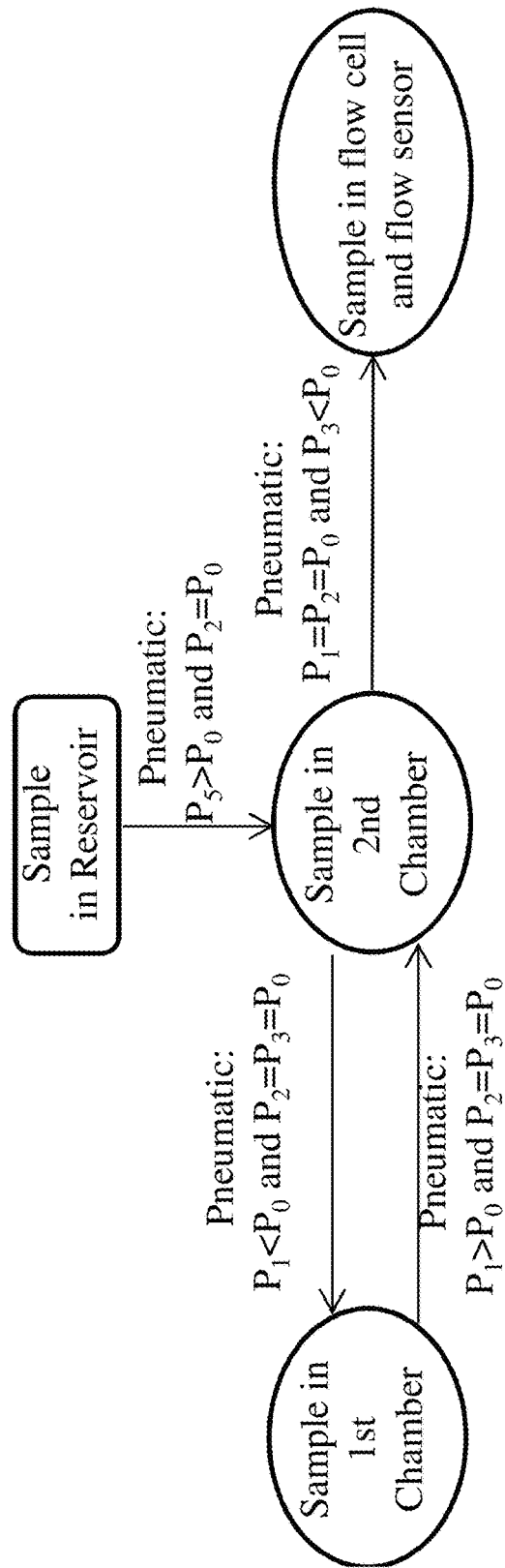

In different embodiments of the fluidic configurations, pneumatic pressures are applied to the venting ports of the basic fluidic units and additional venting ports of other fluidic structures such as a reservoir (see, e.g., FIG. 12D and FIG. 14A). The higher the pressure difference between two venting ports is, the higher the flow rate to transfer fluid in the microfluidic channels. When the fluid sample is a biological sample containing cells, a high flow rate in a confined channel may induce a large shear force to lyse the cells. Considering this limitation, the pressure difference between any two of the applied pressures can be in the range of 0-1, 1-5, 5-15, or 15-30 psi. In certain embodiments, the range can be 0-1, 1-5, or 5-15 psi. In certain embodiments, at least one of the venting ports can be connected to the atmosphere pressure of the environment. When at least one venting port is connected to the atmosphere pressure, another pressure higher than the atmosphere pressure applied introduces a positive pressure difference in comparison to the atmosphere pressure. This positive pressure difference can be in the range of 0-1, 1-5, 5-15, or 15-30 psi. In certain embodiments, the range can be 0-1, 1-5, or 5-15 psi. When at least one venting port is connected to the atmosphere pressure, another pressure lower than the atmosphere pressure applied introduces a negative pressure difference. This negative pressure difference can be in a range of 0-1, 1-5, 5-15, or 15-30 psi. In certain embodiments, the range can be 0-1, 1-5, or 5-15 psi. The flow rate achieved for transferring the sample via the channel between any two of the basic fluidic units can be in the range of 0-1, 1-50, 50-200, or 200-1000 µl/min, or 1-10 ml/min. In certain embodiments, the range can be 1 microliter to 1-50, 50-200, or 200-1000 µl/min.

Figure 19:
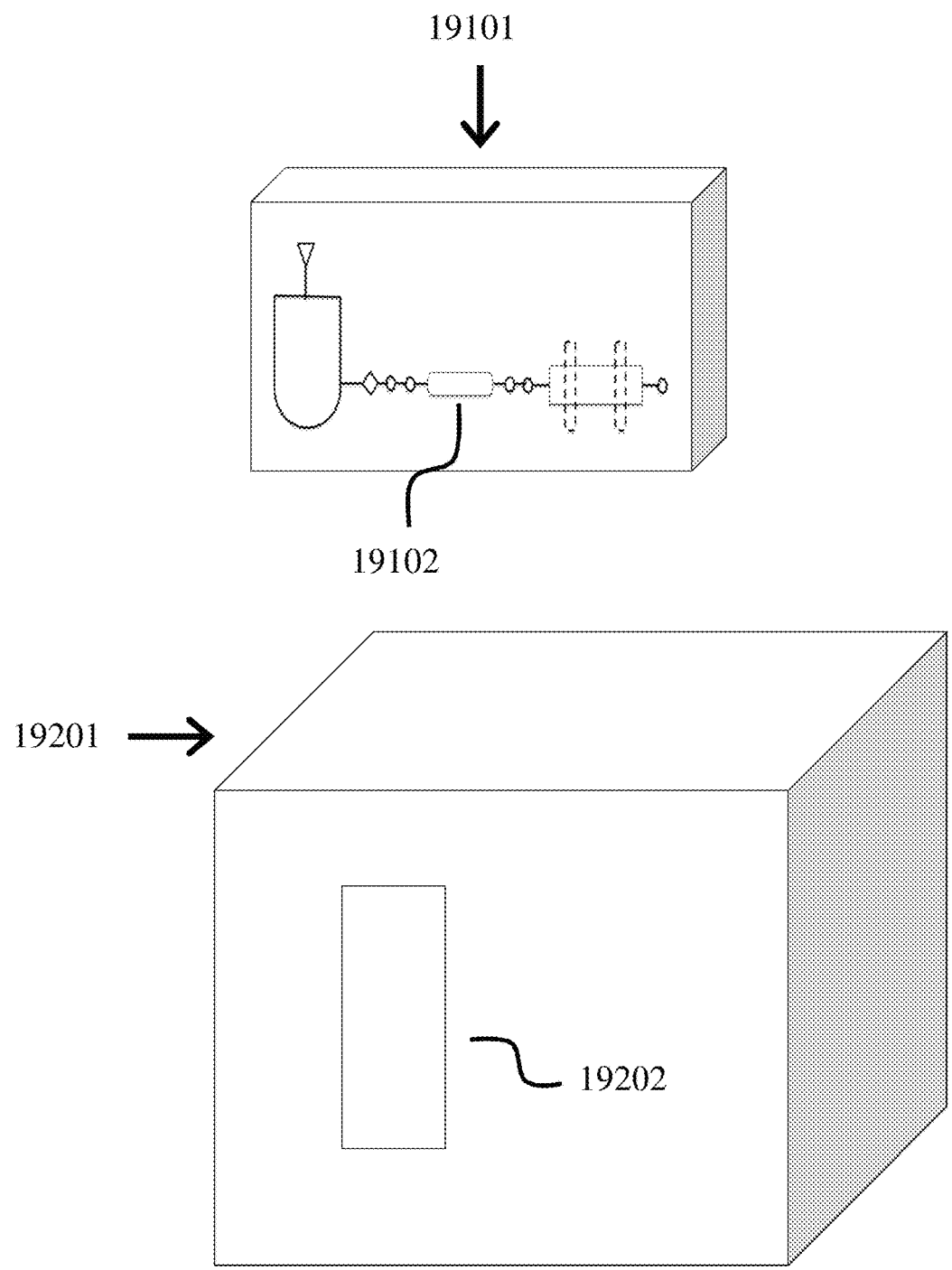
FIG. 19 illustrates, in accordance with various embodiments of the disclosure, one non-limiting example of an analyzer having a cartridge device and a reader instrument device. The cartridge 19101 having the fluidic structure 19102 can be inserted into a docking slot 19202 on the reader instrument 19201.

Various fluidic configurations incorporating a plurality of basic fluidic units and a plurality of the combinations of the sheathless flow cell and the flow sensor can be implemented in various manufacturing structures to form a fluidic cartridge. In some embodiments, this cartridge can be inserted into a reader instrument for operation, as shown in the example of FIG. 19. The cartridge 19101 having the fluidic structure 19102 can be inserted into a docking slot 19202 on the reader instrument 19201. In some embodiments, a control unit of the reader instrument records the signals from the cytometer analysis. Some examples of the signals include but are not limited to the optical signals such as fluorescence, light scattering, light absorption, etc. In some embodiments, the reader instrument has alignment mechanisms and features to align the sheathless flow cell with the optics in the instrument for optical signal measurement. In some embodiments, the control unit of the reader instrument also detects the signals from the flow sensor to determine the absolute count. In some embodiments, the control unit of the reader instrument also applies the pneumatic pressure source to the cartridges to drive the fluid transfer. In some embodiments, the control unit of the reader instrument also supports additional actuations such as opening or closing a valve structure in the cartridge fluidics. In some embodiments, the cartridge is self-contained and there is no exchange of liquid samples between the cartridge and the reader instrument. In some embodiments, the cartridge is not self-contained, and the reader instrument has on-board liquid storage and there is liquid exchange between the reader instrument and the cartridge, such as liquid infusion from the reader instrument into the cartridge.

In some embodiments, the cartridge stays stationary after being inserted into the reader, whereas the interface for external connections such as the pneumatic pressure source moves to make contact with the cartridge. In other embodiments, the cartridge can be movable after being inserted into the reader, and is moved to make contact with the interface for external connections such as pneumatic pressure sources.

Figure 20A:
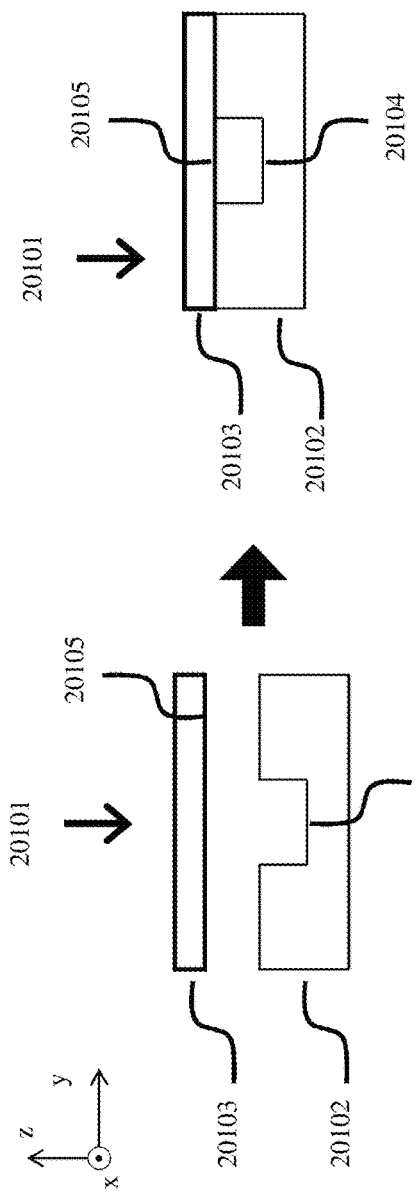
FIGS. 20A-20B illustrate, in accordance with various embodiments of the disclosure, exemplar processes for building a sheathless flow cell as described herein.
Figure 20B:
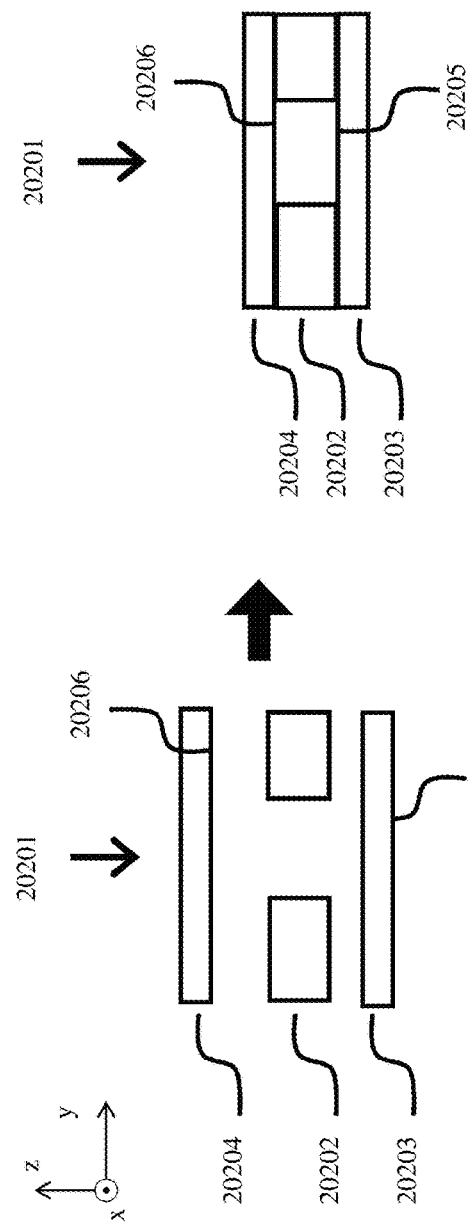

The sheathless flow cell in the fluidic structures can be built with various manufacturing processes. In some embodiments, an open fluidic channel for the flow cell can be built by injection molding, embossing, etching, CNC, laser cutting, or die cutting, etc. A cover can then be added onto the patterns to form enclosed fluidic channel to be the flow cell. The cover can be added by various manufacturing process, such as thermal fusion bonding, thermal lamination, adhesive bonding, solvent assisted bonding, laser wielding, and ultrasonic wielding, etc. Non-limiting examples of building the sheathless flow cell are described here. In some embodiments, optical signals are detected from particles flowing inside the sheathless flow cell. Smooth surface of the flow cell is useful to achieve acceptable optical signals. FIG. 20A shows one example of the sheathless flow cell 20101 having two pieces. The cross-section view (y-z plane) is perpendicular to the direction of sample flow (x-axis). The bottom piece 20102 forms three sides of a channel without a cover. The top piece 20103 adds a cover side to the channel, which then forms an enclosed channel. The bottom and the top surfaces 20104 and 20105 can achieve smoothness for optical measurement in the two pieces 20102 and 20103, respectively. FIG. 20B shows another example of building the sheathless flow cell 20201 having three pieces. The middle piece 20202 forms two sides of a channel, without top and bottom sides. Then a bottom piece 20203 and a top piece 20204 are added separately. The three pieces together forms an enclosed channel as the flow cell. The surface 20205 and 20206 can achieve smoothness for optical measurement in the two pieces 20203 and 20204, respectively.

The cartridge device for the cytometer analysis can be of any size. In certain embodiment, the cartridge device is received in the reader instrument device for the measurement and analysis and has a size in the range of about 0.1-1 $cm^3$, 1-5 $cm^3$, 5-25 $cm^3$, 25-50 $cm^3$, or 50-200 $cm^3$.

Many variations and alternative elements have been disclosed in embodiments of the present disclosure. Still further variations and alternate elements will be apparent to one of skill in the art. Among these variations, without limitation, are the selection of fluidic units, components and structures for the inventive devices and methods, and the samples that may be analyzed therewith. Various embodiments of the disclosure can specifically include or exclude any of these variations or elements.

In some embodiments, the numbers expressing quantities of ingredients, properties such as concentration, reaction conditions, and so forth, used to describe and claim certain embodiments of the disclosure are to be understood as being modified in some instances by the term "about." As one non-limiting example, one of ordinary skill in the art would generally consider a value difference (increase or decrease) no more than 10% to be in the meaning of the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclosure may contain certain errors necessarily resulting from the standard deviation found in their respective testing measurements.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The disclosure is explained by various examples, which are intended to be purely exemplary of the disclosure, and should not be considered as limiting the disclosure in any way. Various examples are provided to better illustrate the claimed disclosure and are not to be interpreted as limiting the scope of the disclosure. To the extent that specific materials are mentioned, it is merely for purposes of illustration and is not intended to limit the disclosure. One skilled in the art may develop equivalent means or reactants without the exercise of inventive capacity and without departing from the scope of the disclosure.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the disclosure are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the disclosure known to the applicant at this time of filing the application has been presented and is intended for the purposes of illustration and description. The present description is not intended to be exhaustive nor limit the disclosure to the precise form disclosed and many modifications and variations are possible in the light of the above teachings. The embodiments described serve to explain the principles of the disclosure and its practical application and to enable others skilled in the art to utilize the disclosure in various embodiments and with various modifications as are suited to the particular use contemplated. Therefore, it is intended that the disclosure not be limited to the particular embodiments disclosed for carrying out the disclosure.

While particular embodiments of the present disclosure have been shown and described, it will be obvious to those skilled in the art that, based upon the teachings herein, changes and modifications may be made without departing from this disclosure and its broader aspects and, therefore, the appended claims are to encompass within their scope all such changes and modifications as are within the true spirit and scope of this disclosure.

Additional Aspects of the Present Disclosure

Aspects of the subject matter described herein may be useful alone or in combination with any one or more of the other aspect described herein. Without limiting the foregoing description, in a first aspect of the present disclosure, a device for analyzing target particles in a sample includes a cartridge device, wherein the cartridge device comprises: an inlet configured for receiving the sample into the cartridge device; a fluidic structure fluidly connected to the inlet and configured for mixing at least a portion of the sample with at least a portion of a reagent to form one or more sample mixtures; a flow cell fluidly connected to the fluidic structure and configured for forming one or more sample streams from the one or more sample mixtures, wherein the sample streams are formed in the flow cell without a sheath flow, and wherein the flow cell comprises an optically transparent area configured for measuring an optical signal from the sample streams to detect the target particles in the sample; and a flow sensor fluidly connected to the flow cell and configured for measuring a sensing signal from the sample streams that enter the flow sensor.

In accordance with a second aspect of the present disclosure, which may be used in combination with any other aspect or combination of aspects listed herein, the fluidic structure comprises one or a plurality of chambers, wherein each chamber has a volume in the range of about 0.01-0.1 ml, 0.1-0.2 ml, 0.2-0.4 ml, 0.4-0.8 ml, 0.8-2 ml, or 2-10 ml; and wherein the fluidic structure is configured for transferring the sample mixtures from one of the chambers to the flow cell to form the sample streams.

In accordance with a third aspect of the present disclosure, which may be used in combination with any other aspect or combination of aspects listed herein, the flow cell has a width in the range of about 1-10 μm, 10-40 μm, 40-100 μm, or 100-200 μm and a depth in the range of about 1-10 μm, 10-40 μm, 40-100 μm, or 100-200 μm; and wherein the sample streams have a cross section of the same size as the flow cell.

In accordance with a fourth aspect of the present disclosure, which may be used in combination with any other aspect or combination of aspects listed herein, the flow cell has a length in the range of about of 1-10 μm, 10-100 μm, 100-1,000 μm, 1,000-10,000 μm, or 10,000-50,000 μm.

In accordance with a fifth aspect of the present disclosure, which may be used in combination with any other aspect or combination of aspects listed herein, the optically transparent area on the flow cell has a transmission rate of 50-60%, 60-70%, 70-80%, 80-90%, 90-96%, or 96-99.9% for the optical signal from the sample streams, and wherein the optical signal comprises scattered light, reflected light, transmitted light, fluorescence, light absorption, light extinction, or white light image, or a combination thereof.

In accordance with a sixth aspect of the present disclosure, which may be used in combination with any other aspect or combination of aspects listed herein, the optically transparent area on the flow cell is made of a plastic material.

In accordance with a seventh aspect of the present disclosure, which may be used in combination with any other aspect or combination of aspects listed herein, the cartridge device further comprises a reagent.

In accordance with an eighth aspect of the present disclosure, which may be used in combination with any other aspect or combination of aspects listed herein, the reagent comprises a fluorescent labeling agent that selectively labels the target particles in the sample with fluorescence, and wherein the optical signal from the sample streams comprises fluorescence.

In accordance with a ninth aspect of the present disclosure, which may be used in combination with any other aspect or combination of aspects listed herein, the flow sensor comprises a fluidic channel and a sensing zone on the fluidic channel, wherein the fluidic channel is fluidly connected to the flow cell to allow the sample streams to flow through; and wherein a sensing signal is measured when the sample streams enter the sensing zone.

In accordance with a tenth aspect of the present disclosure, which may be used in combination with any other aspect or combination of aspects listed herein, the fluidic channel in the flow sensor has a channel width in the range of about 0.001-0.05 mm, 0.05-1 mm, or 1-5 mm, and a channel depth in the range of about 0.001-0.01 mm, 0.01-0.5 mm, 0.5-1 mm, or 1-2 mm.

In accordance with a eleventh aspect of the present disclosure, which may be used in combination with any other aspect or combination of aspects listed herein, the sensing zone comprises an optically transparent area configured for measuring an optical signal that changes levels between the absence and presence of the sample streams in the sensing zone.

In accordance with a twelfth aspect of the present disclosure, which may be used in combination with any other aspect or combination of aspects listed herein, the fluidic connection between the flow cell and the flow sensor is configured for a sample stream to have the same flow rate flowing through the flow cell and the flow sensor.

In accordance with a thirteenth aspect of the present disclosure, which may be used in combination with any other aspect or combination of aspects listed herein, the fluidic structure comprises at least one basic fluidic unit that comprises: a chamber configured to accommodate a fluid; a venting port connected to the chamber, wherein the venting port is connected to a pneumatic pressure source, an ambient pressure, or the atmosphere pressure; a microfluidic channel connected to the chamber; and a valve on the microfluidic channel.

In accordance with a fourteenth aspect of the present disclosure, which may be used in combination with any other aspect or combination of aspects listed herein, the chamber has a volume in the range of about 0.01-0.1 ml, 0.1-0.2 ml, 0.2-0.4 ml, 0.4-0.8 ml, 0.8-2 ml, or 2-10 ml, and wherein the microfluidic channel has a cross section of a size in the range of about 0.001-0.01 $mm^2$, 0.01-0.1 $mm^2$, 0.1-0.25 $mm^2$, 0.25-0.5 $mm^2$, 0.5-1 $mm^2$, 1-2 $mm^2$, or 2-10 $mm^2$.

In accordance with a fifteenth aspect of the present disclosure, which may be used in combination with any other aspect or combination of aspects listed herein, the cartridge device is configured for transferring the sample mixtures from the chamber into the flow cell to form the sample streams when an external actuation mechanism is applied to the cartridge device, and wherein the external actuation mechanism comprises a pneumatic pressure source.

In accordance with a sixteenth aspect of the present disclosure, which may be used in combination with any other aspect or combination of aspects listed herein, when the cartridge device is in use, the chamber is so positioned that the at least a portion of the fluid inside the chamber is pulled by gravity towards the microfluidic channel and/or away from the venting port.

In accordance with a seventeenth aspect of the present disclosure, which may be used in combination with any other aspect or combination of aspects listed herein, when the cartridge device is in use, the chamber has a volume larger than the volume of the fluid accommodated therein and an air gap exists between the venting port and the fluid accommodated therein.

In accordance with a eighteenth aspect of the present disclosure, which may be used in combination with any other aspect or combination of aspects listed herein, the valve is a passive valve that is configured for allowing a fluid flow to pass through the microfluidic channel when a pneumatic pressure is applied to the fluid flow and stopping the fluid flow when no pneumatic pressure is applied to the fluid flow.

In accordance with a nineteenth aspect of the present disclosure, which may be used in combination with any other aspect or combination of aspects listed herein, the valve is a passive valve that comprises one of the following structures: (i) a channel with a hydrophilic inner surface embedded with a patch of a hydrophobic surface, (ii) a channel with a hydrophobic inner surface embedded with a patch of a hydrophilic surface, (iii) an enlargement of the channel cross section along the flow direction in a channel with a hydrophilic inner surface, and (iv) a contraction of the channel cross section along the flow direction in a channel with a hydrophobic inner surface.

In accordance with a twentieth aspect of the present disclosure, which may be used in combination with any other aspect or combination of aspects listed herein, the device further comprises a reader instrument device, wherein the reader instrument device is configured for receiving, operating, and/or actuating the cartridge device.

In accordance with a twenty-first aspect of the present disclosure, which may be used in combination with any other aspect or combination of aspects listed herein, the reader instrument device is configured for measuring the optical signal at the flow cell to quantify the target particles in the sample.

In accordance with a twenty-second aspect of the present disclosure, which may be used in combination with any other aspect or combination of aspects listed herein, the reader instrument device is configured for measuring the optical signal at the flow cell and the sensing signal at the flow sensor to determine the concentration of the target particles in the sample.

In accordance with a twenty-third aspect of the present disclosure, which may be used in combination with any other aspect or combination of aspects listed herein, a method for analyzing target particles in a sample includes applying the sample to a cartridge device, which is configured for collecting a predetermined sample volume into the cartridge device; transferring the cartridge device into a reader instrument device; mixing at least a portion of the collected sample and at least a portion of a reagent to form one or more sample mixtures inside the cartridge device; forming one or more sample streams from the one or more sample mixtures in a flow cell inside the cartridge device, wherein the sample streams are formed in the flow cell without a sheath flow; measuring an optical signal from the sample streams at the flow cell to detect the target particles in the sample streams; and using the reader instrument device to analyze the measured optical signal to quantify the target particles in the sample.

In accordance with a twenty-fourth aspect of the present disclosure, which may be used in combination with any other aspect or combination of aspects listed herein, the method includes flowing the sample streams through a flow sensor that is fluidly connected to the flow cell; measuring a sensing signal from the sample streams at the flow sensor to detect the entrance of the sample streams into the flow sensor and/or the exit of the sample streams out of the flow sensor; and using the reader instrument device to analyze the measured optical signal and sensing signal to determine the concentration of the target particles in the sample.

In accordance with a twenty-fifth aspect of the present disclosure, which may be used in combination with any other aspect or combination of aspects listed herein, the target particles have a size in the range of 0.1-1 µm, 1-10 µm, 10-15 µm, 15-30 µm, 30-50 µm, or 50-100 µm; and wherein the target particles have a concentration in the range of 1-100, 100-1000, 1000-5000, 5000-20,000, or 20,000-50,000 target particles per µl sample steam.

In accordance with a twenty-sixth aspect of the present disclosure, which may be used in combination with any other aspect or combination of aspects listed herein, the reagent comprises a fluorescent labeling agent that selectively labels the target particles in the sample with fluorescence, and wherein the optical signal from the sample streams comprises fluorescence.

In accordance with a twenty-seventh aspect of the present disclosure, which may be used in combination with any other aspect or combination of aspects listed herein, the mixing step is performed in a fluidic structure comprising one or a plurality of chambers, wherein each chamber has a volume in the range of about 0.01-0.1 ml, 0.1-0.2 ml, 0.2-0.4 ml, 0.4-0.8 ml, 0.8-2 ml, or 2-10 ml.

In accordance with a twenty-eighth aspect of the present disclosure, which may be used in combination with any other aspect or combination of aspects listed herein, the flow cell has a width in the range of about 1-10 µm, 10-40 µm, 40-100 µm, or 100-200 µm and a depth in the range of about 1-10 µm, 10-40 µm, 40-100 µm, or 100-200 µm; and wherein the sample streams have a cross section of the same size as the flow cell.

In accordance with a twenty-ninth aspect of the present disclosure, which may be used in combination with any other aspect or combination of aspects listed herein, the sample streams in the flow cell have a flow rate in the range of 0.001-0.01, 0.01-0.1, 0.1-1, 1-50, 50-200, or 200-1000 µl/min when the optical signal is measured from the sample streams.

In accordance with a thirtieth aspect of the present disclosure, which may be used in combination with any other aspect or combination of aspects listed herein, the optical signal measured from the sample streams at the flow cell comprises scattered light, reflected light, transmitted light, fluorescence, light absorption, light extinction, or white light image, or a combination thereof.

In accordance with a thirty-first aspect of the present disclosure, which may be used in combination with any other aspect or combination of aspects listed herein, the flow sensor comprises a fluidic channel and a sensing zone on the fluidic channel, wherein the fluidic channel is fluidly connected to the flow cell to allow the sample streams to flow through; and wherein a sensing signal is measured when the sample streams enter the sensing zone.

In accordance with a thirty-second aspect of the present disclosure, which may be used in combination with any other aspect or combination of aspects listed herein, the fluidic channel in the flow sensor has a channel width in the range of about 0.001-0.05 mm, 0.05-1 mm, or 1-5 mm, and a channel depth in the range of about 0.001-0.01 mm, 0.01-0.5 mm, 0.5-1 mm, or 1-2 mm; and wherein the sample streams in the flow cell and the flow sensor have the same flow rate.

In accordance with a thirty-third aspect of the present disclosure, which may be used in combination with any other aspect or combination of aspects listed herein, the sensing zone comprises an optically transparent area configured for measuring an optical signal that changes levels between the absence and presence of the sample streams in the sensing zone.

In accordance with a thirty-fourth aspect of the present disclosure, which may be used in combination with any other aspect or combination of aspects listed herein, mixing is performed in at least one basic fluidic unit that comprises: a chamber configured to accommodate a fluid, wherein the chamber has a volume in the range of about 0.01-0.1 ml, 0.1-0.2 ml, 0.2-0.4 ml, 0.4-0.8 ml, 0.8-2 ml, or 2-10 ml; a venting port connected to the chamber, wherein the venting port is connected to a pneumatic pressure source, an ambient pressure, or the atmosphere pressure; a microfluidic channel connected to the chamber, wherein the microfluidic channel has a cross section of a size in the range of about 0.001-0.01 $mm^2$, 0.01-0.1 $mm^2$, 0.1-0.25 $mm^2$, 0.25-0.5 $mm^2$, 0.5-1 $mm^2$, 1-2 $mm^2$, or 2-10 $mm^2$; and a valve on the microfluidic channel.

In accordance with a thirty-fifth aspect of the present disclosure, which may be used in combination with any other aspect or combination of aspects listed herein, the sample mixtures are transferred from the chamber into the flow cell to form the sample streams when an external actuation mechanism is applied to the cartridge device, and wherein the external actuation mechanism comprises a pneumatic pressure source.

In accordance with a thirty-sixth aspect of the present disclosure, which may be used in combination with any other aspect or combination of aspects listed herein, when the cartridge device is in use, the chamber is so positioned that the at least a portion of the fluid inside the chamber is pulled by gravity towards the microfluidic channel and/or away from the venting port.

In accordance with a thirty-seventh aspect of the present disclosure, which may be used in combination with any other aspect or combination of aspects listed herein, when the cartridge device is in use, the chamber has a volume larger than the volume of the fluid accommodated therein and an air gap exists between the venting port and the fluid accommodated therein In accordance with a thirty-eighth aspect of the present disclosure, which may be used in combination with any other aspect or combination of aspects listed herein, at least two separate sample mixtures are transferred into the same flow cell to form at least two separate sample streams.

In accordance with a thirty-ninth aspect of the present disclosure, which may be used in combination with any other aspect or combination of aspects listed herein, a method for analyzing particles in a sample includes applying the sample to a cartridge device, which is configured for collecting a predetermined sample volume into the cartridge device; transferring the cartridge device into a reader instrument device; mixing at least a portion of the collected sample and at least a portion of a reagent to form one or more sample mixtures inside the cartridge device; forming one or more sample streams from the one or more sample mixtures in a flow cell inside the cartridge device, wherein at least two separate sample mixtures are transferred into the same flow cell to form at least two separate sample streams without a sheath flow; measuring an optical signal from the sample streams at the flow cell to detect the target particles in the sample streams; and using the reader instrument device to analyze the measured optical signal to quantify the target particles in the sample.

In accordance with a fortieth aspect of the present disclosure, which may be used in combination with any other aspect or combination of aspects listed herein, a portion of the collected sample is mixed with a first reagent to form a first sample mixture and another portion of the collected sample is mixed with a second reagent to form a second sample mixture; and wherein the two sample mixtures are separately transferred into the flow cell to form two separate sample streams.

In accordance with a forty-first aspect of the present disclosure, which may be used in combination with any other aspect or combination of aspects listed herein, the two sample mixtures are separately formed in a chamber or separately transferred into a chamber before being separately transferred into the flow cell.

In accordance with a forty-second aspect of the present disclosure, which may be used in combination with any other aspect or combination of aspects listed herein, the chamber has a volume in the range of about 0.01-0.1 ml, 0.1-0.2 ml, 0.2-0.4 ml, 0.4-0.8 ml, 0.8-2 ml, or 2-10 ml.

In accordance with a forty-third aspect of the present disclosure, which may be used in combination with any other aspect or combination of aspects listed herein, the sample is collected into a fluidic conduit.

In accordance with a forty-fourth aspect of the present disclosure, which may be used in combination with any other aspect or combination of aspects listed herein, the fluidic conduit is closed by a valve and/or sealed by an external structure after the sample is collected into the fluidic conduit.

In accordance with a forty-fifth aspect of the present disclosure, which may be used in combination with any other aspect or combination of aspects listed herein, the fluidic conduit is configured for collecting a predetermine sample volume in the range of about 0.1-1 µL, 1-5 µL, 5-10 µL, 10-20 µL, or 20-50 µL.

In accordance with a forty-sixth aspect of the present disclosure, which may be used in combination with any other aspect or combination of aspects listed herein, at least a portion of the reagent is transferred into the fluidic conduit to flush a portion of the collected sample into a chamber to form a sample mixture.

In accordance with a forty-seventh aspect of the present disclosure, which may be used in combination with any other aspect or combination of aspects listed herein, at least one sample stream comprises white blood cells as the target particles detected in the flow cell and at least another sample stream comprises red blood cells and/or platelet cells as the target particles detected in the flow cell.

The invention claimed is:

1. A device for analyzing target particles in a sample, comprising:
    a cartridge device, wherein the cartridge device comprises:
    an inlet configured for receiving the sample into the cartridge device;
    a fluidic structure fluidly connected to the inlet and configured for mixing at least a portion of the sample with at least a portion of a reagent to form one or more sample mixtures;
    a flow cell fluidly connected to the fluidic structure and configured for forming one or more sample streams from the one or more sample mixtures, wherein the sample streams are formed in the flow cell without a sheath flow, and wherein the flow cell comprises an optically transparent area configured for measuring an optical signal from the sample streams to detect the target particles in the sample; and
    a flow sensor fluidly connected to the flow cell and configured for measuring a sensing signal from the sample streams that enter the flow sensor.

2. The device of claim 1, wherein the fluidic structure comprises one or a plurality of chambers, wherein each chamber has a volume in the range of about 0.01-0.1 ml, 0.1-0.2 ml, 0.2-0.4 ml, 0.4-0.8 ml, 0.8-2 ml, or 2-10 ml; and wherein the fluidic structure is configured for transferring the sample mixtures from one of the chambers to the flow cell to form the sample streams.

3. The device of claim 1, wherein the flow cell has a width in the range of about 1-10 µm, 10-40 µm, 40-100 µm, or 100-200 µm and a depth in the range of about 1-10 µm 10-40 µm, 40-100 µm, or 100-200 µm; and wherein the sample streams have a cross section of the same size as the flow cell.

4. The device of claim 1, wherein the flow cell has a length in the range of about of 1-10 µm, 10-100 µm, 100-1,000 µm, 1,000-10,000 µm, or 10,000-50,000 µm.

5. The device of claim 1, wherein the optically transparent area on the flow cell has a transmission rate of 50-60%, 60-70%, 70-80%, 80-90%, 90-96%, or 96-99.9% for the optical signal from the sample streams, and wherein the optical signal comprises scattered light, reflected light, transmitted light, fluorescence, light absorption, light extinction, or white light image, or a combination thereof.

6. The device of claim 1, wherein the optically transparent area on the flow cell is made of a plastic material.

7. The device of claim 1, wherein the cartridge device further comprises a reagent.

8. The device of claim 1, wherein the reagent comprises a fluorescent labeling agent that selectively labels the target particles in the sample with fluorescence, and wherein the optical signal from the sample streams comprises fluorescence.

9. The device of claim 1, wherein the flow sensor comprises a fluidic channel and a sensing zone on the fluidic channel, wherein the fluidic channel is fluidly connected to the flow cell to allow the sample streams to flow through; and wherein a sensing signal is measured when the sample streams enter the sensing zone.

10. The device of claim 9, wherein the fluidic channel in the flow sensor has a channel width in the range of about 0.001-0.05 mm, 0.05-1 mm, or 1-5 mm, and a channel depth in the range of about 0.001-0.01 mm, 0.01-0.5 mm, 0.5-1 mm, or 1-2 mm.

11. The device of claim 1, wherein the sensing zone comprises an optically transparent area configured for measuring an optical signal that changes levels between the absence and presence of the sample streams in the sensing zone.

12. The device of claim 1, wherein the fluidic connection between the flow cell and the flow sensor is configured for a sample stream to have the same flow rate flowing through the flow cell and the flow sensor.

13. The device of claim 1, wherein the fluidic structure comprises at least one basic fluidic unit that comprises:
    a chamber configured to accommodate a fluid;
    a venting port connected to the chamber, wherein the venting port is connected to a pneumatic pressure source, an ambient pressure, or the atmosphere pressure;
    a microfluidic channel connected to the chamber; and
    a valve on the microfluidic channel.

14. The device of claim 13, wherein the chamber has a volume in the range of about 0.01-0.1 ml, 0.1-0.2 ml, 0.2-0.4 ml, 0.4-0.8 ml, 0.8-2 ml, or 2-10 ml, and wherein the microfluidic channel has a cross section of a size in the range of about 0.001-0.01 mm2, 0.01-0.1 mm2, 0.1-0.25 mm2, 0.25-0.5 mm2, 0.5-1 mm2, 1-2 mm2, or 2-10 mm2.

15. The device of claim 13, wherein the cartridge device is configured for transferring the sample mixtures from the chamber into the flow cell to form the sample streams when an external actuation mechanism is applied to the cartridge device, and wherein the external actuation mechanism comprises a pneumatic pressure source.

16. The device of claim 13, wherein, when the cartridge device is in use, the chamber is so positioned that the at least a portion of the fluid inside the chamber is pulled by gravity towards the microfluidic channel and/or away from the venting port.

17. The device of claim 13, wherein, when the cartridge device is in use, the chamber has a volume larger than the volume of the fluid accommodated therein and an air gap exists between the venting port and the fluid accommodated therein.

18. The device of claim 13, wherein the valve is a passive valve that is configured for allowing a fluid flow to pass through the microfluidic channel when a pneumatic pressure is applied to the fluid flow and stopping the fluid flow when no pneumatic pressure is applied to the fluid flow.

19. The device of claim 13, wherein the valve is a passive valve that comprises one of the following structures: (i) a channel with a hydrophilic inner surface embedded with a patch of a hydrophobic surface, (ii) a channel with a hydrophobic inner surface embedded with a patch of a hydrophilic surface, (iii) an enlargement of the channel cross section along the flow direction in a channel with a hydrophilic inner surface, and (iv) a contraction of the channel cross section along the flow direction in a channel with a hydrophobic inner surface.

20. The device of claim 1, further comprising a reader instrument device, wherein the reader instrument device is configured for receiving, operating, and/or actuating the cartridge device.

21. The device of claim 20, wherein the reader instrument device is configured for measuring the optical signal at the flow cell to quantify the target particles in the sample.

22. The device of claim 20, wherein the reader instrument device is configured for measuring the optical signal at the flow cell and the sensing signal at the flow sensor to determine the concentration of the target particles in the sample.

23. A method for analyzing target particles in a sample using the device of claim 1, the method comprising:
applying the sample to the cartridge device, which is configured for collecting a predetermined sample volume into the cartridge device;
transferring the cartridge device into a reader instrument device;
mixing at least a portion of the collected sample and at least a portion of a reagent to form one or more sample mixtures inside the cartridge device;
forming one or more sample streams from the one or more sample mixtures in the flow cell, wherein the one or more sample streams are formed in the flow cell without a sheath flow;
measuring the optical signal from the one or more sample streams at the flow cell to detect the target particles in the sample streams;
using the reader instrument device to analyze the measured optical signal to quantify the target particles in the sample.

24. The method of claims 23, further comprising:
flowing the sample streams through a flow sensor that is fluidly connected to the flow cell;
measuring a sensing signal from the sample streams at the flow sensor to detect the entrance of the sample streams into the flow sensor and/or the exit of the sample streams out of the flow sensor; and
using the reader instrument device to analyze the measured optical signal and sensing signal to determine the concentration of the target particles in the sample.

25. The method of claim 23, wherein the target particles have a size in the range of 0.1-1 µm, 1-10 µm, 10-15 µm, 15-30 µm, 30-50 µm, or 50-100 µm; and wherein the target particles have a concentration in the range of 1-100, 100-1000, 1000-5000, 5000-20,000, or 20,000-50,000 target particles per µl sample steam.

26. The method of claim 23, wherein the reagent comprises a fluorescent labeling agent that selectively labels the target particles in the sample with fluorescence, and wherein the optical signal from the sample streams comprises fluorescence.

27. The method of claims 23, wherein the mixing step is performed in a fluidic structure comprising one or a plurality of chambers, wherein each chamber has a volume in the range of about 0.01-0.1 ml, 0.1-0.2 ml, 0.2-0.4 ml, 0.4-0.8 ml, 0.8-2 ml, or 2-10 ml.

28. The method of claim 23, wherein the flow cell has a width in the range of about 1-10 µm, 10-40 µm, 40-100 µm, or 100-200 µm and a depth in the range of about 1-10 µm, 10-40 µm, 40-100 µm, or 100-200 µm; and wherein the sample streams have a cross section of the same size as the flow cell.

29. The method of claim 23, wherein the sample streams in the flow cell have a flow rate in the range of 0.001-0.01, 0.01-0.1, 0.1-1, 1-50, 50-200, or 200-1000 µl/min when the optical signal is measured from the sample streams.

30. The method of claim 23, wherein the optical signal measured from the sample streams at the flow cell comprises scattered light, reflected light, transmitted light, fluorescence, light absorption, light extinction, or white light image, or a combination thereof.

31. The method of claim 23, wherein the flow sensor comprises a fluidic channel and a sensing zone on the fluidic channel, wherein the fluidic channel is fluidly connected to the flow cell to allow the sample streams to flow through; and wherein a sensing signal is measured when the sample streams enter the sensing zone.

32. The method of claim 31, wherein the fluidic channel in the flow sensor has a channel width in the range of about 0.001-0.05 mm, 0.05-1 mm, or 1-5 mm, and a channel depth in the range of about 0.001-0.01 mm, 0.01-0.5 mm, 0.5-1 mm, or 1-2 mm; and wherein the sample streams in the flow cell and the flow sensor have the same flow rate.

33. The method of claim 31, wherein the sensing zone comprises an optically transparent area configured for measuring an optical signal that changes levels between the absence and presence of the sample streams in the sensing zone.

34. The method of claim 23, wherein mixing is performed in at least one basic fluidic unit that comprises:
a chamber configured to accommodate a fluid, wherein the chamber has a volume in the range of about 0.01-0.1 ml, 0.1-0.2 ml, 0.2-0.4 ml, 0.4-0.8 ml, 0.8-2 ml, or 2-10 ml;

a venting port connected to the chamber, wherein the venting port is connected to a pneumatic pressure source, an ambient pressure, or the atmosphere pressure;

a microfluidic channel connected to the chamber, wherein the microfluidic channel has a cross section of a size in the range of about 0.001-0.01 mm2, 0.01-0.1 mm2, 0.1-0.25 mm2, 0.25-0.5 mm2, 0.5-1 mm2, 1-2 mm2, or 2-10 mm2; and a valve on the microfluidic channel.

35. The method of claim 34, wherein the sample mixtures are transferred from the chamber into the flow cell to form the sample streams when an external actuation mechanism is applied to the cartridge device, and wherein the external actuation mechanism comprises a pneumatic pressure source.

36. The method of claim 34, wherein, when the cartridge device is in use, the chamber is so positioned that the at least a portion of the fluid inside the chamber is pulled by gravity towards the microfluidic channel and/or away from the venting port.

37. The method of claim 34, wherein, when the cartridge device is in use, the chamber has a volume larger than the volume of the fluid accommodated therein and an air gap exists between the venting port and the fluid accommodated therein.

38. The method of claim 23, wherein at least two separate sample mixtures are transferred into the same flow cell to form at least two separate sample streams.

39. A method for analyzing target particles in a sample using the device of claim 1, the method comprising:

applying the sample to the cartridge device, which is configured for collecting a predetermined sample volume into the cartridge device;

transferring the cartridge device into a reader instrument device;

mixing at least a portion of the collected sample and at least a portion of a reagent to form one or more sample mixtures inside the cartridge device;

forming one or more sample streams from the one or more sample mixtures in the flow cell, wherein at least two separate sample mixtures are transferred into the flow cell to form at least two separate sample streams without a sheath flow;

measuring the optical signal from the sample streams at the flow cell to detect the target particles in the sample streams; and using the reader instrument device to analyze the measured optical signal to quantify the target particles in the sample.

40. The method of claim 39, wherein a portion of the collected sample is mixed with a first reagent to form a first sample mixture and another portion of the collected sample is mixed with a second reagent to form a second sample mixture; and wherein the two sample mixtures are separately transferred into the flow cell to form two separate sample streams.

41. The method of claim 40, wherein the two sample mixtures are separately formed in a chamber or separately transferred into a chamber before being separately transferred into the flow cell.

42. The method of claim 41, wherein the chamber has a volume in the range of about 0.01-0.1 ml, 0.1-0.2 ml, 0.2-0.4 ml, 0.4-0.8 ml, 0.8-2 ml, or 2-10 ml.

43. The method of claim 39, wherein the sample is collected into a fluidic conduit.

44. The method of claim 43, wherein the fluidic conduit is closed by a valve and/or sealed by an external structure after the sample is collected into the fluidic conduit.

45. The method of claim 43, wherein the fluidic conduit is configured for collecting a predetermine sample volume in the range of about 0.1-1 µL, 1-5 µL, 5-10 µL, 10-20 µL, or 20-50 µL.

46. The method of claim 43, wherein at least a portion of the reagent is transferred into the fluidic conduit to flush a portion of the collected sample into a chamber to form a sample mixture.

47. The method of claim 39, wherein at least one sample stream comprises white blood cells as the target particles detected in the flow cell and at least another sample stream comprises red blood cells and/or platelet cells as the target particles detected in the flow cell.

48. The device of claim 1, wherein the reagent consists of a fluorescent labeling agent.

49. The device of claim 1, wherein the reagent consists essentially of a fluorescent labeling agent.

50. The device of claim 1, wherein the reagent does not contain a magnetic material.

51. The device of claim 1, wherein the flow cell is configured for forming one sample stream without branching.

* * * * *